(12) United States Patent
Finney

(10) Patent No.: US 10,954,312 B2
(45) Date of Patent: Mar. 23, 2021

(54) METHOD EMPLOYING BISPECIFIC PROTEIN COMPLEX

(71) Applicant: UCB BIOPHARMA SRL, Brussels (BE)

(72) Inventor: Helene Margaret Finney, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 0 days.

(21) Appl. No.: 15/779,428

(22) PCT Filed: Dec. 1, 2016

(86) PCT No.: PCT/EP2016/079444
§ 371 (c)(1),
(2) Date: May 25, 2018

(87) PCT Pub. No.: WO2017/093410
PCT Pub. Date: Jun. 8, 2017

(65) Prior Publication Data
US 2018/0355063 A1 Dec. 13, 2018

(30) Foreign Application Priority Data
Dec. 3, 2015 (GB) .................................. 1521389

(51) Int. Cl.
| | | |
|---|---|---|
| *G01N 33/53* | (2006.01) | |
| *G01N 33/68* | (2006.01) | |
| *C07K 16/00* | (2006.01) | |
| *C07K 16/30* | (2006.01) | |
| *C07K 16/46* | (2006.01) | |
| *C07K 14/39* | (2006.01) | |
| *A61P 35/00* | (2006.01) | |
| *C07K 16/14* | (2006.01) | |
| *A61K 39/00* | (2006.01) | |

(52) U.S. Cl.
CPC ............ *C07K 16/468* (2013.01); *A61P 35/00* (2018.01); *C07K 14/39* (2013.01); *C07K 16/00* (2013.01); *C07K 16/14* (2013.01); *C07K 16/30* (2013.01); *A61K 2039/505* (2013.01); *A61K 2039/572* (2013.01); *A61K 2039/575* (2013.01); *C07K 2317/31* (2013.01); *C07K 2317/34* (2013.01); *C07K 2317/52* (2013.01); *C07K 2317/55* (2013.01); *C07K 2317/569* (2013.01); *C07K 2317/622* (2013.01); *C07K 2317/73* (2013.01); *C07K 2317/92* (2013.01); *C07K 2319/00* (2013.01); *C07K 2319/03* (2013.01); *C07K 2319/035* (2013.01); *C07K 2319/30* (2013.01); *C07K 2319/33* (2013.01)

(58) Field of Classification Search
CPC .. C07K 16/468; C07K 16/00; C07K 2317/33; C07K 2317/64; C07K 16/14; C07K 16/30; C07K 14/03; C07K 2319/00; C07K 2317/31; C07K 2317/34; C07K 2317/52; C07K 2317/55; C07K 2317/569; C07K 2317/73; C07K 2317/92; C07K 2319/035; C07K 2319/30; C07K 2317/622; C07K 2319/03; C07K 2319/33; A61P 35/00; A61P 37/06; A61P 29/00; G01N 33/6854; G01N 33/56966; G01N 33/563; G01N 66/536; G01N 33/53; G01N 33/505; G01N 33/5052; G01N 33/5058; G01N 33/5055; G01N 33/6866; G01N 33/6863; G01N 33/9493; G01N 33/574; G01N 33/57492; A61K 2039/505; A61K 2039/572; A61K 2039/575
See application file for complete search history.

(56) References Cited

U.S. PATENT DOCUMENTS

| | | |
|---|---|---|
| 4,741,900 A | 5/1988 | Alvarez et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |

(Continued)

FOREIGN PATENT DOCUMENTS

| | | |
|---|---|---|
| EP | 0392745 A2 | 10/1990 |
| EP | 0438474 B1 | 5/1996 |

(Continued)

OTHER PUBLICATIONS

Rodgers et al., Pro National Acad Sci 113: E459-E468 (Year: 2016).*

(Continued)

*Primary Examiner* — Phuong Huynh
(74) *Attorney, Agent, or Firm* — Medler Ferro Woodhouse & Mills PLLC

(57) ABSTRACT

The present invention is directed to a method of controlling and directing cells, for example to stimulate an immune response, inhibit an immune response, direct tissue regeneration or prevent tissue damage for therapeutic activity through the use of heterodimerically-tethered bispecific protein complex of formula A-X:Y-B. Component A may present X on the surface of a cell, may bind a protein (including a marker) expressed on the surface of an effector cell, or A-X is expressed on the surface of an effector cell, whilst B is specific to an epitope on target cell or tissue of interest. X:Y is a heterodimeric-tether which is formed by a binding interaction between X and Y, which together with A and B assists and effects the controlling and directing of the selected cells.

16 Claims, 5 Drawing Sheets
Specification includes a Sequence Listing.

(56) References Cited

U.S. PATENT DOCUMENTS

| | | |
|---|---|---|
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,698,426 A | 12/1997 | Huse |
| 5,731,168 A | 3/1998 | Carter et al. |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,798,229 A | 8/1998 | Strittmatter et al. |
| 5,821,047 A | 10/1998 | Garrard et al. |
| 5,969,108 A | 10/1999 | McCafferty et al. |
| 6,010,902 A | 1/2000 | Ledbetter et al. |
| 6,106,834 A | 8/2000 | Lazarovits et al. |
| 6,809,185 B1 | 10/2004 | Schoonjans et al. |
| 6,818,749 B1 | 11/2004 | Kashmiri et al. |
| 7,183,076 B2 | 2/2007 | Arathoon et al. |
| 8,088,378 B2 | 1/2012 | Chen et al. |
| 8,409,577 B2 | 4/2013 | Thompson et al. |
| 10,358,493 B2 | 7/2019 | Finney et al. |
| 10,370,447 B2 | 8/2019 | Finney et al. |
| 10,590,197 B2 | 3/2020 | Finney et al. |
| 10,618,957 B2 | 4/2020 | Finney et al. |
| 10,618,979 B2 | 4/2020 | Wright |
| 10,829,566 B2 | 11/2020 | Rapecki |
| 2003/0027247 A1 | 2/2003 | Wang et al. |
| 2003/0202975 A1 | 10/2003 | Tedder |
| 2005/0033031 A1 | 2/2005 | Cuoto |
| 2005/0048578 A1 | 3/2005 | Zhang |
| 2006/0252130 A1 | 11/2006 | Boehm et al. |
| 2007/0141672 A1 | 6/2007 | Shin |
| 2011/0076270 A1 | 3/2011 | Aversa et al. |
| 2013/0142787 A1 | 6/2013 | Chang et al. |
| 2013/0209463 A1 | 8/2013 | Rotman et al. |
| 2013/0336977 A1 | 12/2013 | Thompson et al. |
| 2014/0099254 A1 | 4/2014 | Chang et al. |
| 2014/0212425 A1 | 7/2014 | Chang et al. |
| 2015/0239974 A1 | 8/2015 | Chang et al. |
| 2017/0081404 A1 | 3/2017 | Finney et al. |
| 2017/0204178 A1 | 7/2017 | Finney et al. |
| 2017/0204183 A1 | 7/2017 | Finney et al. |
| 2018/0201678 A1 | 7/2018 | Finney et al. |
| 2018/0237521 A1 | 8/2018 | Finney et al. |
| 2018/0273620 A1 | 9/2018 | Finney et al. |
| 2018/0334513 A1 | 11/2018 | Wright |
| 2018/0334514 A1 | 11/2018 | Wright |
| 2018/0346603 A1 | 12/2018 | Bhatta et al. |
| 2018/0346604 A1 | 12/2018 | Rapecki |
| 2018/0355063 A1 | 12/2018 | Finney |
| 2019/0322739 A1 | 10/2019 | Finney et al. |

FOREIGN PATENT DOCUMENTS

| | | |
|---|---|---|
| EP | 0463151 B1 | 6/1996 |
| EP | 0546073 B1 | 9/1997 |
| EP | 1242457 B1 | 8/2004 |
| EP | 1570267 B1 | 10/2011 |
| EP | 2706069 A1 | 3/2014 |
| WO | WO86/01533 A1 | 3/1986 |
| WO | WO89/00195 A1 | 1/1989 |
| WO | WO89/01476 A1 | 2/1989 |
| WO | WO90/02809 A1 | 3/1990 |
| WO | 91/05568 A1 | 5/1991 |
| WO | WO91/09967 A1 | 7/1991 |
| WO | WO91/10737 A1 | 7/1991 |
| WO | WO92/01047 A1 | 1/1992 |
| WO | WO92/02551 A1 | 2/1992 |
| WO | WO92/18619 A1 | 10/1992 |
| WO | WO92/22583 A1 | 12/1992 |
| WO | WO93/06231 A1 | 4/1993 |
| WO | WO93/11162 A1 | 6/1993 |
| WO | WO93/11236 A1 | 6/1993 |
| WO | WO95/15982 A1 | 6/1995 |
| WO | WO95/20401 A1 | 8/1995 |
| WO | WO96/26964 A1 | 9/1996 |
| WO | 98/11918 A1 | 3/1998 |
| WO | WO98/20734 A1 | 5/1998 |
| WO | WO02/072832 A2 | 9/2002 |
| WO | WO03/012069 A2 | 2/2003 |
| WO | WO03/031581 A2 | 4/2003 |
| WO | WO03/048327 A2 | 6/2003 |
| WO | WO03/093320 A2 | 11/2003 |
| WO | WO2004/039840 A1 | 5/2004 |
| WO | WO2004/051268 A1 | 6/2004 |
| WO | WO2004/081051 A1 | 9/2004 |
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | 2005/016950 A1 | 2/2005 |
| WO | WO2005/026210 A2 | 3/2005 |
| WO | WO2005/113605 A1 | 12/2005 |
| WO | WO2005/117984 A2 | 12/2005 |
| WO | WO2005/118642 A2 | 12/2005 |
| WO | WO2006/004910 A2 | 1/2006 |
| WO | WO2006/119897 A2 | 11/2006 |
| WO | WO2007/060406 A1 | 5/2007 |
| WO | WO2007/085837 A1 | 8/2007 |
| WO | WO2007/087453 A2 | 8/2007 |
| WO | WO2007/146968 A2 | 12/2007 |
| WO | WO2008/070569 A2 | 6/2008 |
| WO | WO2008/119353 A1 | 10/2008 |
| WO | WO2009/012268 A1 | 1/2009 |
| WO | WO2009/040562 A1 | 4/2009 |
| WO | 2009/099728 A1 | 8/2009 |
| WO | 2009/120178 A1 | 10/2009 |
| WO | 2009/155724 A2 | 12/2009 |
| WO | 2010/027524 A1 | 3/2010 |
| WO | WO2010/035012 A1 | 4/2010 |
| WO | WO2011/025904 A1 | 3/2011 |
| WO | WO2011/061492 A2 | 5/2011 |
| WO | WO2011/086091 A1 | 7/2011 |
| WO | WO2011/130305 A2 | 10/2011 |
| WO | WO2011/131746 A2 | 10/2011 |
| WO | WO2012/023053 A2 | 2/2012 |
| WO | WO2012/116453 A1 | 9/2012 |
| WO | WO2012/151199 A1 | 11/2012 |
| WO | WO2012/162561 A2 | 11/2012 |
| WO | 2013/068563 A2 | 5/2013 |
| WO | WO2013/060867 A2 | 5/2013 |
| WO | WO2013/078455 A2 | 5/2013 |
| WO | WO2013/085893 A1 | 6/2013 |
| WO | WO2014/001326 A1 | 1/2014 |
| WO | WO2014/011518 A1 | 1/2014 |
| WO | WO2014/011519 A1 | 1/2014 |
| WO | WO2014/011520 A1 | 1/2014 |
| WO | WO2014/011521 A1 | 1/2014 |
| WO | 2014/066271 A1 | 5/2014 |
| WO | WO2014/096390 A1 | 6/2014 |
| WO | WO2014/131694 A1 | 9/2014 |
| WO | WO2015/021089 A1 | 2/2015 |
| WO | WO2015/057834 A1 | 4/2015 |
| WO | 2015/101587 A1 | 7/2015 |
| WO | WO2015/181282 A1 | 12/2015 |
| WO | WO2015/197772 A1 | 12/2015 |
| WO | WO2015/197789 A1 | 12/2015 |
| WO | WO2016/009029 A1 | 1/2016 |
| WO | WO2016/009030 A2 | 1/2016 |
| WO | WO2016/168773 A2 | 10/2016 |
| WO | WO2017/009473 A1 | 1/2017 |
| WO | WO2017/009476 A1 | 1/2017 |
| WO | WO2017/093402 A1 | 6/2017 |
| WO | WO2017/093404 A1 | 6/2017 |

(56) References Cited

FOREIGN PATENT DOCUMENTS

| WO | WO2017/093406 A1 | 6/2017 |
|---|---|---|
| WO | WO2017/093408 A1 | 6/2017 |

OTHER PUBLICATIONS

Non-Final Rejection issued in U.S. Appl. No. 15/311,198, dated Jul. 10, 2018.
Final Rejection issued in U.S. Appl. No. 15/311,198 dated Dec. 21, 2018.
Notice of Allowance issued in U.S. Appl. No. 15/311,198, dated Apr. 10, 2019.
Kussie et al., "A single engineered amino acid substitution changes antibody fine specificity" the Journal of Immunology (1994) 152:146-152.
Ward et al., "Binding activities of a repertoire of single immunoglobulin variable domains secreted from *Escherichia coli*," Nature (1989) 341:544-546.
Adair et al., "Therapeutic Antibodies," Drug Design Reviews Online 2(3):209-217 (2005).
Altschul et al., "Basic local alignment search tool," J Mol Biol 215(3):403-410 (1990).
Altschul et al., "Gapped BLAST and PSI-BLAST: a new generation of protein database search programs," Nucleic Acids Res 25(17):3389-3402 (1997).
Ames et al., "Conversion of murine Fabs isolated from a combinatorial phage display library to full length immunoglobulins," J Immunol Methods 184(2):177-186 (1995).
Angal et al., "A single amino acid substitution abolishes the heterogeneity of chimeric mouse/human (IgG4) antibody," Mol Immunol 30(1):105-108 (1993).
Armour et al., "Recombinant human IgG molecules lacking Fcgamma receptor I binding and monocyte triggering activities," Eur J Immunol 29(8):2613-2624 (1999).
Arndt et al., "Costimulation improves the killing capability of T cells redirected to tumor cells expressing low levels of CD33: description of a novel modular targeting system," Leukemia 28:59-69 (2014).
Babcook et al., "A novel strategy for generating monoclonal antibodies from single, isolated lymphocytes producing antibodies of defined specificities," Proc Natl Acad Sci USA 93(15):7843-7848 (1996).
Bartalena et al., "Thyroid hormone transport proteins," Clin Lab Med 13(3):583-598 (1993).
Berger et al., "Antigen recognition by conformational selection," FEBS Lett 450:149-153 (1999).
Bradshaw et al., "Concurrent detection of secreted products from human lymphocytes by microengraving: cytokines and antigen-reactive antibodies," Clin Immunol 129(1):10-18 (2008).
Bree et al., "Pharmacokinetics of intravenously administered 125I-labelled human alpha 1-acid glycoprotein," Clin Pharmacokinet 11(4):336-342 (1986).
Brinkmann et al., "Phage display of disulfide-stabilized Fv fragments," J Immunol Methods 182(1):41-50 (1995).
Brosterhus et al., "Enrichment and detection of live antigen-specific CD4(+) and CD8(+) T cells based on cytokine secretion," Eur J Immunol 29(12):4053-4059 (1999).
Bruhns et al., "Specificity and affinity of human Fcgamma receptors and their polymorphic variants for human IgG subclasses," Blood 113(16):3716-3725 (2009).
Burton et al., "Human antibodies from combinatorial libraries," Adv Immunol 57:191-280 (1994).
Caldas et al., "Humanization of the anti-CD18 antibody 6.7: an unexpected effect of a framework residue in binding to antigen," Mol Immunol 39:941-952 (2003).
Campbell et al., "Rapid detection, enrichment and propagation of specific T cell subsets based on cytokine secretion," *Clin Exp Immunol* 163:1-10 (2010).

Carnahan et al., "Epratuzumab, a CD22-targeting recombinant humanized antibody with a different mode of action from rituximab," Molecular Immunology 44(6):1331-1341 (2007).
Casset et al., "A peptide mimetic of an anti-CD4 monoclonal antibody by rational design," Biochem Biophys Res Comm 307:198-205 (2003).
Chan et al., "Therapeutic antibodies for autoimmunity and inflammation," Nat Rev Immunol 10(5):301-316 (2010).
Chang et al., "Loop-Sequence Features and Stability Determinants in Antibody Variable Domains by High-Throughput Experiments," Structure 22:9-21 (2014).
Chen et al., "Enhancement and destruction of antibody function by somatic mutation: unequal occurrence is controlled by V gene combinatorial associations," *EMBO J* 14(12):2784-2794 (1995).
Chien et al., "Significant structural and functional change of an antigen-binding site by a distant amino acid substitution: Proposal of a structural mechanism," Proc Natl Acad Sci USA 86:5532-5536 (1989).
Chothia et al., "Canonical structures for the hypervariable regions of immunoglobulins," J Mol Biol 196(4):901-917 (1987).
Chu et al., "Suppression of rheumatoid arthritis B cells by XmAb5871, an anti-CD19 antibody that coengages B cell antigen receptor complex and Fcγ receptor IIb inhibitory receptor," Arthritis Rheumatol 66:1153-1164 (2014).
Clargo et al., "The rapid generation of recombinant functional monoclonal antibodies from individual, antigen-specific bone marrow-derived plasma cells isolated using a novel fluorescence-based method," MAbs 6(1):143-159 (2014).
Crameri et al., "DNA shuffling of a family of genes from diverse species accelerates directed evolution," Nature 391:288-291 (1998).
Czerwinski et al., "Construction of dimeric F(ab) useful in blood group serology," Transfusion 42(2):257-264 (2002).
Datta-Mannan et al., "Humanized IgG1 variants with differential binding properties to the neonatal Fc receptor: relationship to pharmacokinetics in mice and primates," Drug Metab Dispos 35(1):86-94 (2007).
De Pascalis et al., "Grafting of 'Abbreviated' Complementarity-Determining Regions Containing Specificity—Determining Residues Essential for Ligand Contact to Engineer a Less Immunogenic Humanized Monoclonal Antibody," J Immunol 169:3076-3084 (2002).
Dennis et al., "Albumin Binding as a General Strategy for Improving the Pharmacokinetics of Proteins," J Biol Chem 277(38):35035-35043 (2002).
Dmitrova et al., "A new LexA-based genetic system for monitoring and analyzing protein heterodimerization in *Escherichia coli,*" Mol Gen Genet 257:205-212 (1998).
Doerner et al., "Therapeutic antibody engineering by high efficiency cell screening," *FEBS Lett* 588:278-287 (2014).
Dubowchik et al., "Receptor-mediated and enzyme-dependent targeting of cytotoxic anticancer drugs," Pharmacol Ther 83(2):67-123 (1999).
Dunkin et al., "Immune cell therapy in IBD," Dig Dis 32:61-66 (2014).
Feldman et al., "Adoptive Cell Therapy—Tumor-Infiltrating Lymphocytes, T-Cell Receptors, and Chimeric Antigen Receptors," Semin Oncol 42(4):626-639 (2015).
Finney et al., "Chimeric receptors providing both primary and costimulatory signaling in T cells from a single gene product," J Immunol 161:2791-2797 (1998).
Gish et al., "Identification of protein coding regions by database similarity search," Nat Genet 3(3):266-272 (1993).
Gitlin et al., "The selectivity of the human placenta in the transer of plasma proteins from mother to fetus," J Clin Invest 43:1938-1951 (1964).
Giusti et al., "Somatic diversification of S107 from an antiphosphocoline to an anti-DNA autoantibody is due to a single base change in its heavy chain variable region," Proc Natl Acad Sci USA 84:2926-2930 (1987).
Glockshuber et al., "A comparison of strategies to stabilize immunoglobulin Fv-fragments," Biochemistry 29(6):1362-1367 (1990).
Gold et al., "The B Cell Antigen Receptor Activates the Akt (Protein Kinase B)/Glycogen Synthase Kinase-3 Signaling Pathway via Phosphatidylinositol 3-Kinase," *J Immunol* 163:1894-1905 (1999).

(56) References Cited

OTHER PUBLICATIONS

Goldenberg et al., "Multifunctional Antibodies by the Dock-and-Lock Method for Improved Cancer Imaging and Therapy by Pretargeting," J Nuc Med 49(1):158-163 (2008).
Gussow et al., "Humanization of Monoclonal Antibodies," Meth Enzymol 203:99-121 (1991).
Hanes et al., "Ribosome display efficiently selects and evolves high-affinity antibodies in vitro from immune libraries," Proc Natl Aced Sci USA 95:14130-14135 (1998).
Harris, "Processing of C-terminal lysine and arginine residues of proteins isolated from mammalian cell culture," J Chromatogr A 705(1):129-134 (1995).
Hermiston et al., "CD45: A Critical Regulator of Signaling Thresholds in Immune Cells," Ann Rev Immunol 21:107-137 (2003).
Hinnebusch, "Evidence for translational regulation of the activator of general amino acid control in yeast," Proc Natl Acad Sci USA 81:6442-6446 (1984).
Hinton et al., "Engineered human IgG antibodies with longer serum half-lives in primates," J Biol Chem 279(8):6213-6216 (2004).
Hollinger et al., "Engineered antibody fragments and the rise of single domains," Nat Biotechnol 23(9):1126-1136 (2005).
Holm et al., "Functional mapping and single chain construction of the anti-cytokeratin 8 monoclonal antibody TS1l," Mol Immunol 44:1075-1084 (2007).
Holmes, "Buy buy bispecific antibodies," Nat Rev Drug Discov 10(11):798-800 (2011).
Holt et al., "Anti-serum albumin domain antibodies for extending the half-lives of short lived drugs," Protein Eng Des Sel 21(5):283-288 (2008).
Hope et al., "GCN4 protein, synthesized in vitro, binds HIS3 regulatory sequences: implications for general control of amino acid biosynthetic genes in yeast," Cell 43(1):177-188 (1985).
Idusogie et al., "Mapping of the C1q binding site on rituxan, a chimeric antibody with a human IgG1 Fc," J Immunol 164(8):4178-1484 (2000).
Idusogie et al., "Engineered antibodies with increased activity to recruit complement," J Immunol 166(4):2571-2575 (2001).
Jourdan et al., "An in vitro model of differentiation of memory B cells into plasmablasts and plasma cells including detailed phenotypic and molecular characterization," Blood 114(25):5173-5181 (2009).
Jung et al., "Design of interchain disulfide bonds in the framework region of the Fv fragment of the monoclonal antibody B3," Proteins 19(1):35-47 (1994).
Karnell et al., "CD19 and CD32b Differentially Regulate Human B Cell Responsiveness," J Immunol 192(4):1480-1490 (2014).
Kashmiri et al., "SDR grafting—a new approach to antibody humanization," Methods 36(1):25-34 (2005).
Keller et al., "Independent Metalloregulation of Ace1 and Mac1 in *Saccharomyces cerevisiae*," Eukaryot Cell 4(11):1863-1871 (2005).
Kettleborough et al., "Isolation of tumor cell-specific single-chain Fv from immunized mice using phage-antibody libraries and the re-construction of whole antibodies from these antibody fragments," Eur J Immunol 24(4):952-958 (1994).
Ko et al., "Engineering Antibodies for Dual Specificity and Enhanced Potency," Biotechnol Bioprocess Eng 20:201-210 (2015).
Kohler et al., "Continuous cultures of fused cells secreting antibody of predefined specificity," Nature 256:495-497 (1975).
Konterman et al., "Dual targeting strategies with bispecific antibodies," mAbs, 4(2):182-197 (2012).
Kozbor et al., "The production of monoclonal antibodies from human lymphocytes," Immunol Today 4(3):72-79 (1983).
Kudo et al., "T lymphocytes expressing a CD16 signaling receptor exert antibody-dependent cancer cell killing," Cancer Res 74(1):93-103 (2014).
Labrijn et al., "Therapeutic IgG4 antibodies engage in Fab-arm exchange with endogenous human IgG4 in vivo," Nat Biotechnol 27(8):767-771 (2009).

Lazar et al., "Engineered antibody Fc variants with enhanced effector function," Proc Natl Acad Sci USA 103(11):4005-4010 (2006).
Love et al., "A microengraving method for rapid selection of single cells producing antigen-specific antibodies," Nat Biotechnol 24(6):703-707 (2006).
Low et al., "Mimicking Somatic Hypermutation: Affinity Maturation of Antibodies Displayed on Bacteriophage Using a Bacterial Mutator Strain," J Mol Biol 260(3):359-368 (1996).
Luo et al., "Vl-linker-Vh orientation-dependent expression of single chain Fv-containing an engineered disulfide-stabilized bond in the framework regions," J Biochem 118(4):825-831 (1995).
Luo et al., "Design and Applications of Bispecific Heterodimers: Molecular Imaging and Beyond," Mol Pharm 11:1750-1761 (2014).
MacCallum et al., "Antibody-antigen Interactions: Contact Analysis and Binding Site Topography," J Mol Biol 262:732-745 (1996).
Madden et al., "Applications of network BLAST server," Methods Enzymol 266:131-141 (1996).
Mahoney et al., "Combination cancer immunotherapy and new immunomodulatory targets," Nat Rev Drug Discov 14:561-584 (2015).
Mariuzza et al., "The Structural Basis of Antigen-Antibody Recognition," Ann Rev Biophys Biophys Chem 16:139-159 (1987).
Marks et al., "By-passing immunization: building high affinity human antibodies by chain shuffling," Bio/Technology 10(7):779-783 (1992).
Merchant et al., "An efficient route to human bispecific IgG," Nat Biotechnol 16(7):677-681 (1998).
Moore et al., "Application of dual affinity retargeting molecules to achieve optimal redirected T-cell killing of B-cell lymphoma," Blood 117(17):4542-4551 (2011).
Muller et al., "Bispecific antibodies for cancer immunotherapy: Current perspectives," BioDrugs 24:89-98 (2010).
Nunez-Prado et al., "The coming of age of engineered multivalent antibodies," Drug Discov Today 20(5):588-594 (2015).
Nygren et al., "Scaffolds for engineering novel binding sites in proteins," Curr Opin Struct Biol 7(4):463-469 (1997).
Patten et al., "Applications of DNA shuffling to pharmaceuticals and vaccines," Curr Opin Biotechnol 8(6):724-733 (1997).
Persic et al., "An integrated vector system for the eukaryotic expression of antibodies or their fragments after selection from phage display libraries," Gene 187(1):9-18 (1997).
Pfeifer et al., "Anti-CD22 and anti-CD79B antibody drug conjugates are active in different molecular diffuse large B-cell lymphoma subtypes," Leukemia 29:1578-1586 (2015).
Peters, "Serum albumin," Adv Protein Chem 37:161-245 (1985).
Pule et al., "Artificial T-cell receptors," Cytotherapy 5(3):211-226 (2003).
Rajagopal et al., "A form of anti-Tac(Fv) which is both single-chain and disulfide stabilized: comparison with its single-chain and disulfide-stabilized homologs," Protein Eng 10(12):1453-1459 (1997).
Reiter et al., "Stabilization of the Fv fragments in recombinant immunotoxins by disulfide bonds engineered into conserved framework regions," Biochemistry 33(18):5451-5159 (1994).
Reiter et al., "Improved binding and antitumor activity of a recombinant anti-erbB2 immunotoxin by disulfide stabilization of the Fv fragment," J Biol Chem 269(28):18327-18331 (1994).
Richards et al., "Optimization of antibody binding to FcgammaRlla enhances macrophage phagocytosis of tumor cells," Mol Cancer Ther 7(8):2517-2527 (2008).
Ridgway et al., "'Knobs-into-holes' engineering of antibody CH3 domains for heavy chain heterodimerization," Protein Eng 9:617-621 (1996).
Rodgers et al., "Switch-mediated activation and retargeting of CAR-T cells for B-cell malignancies," Proc Natl Acad Sci USA 113(4):E459-E468 (2016).
Rudikoff et al., "Single amino acid substitution altering antigen-binding specificity," Proc Natl Acad Sci USA 79:1979-1983 (1982).
Ryan et al., "Antibody targeting of B-cell maturation antigen on malignant plasma cells," Mol Cancer Ther 6(11):3009-3018 (2007).
Schoonjans et al., "A new model for intermediate molecular weight recombinant bispecific and trispecific antibodies by efficient

(56) References Cited

OTHER PUBLICATIONS heterodimerization of single chain variable domains through fusion to a Fab-chain," Biomol Eng 17:193-202 (2001).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276(9):6591-6604 (2001).
Spang et al., "Heterodimeric Barnase-Barstar Vaccine Molecules: Influence of One versus Two Targeting Units Specific for Antigen Presenting Cells," PLoS One 7(9):e45393 (2012).
Stavenhagen et al., "Enhancing the potency of therapeutic monoclonal antibodies via Fc optimization," Adv Enzyme Regul 48:152-164 (2008).
Stavenhagen et al., "Fc optimization of therapeutic antibodies enhances their ability to kill tumor cells in vitro and controls tumor expansion in vivo via low-affinity activating Fcgamma receptors," Cancer Res 16(18):8882-8890 (2007).
Steurer et al., "Ex vivo coating of islet cell allografts with murine CTLA4/Fc promotes graft tolerance," J Immunol 155(3):1165-1174 (1995).
Thireos et al., "5' untranslated sequences are required for the translational control of a yeast regulatory gene," Proc Natl Acad Sci USA 81:5096-5100 (1984).
Thompson et al., "Affinity maturation of a high-affinity human monoclonal antibody against the third hypervariable loop of human immunodeficiency virus: use of phage display to improve affinity and broaden strain reactivity," J Mol Biol 256(1):77-88 (1996).
Thorpe et al., "The preparation and cytotoxic properties of antibody-toxin conjugates," Immunol Rev 62:119-158 (1982).
Vaccaro et al., "Engineering the Fc region of immunoglobulin G to modulate in vivo antibody levels," Nat Biotechnol 23(10):1283-1288 (2005).
Vajdos et al., "Comprehensive Functional Maps of the Antigen-binding Site of an Anti-ErbB2 Antibody Obtained with Shotgun Scanning Mutagenesis," J Mol Biol 320:415-428 (2002).
Van Der Stegen et al., "The pharmacology of second-generation chimeric antigen receptors," Nat Rev Drug Discov 14:499-509 (2015).
Vaughan et al., "Human antibodies by design," Nat Biotechnol 16(6):535-539 (1998).
Veri et al., "Therapeutic Control of B Cell Activation via a Recruitment of Fcγ Receptor IIB (CD32B) Inhibitory Function with a Novel Bispecific Antibody Scaffold," Arthritis Rheum 62(7):1933-1943 (2010).
Verma et al., "Antibody engineering: comparison of bacterial, yeast, insect and mammalian expression systems," J Immunol Methods 216:165-181 (1998).
Waldemann et al, "Metabolism of immunoglobulins," Prog Allergy 13:1-110 (1969).
Walker et al., "CD22: an inhibitory enigma," Immunology 123(3):314-325 (2008).
Wang et al., "Antibody Engineering Using Phage Display with a Coiled-Coil Heterodimeric Fv Antibody Fragment," PLoS One 6(4):e19023 (2011).
Wienands, "The B-cell antigen receptor: formation of signaling complexes and the function of adaptor proteins," Curr Top Microbiol Immunol 245:53-76 (2000).
Willcox et al., "Production of soluble αβ T-cell receptor heterodimers suitable for biophysical analysis of ligand binding," Protein Sci 8:2418-2423 (1999).
Winkler et al., "Changing the Antigen Binding Specificity by Single Point Mutations of an Anti-p24 (HIV-1) Antibody," J Immunol 165:4505-4514 (2000).
Wu et al., "Humanization of a Murine Monoclonal Antibody by Simultaneous Optimization of Framework and CDR Residues," J Mol Biol 294:151-162 (1999).
Yang et al., "CDR walking mutagenesis for the affinity maturation of a potent human anti-HIV-1 antibody into the picomolar range," J Mol Biol 254(3):392-403 (1995).

Young et al., "Thermal stabilization of a single-chain Fv antibody fragment by introduction of a disulphide bond," FEBS Lett 377(2):135-139 (1995).
Yu et al., "Interaction between Bevacizumab and Murine VEGF-A: A Reassessment," Invest Ophthalmol Vis Sci 49(2):522-527 (2008).
Yu et al., "Rationalization and Design of the Complementarity Determining Region Sequences in an Antibody-Antigen Recognition Surface," PLOS One 7(3):e33340 (2012).
Zahnd et al., "Directed in Vitro Evolution and Crystallographic Analysis of a Peptide-binding Single Chain Antibody Fragment (scFv) with Low Picomolar Affinity," J Biol Chem 279(18):18870-18877 (2004).
Zhang et al., "PowerBLAST: a new network BLAST application for interactive or automated sequence analysis and annotation," Genome Res 7(6):649-656 (1997).
Zhu et al., "Remodeling domain interfaces to enhance heterodimer formation," Protein Sci 6(4):781-788 (1997).
International Search Report issued in PCT/EP2016/079444, dated Feb. 27, 2017.
Hernández-Molina et al., "The meaning of anti-Ro and anti-La antibodies in primary Sjögren's syndrome," Autoimmunity Reviews 10:123-125 (2011).
Lloyd et al., "Modelling the human immune response: performance of a $10^{11}$ human antibody repertoire against a broad panel of therapeutically relevant antigens," Protein Engineering, Design & Selection 22(3):159-168 (2009).
Edwards et al., "The Remarkable Flexibility of the Human Antibody Repertoire; Isolation of Over One Thousand Different Antibodies to a Single Protein, BLyS," J Mol Biol 334:103-118 (2003).
Non-Final Rejection issued in U.S. Appl. No. 15/779,424 dated Nov. 25, 2019.
Non-Final Rejection issued in U.S. Appl. No. 15/779,426 dated Jan. 28, 2020.
Non-Final Rejection issued in U.S. Appl. No. 15/779,421 dated Sep. 5, 2019.
Notice of Allowance issued in U.S. Appl. No. 15/779,421 dated Feb. 11, 2020.
Notice of Allowance in U.S. Appl. No. 15/779,424 dated Apr. 24, 2020.
Chang et al., "The Dock and Lock Method: A Novel Platform Technology for Building Multivalent, Multifunctional Structures of Defined Composition with Retained Bioactivity," Clin Cancer Res 13 (18 Suppl): 5586s-5591s (2007).
Kumar et al., "Molecular Cloning and Expression of the Fabs of Human Autoantibodies in Escherichia coli," J Biol. Chem. 275(45): 35129-35136 (2000).
Polson et al., "Antibody-drug Conjugates Targeted to CD79 for the Treatment of Non-Hodgkin Lymphoma," Blood 110(2): 616-623 (2007).
Smith-Gill et al., "Contributions of Immunoglobulin Heavy and Light Chains to Antibody Specificity for Lysozyme and Two Haptens," the Journal of Immunology 139(12): 4135-4144 (1987).
Snyder et al., "Overview of Monoclonal Antibodies and Small Molecules Targeting the Epidermal Growth Factor Receptor Pathway in Colorectal Cancer," Clin Colorec Canc 5 (Suppl.2): S71-S80 (2005).
Song et al., "Light Chain of Natural Antibody Plays a Dominant Role in Protein Antigen Binding," Biochem. Biophys Res. Comm. 268: 390-394 (2000).
Notice of Allowance in U.S. Appl. No. 15/779,426 dated Jul. 2, 2020.
Non-final Office Action in U.S. Appl. No. 15/779,417 dated Jul. 7, 2020.
Beiboer et al., "Guided Selection of a Pan Carcinoma Specific Antibody Reveals Similar Binding Characteristics Yet Structural Divergence Between the Original Murine Antibody and its Human Equivalent," J. Mol. Biol. 296:833-849 (2000).
Bendig, "Humanization of Rodent Monoclonal Antibodies by CDR Grafting," Methods: A Companion to Methods in Enzymology 8:83-93 (1995).
Klimka et al., "Human anti-CD30 recombinant antibodies by guided phage antibody selection using cell panning," British Journal of Cancer, 83(2):252-260 (2000).

(56) References Cited

OTHER PUBLICATIONS

Munodzana et al., "Conformational Dependence of *Anaplasma marginale* Major Surface Protein 5 Surface-Exposed B-Cell Epitopes," Infection and Immunity, American Society for Microbiology 66(6):2619-2624 (1998).

Paul, "Fundamental Immunology: Structure and Function of Immunogloblins", Third Edition, Chapter 9, pp. 292-295, (1993).

Polyak et al., "Blood: Alanine-170 and proline-172 are critical determinants for extra cellular CD20 epitopes; heterogeneity in the fine specificity of CD20 monoclonal antibodies is defined by additional requirements imposed by both amino acid sequence and quaternary structure," Blood Journal 99:3256-3262 (2002).

Portolano et al., "Lack of Promiscuity in Autoantigen-Specific H and L Chain Combinations as Revealed by Human H and L Chain Roulette", the Journal of Immunology, 150(3):80-887 (1993).

Altin et al., "The role of CD45 and CD45-associated molecules in T cell activation," Immunol. Cell Biol. 75: 430-445, (1997).

Li et al. "Study advance in molecular structure and function of CD45," Intl J. Immunology, 31(5):346-349 (2008).

Biolegend Data Sheet, FITC anti-mouse CD45.1 Antibody, (1), (Nov. 30, 2012).

Xiao Foreign Medical Sciences, China Academic Journal Electronic Publishing House, (Section of Internal Medicine), 31(3):93-96 (2004).

Office Action dated Nov. 4, 2020 in Chinese Patent Application No. 201680041760.4 (with English translation only).

Wang et al., "Molecular Mechanisms of Burkitt's Lymphoma treated by Epratuzumab," Modern Oncology 19(11): 2188-2190 (2011).

Zhu et al., "Expression of CD22 and CD79b from patients with chronic lymphocytic leukemia," J Clin Hematol, (China), 667-669, (Oct. 26, 2013).

Hoeller et al., "CD79a and Cycline are the most appropriate markers to discriminiate classical Hodgkin's Lymphoma from Primary Mediastinal Large B-cell Lymphoma Histopathology," J. Clin Exp Pathol. 56(2): 217-228 (2010).

Final Office Action dated Dec. 30, 2020, in U.S. Appl. No. 15/779,417.

Hu, Shi et al., "Four-in-One Antibodies Have Superior Cancer Inhibitory Activity Against EGFR, HER2, HER3, and VEGF through Disruption of HER/MET Crosstalk," Cancer Res. 75(1): 159-70 (2015).

\* cited by examiner

METHOD EMPLOYING BISPECIFIC PROTEIN COMPLEX

REFERENCE TO AN ELECTRONIC SEQUENCE LISTING

The contents of the electronic sequence listing (00890019US1seqlist.txt; Size: 92 KB; and Date of Creation May 22, 2018) is herein incorporated by reference in its entirety.

FIELD OF INVENTION

The present disclosure relates to a method of controlling and directing cells, for example to stimulate an immune response, inhibit an immune response or direct tissue regeneration for therapeutic activity.

BACKGROUND OF INVENTION

Bispecific antibodies can be used to re-direct a patients cells in vivo: this has been most widely used to target T cells in cancer (Muller et al BioDrugs (2010): 24, 89-98). Due to the complexity of generating these molecules, this has largely been limited to a few combinations.

Another method being used to re-direct cells in vivo is the transduction of T cells with chimeric antigen receptors (CAR-T cells) and then transferring these cells into the patient (Nat. Revs. Drug Disc. 2015. 14. 499-509). The complexity of generation of optimal constructs and scope for serious side-effects limits its application to serious disease such as cancer.

There exists a need to be able to flexibly generate many different molecules and options in a modular way to re-direct cells by multiple mechanisms such as:—
1) transduction of targeting and signalling molecules to adoptively transferred cells such as the CAR-T approach;
2) transduction of targeting molecules alone to adoptively transferred cells; and
3) in vivo targeting cells like the bispecific antibody approach.

A modular bispecific antibody approach (comprising two single chain Fvs) was also employed with one binding domain specific to CD3 on T cells and the other binding domain specific to a peptide E5B9. The scFv specific to E5B9 is used to direct the T cells to a tumor cell. A fusion protein comprising a scFv specific to CD33 and the peptide E5B9 binds CD33 on the surface of the tumor cell. The peptide E5B9 is then available to bind the scFv of the bispecific on the T cells resulting in retargeting of the same to the tumor cell. (Arndt et al in Leukemia (2014) 28, 59-69).

The peptide E5B9 is derived from La/SS-antigen. Anti-La/SS-B autoantibodies were described originally as precipitating autoantibodies in sera of Sjogren's Syndrome patients and referred to as SjT. Autoantibodies against La/SS-B are also commonly found in Systemic Lupus Erythematosus and Subacute Cutaneous Lupus.

Thus there may be a risk that the use of the E5B9 peptide/targeting molecule could be limited by pre-existing autoantibodies.

A modular method to deliver engrafted cell specificity utilising CD16 to capture IgG targeting specificities has been reported (Cancer Res 2013 74 (1) 93-103). However the CD16 specificity of the effector cells can bind any human IgG and could bind to autoantibodies in vivo and hence target the engrafted T cells to self-antigens and self-tissues generating acute autoimmunity.

Other approaches being developed in the art for retargeting also have potential deleterious effects, for example the generation of autoantibodies or stimulation of cytokine storm. Thus whilst the retargeting concept is useful, all of the current approaches have the potential to stimulate serious off-target effects.

The present method seeks to address these issues in one or more ways.

SUMMARY OF INVENTION

The present invention addresses the issues above by providing a method of introducing heterodimerically-tethered bispecific protein complexes to a cell so that retargeting can occur. It can be applied directly to patients to direct cells in vivo or can be utilised in the adoptive transfer of cells into patients and is potentially applicable for many disease indications, including but not limited to cancer.

The present invention additionally facilitates the generation of a large number of different combinations of heterodimerically-tethered bispecific protein complexes, screening and identification of the optimal combinations for cell re-targeting and function or utilisation of cell trafficking to deliver an antibody cargo.

There is provided a method employing a heterodimerically-tethered bispecific protein complex of formula A-X:Y-B, wherein:
A-X is a first fusion protein;
Y-B is a second fusion protein;
X:Y is a heterodimeric-tether;
: is a binding interaction between X and Y;
A is a first protein component of the bispecific protein complex selected from an antibody or binding fragment thereof, a protein ligand; one or more components of a cell surface protein or a complex thereof or combinations thereof
B is a second protein component of the bispecific protein complex selected from an antibody or binding fragment or an antigen (including for example a protein ligand),
X is a first binding partner of a binding pair independently selected from an antigen or an antibody or binding fragment thereof; and
Y is a second binding partner of the binding pair independently selected from an antigen or an antibody or a binding fragment thereof;
wherein A presents X on the surface of a cell, and
B is specific to an epitope on target cell or tissue of interest,
with the proviso that when X is an antigen Y is an antibody or binding fragment thereof specific to the antigen represented by X and when Y is an antigen X is an antibody or binding fragment thereof specific to the antigen represented by Y, said method comprising the steps of introducing:
  i. a combination of the fusion proteins A-X and B-Y in an uncomplexed form, or
  ii. A-X:Y-B in a heterodimerically-tethered bispecific protein complex form, to a population of cells.

Within the present disclosure, the fusion proteins' terms "A-X" and "Y-B" may be analogously indicated as "X-A" or "B-Y". The same applies to term for the heterodimeric-tether "X:Y" which can also be indicated herein as "Y:X".

In one example the present invention provides a method employing a heterodimerically-tethered bispecific protein complex of formula A-X:Y-B, wherein:

A-X is a first fusion protein;
Y-B is a second fusion protein;
X:Y is a heterodimeric-tether;
: is a binding interaction between X and Y;
A is a first protein component of the bispecific protein complex comprising a transmembrane domain and optionally further comprising a spacer region, preferably at the N-terminal, and/or a C-terminal intracellular signalling region,
B is a second protein component of the bispecific protein complex selected from an antibody or binding fragment or an antigen (including for example a protein ligand),
X is a first binding partner of a binding pair independently selected from an antigen or an antibody or binding fragment thereof; and
Y is a second binding partner of the binding pair independently selected from an antigen or an antibody or a binding fragment thereof;
wherein A-X is expressed on the surface of an effector cell, and
B specifically binds a target cell,
with the proviso that when X is an antigen Y is an antibody or binding fragment thereof specific to the antigen represented by X and when Y is an antigen X is an antibody or binding fragment thereof specific to the antigen represented by Y, said method comprising the steps of introducing:
  i. a combination of the fusion proteins A-X and B-Y in an uncomplexed form, or
  ii. A-X:Y-B in a heterodimerically-tethered bispecific protein complex form, or
  iii. a nucleic acid encoding the fusion protein A-X and optionally a nucleic acid encoding the fusion protein B-Y, or
  iv. the fusion protein B-Y and a nucleic acid encoding the fusion protein A-X, or
  v. an effector cell expressing A-X, where X is presented on the surface of the cell and fusion protein B-Y
to a population of cells.

In one example the present invention provides a method employing a heterodimerically-tethered bispecific protein complex of formula A-X:Y-B, wherein:
A-X is a first fusion protein;
Y-B is a second fusion protein;
X:Y is a heterodimeric-tether;
: is a binding interaction between X and Y;
A is a first protein component of the bispecific protein complex selected from an antibody or binding fragment thereof, and a protein (including for example an antigen, such as a protein ligand);
B is a second protein component of the bispecific protein complex selected from an antibody or binding fragment or an antigen (including for example a protein ligand),
X is a first binding partner of a binding pair independently selected from a non-mammalian antigen or an antibody or binding fragment thereof; and
Y is a second binding partner of the binding pair independently selected from a non-mammalian antigen or an antibody or a binding fragment thereof;
wherein A specifically binds a protein (including a marker) expressed on the surface of an effector cell, and
B specifically binds a target cell,
with the proviso that when X is an antigen Y is an antibody or binding fragment thereof specific to the antigen represented by X and when Y is an antigen X is an antibody or binding fragment thereof specific to the antigen represented by Y, said method comprising the steps of introducing:
  i. a combination of the fusion proteins A-X and B-Y in an uncomplexed form, or
  ii. A-X:Y-B in a heterodimerically-tethered bispecific protein complex form,
to a population of cells.

In one example the present invention provides a method employing a heterodimerically-tethered bispecific protein complex of formula A-X:Y-B, wherein:
A-X is a first fusion protein;
Y-B is a second fusion protein;
X:Y is a heterodimeric-tether;
: is a binding interaction between X and Y;
A is a first protein component of the bispecific protein complex selected from an antibody or binding fragment thereof, and a protein (including for example an antigen, such as a protein ligand);
B is a second protein component of the bispecific protein complex selected from an antibody or binding fragment or an antigen (including for example a protein ligand),
X is a first binding partner of a binding pair independently selected from an antigen or an antibody or binding fragment thereof; and
Y is a second binding partner of the binding pair independently selected from an antigen or an antibody or a binding fragment thereof;
wherein A specifically binds a protein (including a marker) expressed on the surface of an effector cell, and
B specifically binds a target cell,
with the proviso that there are no more than two scFvs in the bispecific complex and when X is an antigen Y is an antibody or binding fragment thereof specific to the antigen represented by X and when Y is an antigen X is an antibody or binding fragment thereof specific to the antigen represented by Y, said method comprising the steps of introducing:
  i. a combination of the fusion proteins A-X and B-Y in an uncomplexed form, or
  ii. A-X:Y-B in a heterodimerically-tethered bispecific protein complex form,
to a population of cells.

The method may be performed in vitro, ex vivo on a sample obtained from a patient, such as a blood sample or tissue sample or in vitro cultured cells, or in vivo.

Thus the present disclosure provides method employing a heterodimerically-tethered bispecific protein complex of formula A-X:Y-B, wherein:
A-X is a first fusion protein;
Y-B is a second fusion protein;
X:Y is a heterodimeric-tether;
: is a binding interaction between X and Y;
A is a first protein component of the bispecific protein complex selected from an antibody or binding fragment thereof, a protein ligand; one or more components of a cell surface protein or a complex thereof or combinations thereof;
B is a second protein component of the bispecific protein complex selected from an antibody or binding fragment or an antigen (including for example a protein ligand),
X is a first binding partner of a binding pair independently selected from an antigen, a non-mammalian antigen or an antibody or binding fragment thereof; and
Y is a second binding partner of the binding pair independently selected from an antigen, a non-mammalian antigen or an antibody or a binding fragment thereof;

wherein A presents X on the surface of a cell, and
B is specific to an epitope on target cell or tissue of interest,
with the proviso that when X is an antigen Y is an antibody or binding fragment thereof specific to the antigen represented by X and when Y is an antigen X is an antibody or binding fragment thereof specific to the antigen represented by Y, said method comprising the steps of administering a therapeutically effective amount of:
i. a combination of the fusion proteins A-X and B-Y in an uncomplexed form, or
ii. A-X:Y-B in a heterodimerically-tethered bispecific protein complex form, to a patient in need thereof (i.e. the population of cells is in vivo).

In particular, the method according to the invention are for trafficking cells (e.g. re-targeting cells or directing adoptive cells) and/or for use of cell trafficking to deliver an antibody or a fragment thereof.

Thus in one example there is provided use of a A-X, B-Y, a combination of A-X and B-Y and a complex of A-X:Y-B for use in treatment or prophylaxis.

Thus in one example there is provided use of a A-X, B-Y, a combination of A-X and B-Y and a complex of A-X:Y-B for use in the manufacture of a medicament, in particular for a disease or condition disclosed herein.

Thus in one example there is provided use of an effector cell expressing A-X on its surface for use in treatment or prophylaxis.

Thus in one example there is provided use of an effector cell expressing A-X on its surface for use in the manufacture of a medicament, in particular for a disease or condition disclosed herein.

Thus in one example there is provided use of an effector cell expressing A-X on its surface in combination with B-Y for use in treatment or prophylaxis.

Thus in one aspect there is provided use of an effector cell expressing A-X on its surface in combination with B-Y for use in the manufacture of a medicament, in particular for disease or condition disclosed herein.

In one example the present invention provides an effector cell expressing X or A-X on its surface.

In one embodiment X or Y is specific to the peptide GCN4 or a fragment thereof as shown in SEQ ID NO: 1 or amino acids 1-38 of SEQ ID NO: 1 in Table 1, wherein the amino acids in bold are optional and the amino acids in italics are the sequence of the linker. The nucleotide sequence encoding the GCN4 peptide according to SEQ ID NO: 1 is shown in SEQ ID NO: 2.

TABLE 1

| | |
|---|---|
| GCN4 (7P14P) SEQ ID NO: 1 | *ASGGG*RMKQLEPKVEELLPKNYHLENEVARLKKLVGERHHHHHH |
| GCN4 (7P14P) SEQ ID NO: 2 | GCTAGCGGAGGCGGAAGAATGAAACAACTTGAACCCAAGGTTGAAGAATTGCTT CCGAAAAATTATCACTTGGAAAATGAGGTTGCCAGATTAAAGAAATTAGTTGGC GAACGCCATCACCATCACCATCAC |
| 52SR4 ds scFv SEQ ID NO: 3 | DAVVTQESALTSSPGETVTLTCRSSTGAVTTSNYASWVQEKPDHLFTGLIGGTN NRAPGVPARFSGSLIGDKAALTITGAQTEDEAIYFCVLWYSDHWVFGCGTKLTV LGGGGGSGGGGSGGGGSGGGGSDVQLQQSGPGLVAPSQSLSITCTVSGFLLTDY GVNWVRQSPGKCLEWLGVIWGDGITDYNSALKSRLSVTKDNSKSQVFLKMNSLQ SGDSARYYCVTGLFDYWGQGTTLTVSSAAAHHHHHHEQKLISEEDL |
| 52SR4 ds scFv SEQ ID NO: 4 | GATGCGGTGGTGACCCAGGAAAGCGCGCTGACCAGCAGCCCGGGCGAAACCGTG ACCCTGACCTGCCGCAGCAGCACCGGCGCGGTGACCACCAGCAACTATGCGAGC TGGGTGCAGGAAAAACCGGATCATCTGTTTACCGGCCTGATTGGCGGCACCAAC AACCGCGCGCCGGGCGTGCCGGCGCGCTTTAGCGGCAGCCTGATTGGCGATAAA GCGGCGCTGACCATTACCGGCGCGCAGACCGAAGATGAAGCGATTTATTTTTGC GTGCTGTGGTATAGCGACCATTGGGTGTTTGGCTGCGGCACCAAACTGACCGTG CTGGGTGGAGGCGGTGGCTCAGGCGGAGGTGGCTCAGGCGGTGGCGGGTCTGGC GGCGGCGGCAGCGATGTGCAGCTGCAGCAGAGCGGCCCGGGCCTGGTGGCGCCG AGCCAGAGCCTGAGCATTACCTGCACCGTGAGCGGCTTTCTCCTGACCGATTAT GGCGTGAACTGGGTGCGCCAGAGCCCGGGCAAATGCCTGGAATGGCTGGGCGTG ATTTGGGGCGATGGCATTACCGATTATAACAGCGCGCTGAAAAGCCGCCTGAGC GTGACCAAAGATAACAGCAAAAGCCAGGTGTTTCTGAAAATGAACAGCCTGCAG AGCGGCGATAGCGCGCGCTATTATTGCGTGACCGGCCTGTTTGATTATTGGGGC CAGGGCACCACCCTGACCGTGAGCAGCGCGGCCGCCCATCACCATCACCATCAC GAACAGAAACTGATTAGCGAAGAAGATCTGTAATAG |
| SEQ ID NO: 99 | DAVVTQESALTSSPGETVTLTCRSSTGAVTTSNYASWVQEKPDHLFTGLIGGTN NRAPGVPARFSGSLIGDKAALTITGAQTEDEAIYFCVLWYSDHWVFGCGTKLTV LGGGGSGGGGSGGGGSGGGGSDVQLQQSGPGLVAPSQSLSITCTVSGFLLTDY GVNWVRQSPGKCLEWLGVIWGDGITDYNSALKSRLSVTKDNSKSQVFLKMNSLQ SGDSARYYCVTGLFDYWGQGTTLTVSS |
| SEQ ID NO: 100 | DVQLQQSGPGLVAPSQSLSITCTVSGFLLTDYGVNWVRQSPGKCLEWLGVIWGD GITDYNSALKSRLSVTKDNSKSQVFLKMNSLQSGDSARYYCVTGLFDYWGQGTT LTVSSPARFSGSLIGDKAALTITGAQTEDEAIYFCVLWYSDHWVFGCGTKLTVL GGGGGSGGGGSGGGGSGGGGSDAVVTQESALTSSPGETVTLTCRSSTGAVTTSN YASWVQEKPDHLFTGLIGGTNNRAPGVPARFSGSLIGDKAALTITGAQTEDEAI YFCVLWYSDHWVFGCGTKLTVL |
| SEQ ID NO: 101 | MSVPTQVLGLLLLWLTDARC |
| SEQ ID NO: 102 | MEWSWVFLFFLSVTTGVHS |

TABLE 1-continued

| SEQ ID NO: 103 | MDWLWTLLFLMAAAQSAQA |
| --- | --- |
| SEQ ID NO: 104 | MGWSWTFLFLLSGTSGVLS |

In one embodiment one of X or Y is a full-length antibody, a Fab fragment, a Fab' fragment, VHH or a scFv and the other is a peptide, for example scFv or sdAb, such as the scFv 52SR4 (SEQ ID NOs: 3, 99 or 100 or amino acids 1-243 of SEQ ID NO: 3 as shown in Table 1). Thus in one embodiment one of X or Y is a peptide, for example in the range 5 to 25 amino acids in length, for example the peptide is 5, 6, 7, 8, 9, 10, 11, 12, 13, 14, 15, 16, 17, 18, 19, 20, 21, 22, 23, 24 or 25 amino acids in length.

In one embodiment where at least one of X and Y is an antigen/peptide it is a non-mammalian antigen/peptide for which there is no corresponding mammalian antigen or peptide with a similar or identical sequence, in particular no corresponding human sequence.

In one embodiment the antigen (including a peptide) employed in X or Y has low immunogenicity (i.e. does not stimulate a strong antibody response when administered (in vivo).

In one embodiment one of X or Y is a peptide GCN4 or a fragment thereof (SEQ ID NO: 1 or amino acids 1-38 of SEQ ID NO: 1). Other variations of the GCN4 peptides are shown in Table 2, wherein the amino acids in bold are optional and the amino acids in italics form the sequence of the linker.

Advantageously, this peptide is from yeast and has no counterpart in mammalian (in particular human) proteins or peptides. Furthermore it can bind a scFv, such as 52SR4 with high affinity. Furthermore, it is not highly immunogenic in vivo.

TABLE 2

| SEQ ID NO: 76 | *GGGGSGGGGSGGGGSGGGGSGGGGS*YHLENEVARLKKLVGERHHHHHH |
| --- | --- |
| SEQ ID NO: 77 | *GGGGSGGGGSGGGGSGGGGSGGGGS*YHLENEVARLKALVGERHHHHHH |
| SEQ ID NO: 78 | *GGGGSGGGGSGGGGSGGGGSGGGGS*YHLENEVARLAKLVGERHHHHHH |
| SEQ ID NO: 79 | *GGGGSGGGGSGGGGSGGGGSGGGGS*YHLENEVARLQKLVGERHHHHHH |
| SEQ ID NO: 80 | *GGGGSGGGGSGGGGSGGGGSGGGGS*YHLENEVARLNKLVGERHHHHHH |
| SEQ ID NO: 81 | *GGGGSGGGGSGGGGSGGGGSGGGGS*YHLENEVARLAALVGERHHHHHH |
| SEQ ID NO: 82 | *GGGGSGGGGSGGGGSGGGGSGGGGS*YHLENEVARLQALVGERHHHHHH |
| SEQ ID NO: 83 | *GGGGSGGGGSGGGGSGGGGSGGGGS*YHLENEVARLNALVGERHHHHHH |
| SEQ ID NO: 84 | *ASGGG*AMKQLEPKVEELLPKNYHLENEVARLKKLVGERHHHHHH |
| SEQ ID NO: 85 | *ASGGG*RMKQLEPKVEELLPKNYHLENEVARLKALVGERHHHHHH |
| SEQ ID NO: 86 | *ASGGG*AMKQLEPKVEELLPKNYHLENEVARLKALVGERHHHHHH |
| SEQ ID NO: 87 | *ASGGG*RMKQLEPKVEELLPKNYHLENEVARLAKLVGERHHHHHH |
| SEQ ID NO: 88 | *ASGGG*RMKQLEPKVEELLPKNYHLENEVARLQKLVGERHHHHHH |
| SEQ ID NO: 89 | *ASGGG*RMKQLEPKVEELLPKNYHLENEVARLNKLVGERHHHHHH |
| SEQ ID NO: 90 | *ASGGG*AMKQLEPKVEELLPKNYHLENEVARLAKLVGERHHHHHH |
| SEQ ID NO: 91 | *ASGGG*AMKQLEPKVEELLPKNYHLENEVARLQKLVGERHHHHHH |
| SEQ ID NO: 92 | *ASGGG*AMKQLEPKVEELLPKNYHLENEVARLNKLVGERHHHHHH |
| SEQ ID NO: 93 | *ASGGG*RMKQLEPKVEELLPKNYHLENEVARLAALVGERHHHHHH |
| SEQ ID NO: 94 | *ASGGG*RMKQLEPKVEELLPKNYHLENEVARLQALVGERHHHHHH |
| SEQ ID NO: 95 | *ASGGG*RMKQLEPKVEELLPKNYHLENEVARLNALVGERHHHHHH |
| SEQ ID NO: 96 | *ASGGG*AMKQLEPKVEELLPKNYHLENEVARLAALVGERHHHHHH |
| SEQ ID NO: 97 | *ASGGG*AMKQLEPKVEELLPKNYHLENEVARLQALVGERHHHHHH |
| SEQ ID NO: 98 | *ASGGG*AMKQLEPKVEELLPKNYHLENEVARLNALVGERHHHHHH |

It should be understood that A-X and Y-B fusions may be generated in various orientations which means that the polynucleotide constructs encoding such fusion may be designed to express X or A in both orientations. The same applies to the Y-B fusion. In other words, A and B may be expressed as fused to the C-terminus of X and Y, respectively, or X and Y may be expressed as fused to the C-terminus of A and B, respectively. Irrespective of whether A, X, Y or B is at the N-terminal of the fusion, the polynucleotide sequence to generate such fusion will comprise a nucleotide sequence designed to encode a signal sequence which assists the fusions targeting to extracellular release and is ultimately cleaved from the mature fusion. Preferred signal sequences are shown in Table 1 with SEQ ID NOs: 101 to 104.

In one embodiment the method provides a high affinity interaction between fusion protein A-X and B-Y to direct an effector cell expressing A-X itself or the binding partner for A to a target antigen which is the binding partner for B with B-Y via the interaction between X and Y which forms a heterodimeric tether X:Y.

In one embodiment the binding affinity between X and Y is 5 nM or stronger, for example the binding affinity between X and Y is 900 pM or stronger, such as 800, 700, 600, 500, 400 or 300 pM.

In one embodiment A is expressed on an effector cell, for example by transfecting the cell with A-X such that at least X is expressed on the surface of the cell. In this particular embodiment, the signal sequence will be at N-terminal of X and A will be at the C-terminal of X (signal sequence-X-A).

In one embodiment the A is specific for a protein on the surface of an effector cell.

In both these embodiments A facilitates the cell surface presentation of X to form a heterodimeric tether with Y which is fused to B.

Where A presents X on the surface of an effector cell, such as a T cell, a population of for example T cells is selected then the following may be introduced ex vivo:
A-X as a fusion protein, or
transfection of a polynucleotide sequence, for example a DNA sequence (such as a vector) encoding A-X suitable for expressing at least X on the surface of the cell.

Alternatively where A presents X on the surface of an effector cell, such as a T cell, a population of for example T cells is selected then the following may be introduced in vivo or ex vivo:
A-X as a fusion protein,
a polynucleotide sequence, for example a DNA sequence (such as a vector) encoding A-X suitable for expressing at least X on the surface of the cell, optionally in combination with a suitable carrier.

A 'population of cells' as used herein may be a population of cells in vitro or in vivo and may contain a mixture of one or more cell types.

X may be presented on the surface of the effector cell by incorporating in A, for example, a sequence of a transmembrane domain, optionally adjoined through a spacer region.

In one embodiment the transmembrane domain is natural or from a synthetic source, such as where the natural source is a membrane bound protein, transmembrane protein or a functional fragment thereof, for example the transmembrane domain comprises at a transmembrane region or regions of a protein selected from the group including the alpha, or beta chain of the T-cell receptor, CD28, CD3 epsilon, CD45, CD4, CD5, CD8, CD9, CD16, CD22, CD33, CD37, CD64, CD80, CD86, CD134, CD137, ICOS and CD154.

Alternatively the transmembrane domain may be synthetic, in which case it will comprise predominantly hydrophobic residues such as leucine and valine, for example a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signalling domain of the chimeric receptor. A glycine-serine doublet provides a particularly suitable linker.

The A component may additionally comprise a spacer region which enables A to present X in a biologically relevant orientation on the cell surface for engagement with Y on the target cell.

When A is expressed on the surface of an effector cell it may further comprise a spacer region, for example the spacer domain from a protein naturally expressed on a cell, such as a surface expressed immunoglobulin, in particular, a spacer region derived from a protein selected from the group comprising CD28, CD4, CD8, MHC, hinge, CH2 and CH3 region of human IgG1 and the hinge region of human IgG1 combined with an extracellular domain of human CD28.

The spacer domain or region may be the domain between a transmembrane domain and a ligand binding domain in a naturally occurring cell surface expressed protein, or a derivative or variant thereof.

Preferred embodiments of such X-A fusions which are in the orientation N to C terminus X-A (linker-transmembrane region) are shown in Table 3 (SEQ ID NOs:105-108).

When A is expressed on the surface of an effector cell in one embodiment A is operably connected to an intra-cellular signalling domain.

Thus in one embodiment the effector cell is provided with additional or enhanced cellular activity by transfection with A-X whereby A comprises a transmembrane region and one or more signalling regions.

Preferred embodiments of such X-A fusions (X-A-linker-transmembrane region-intracellular signalling sequence) are shown in Table 3 (SEQ ID NOs: 109-116) where the amino acids in italic are the spacer, the amino acids underlined are the transmembrane region and the amino acids in bold are the intracellular signalling peptide. More preferably, such fusions are expressed with a signal peptide sequence, such as, but not limited to, those shown in SEQ ID NO: 101 to 104.

TABLE 3

| | |
|---|---|
| SEQ ID NO: 105 | DAVVTQESALTSSPGETVTLTCRSSTGAVTTSNYASWVQEKPDHLFTGLIGGTNNRAPGVP ARFSGSLIGDKAALTITGAQTEDEATYFCVLWYSDHWVFGCGTKLTVLGGGGSGGGGSGG GGSGGGGSDVQLQQSGPGLVAPSQSLSITCTVSGFLLTDYGVNWVRQSPGKCLEWLGVIWG DGITDYNSALKSRLSVTKDNSKSQVFLKMNSLQSGDSARYYCVTGLFDYWGQGTTLTVSS *TSDKTHTCPPCPKGKHLCPSPLFPGPSKP*<u>LDPKFTNVLVVVGGVLACYSLLVTVAF IIFWVTRGS</u> |
| SEQ ID NO: 106 | DAVVTQESALTSSPGETVTLTCRSSTGAVTTSNYASWVQEKPDHLFTGLIGGTNNRAPGVP ARFSGSLIGDKAALTITGAQTEDEAIYFCVLWYSDHWVFGCGTKLTVLGGGGSGGGGSGG GGSGGGGSDVQLQQSGPGLVAPSQSLSITCTVSGFLLTDYGVNWVRQSPGKCLEWLGVIWG DGITDYNSALKSRLSVTKDNSKSQVFLKMNSLQSGDSARYYCVTGLFDYWGQGTT *LTVSSTSDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYKCKV* |

TABLE 3-continued

| | |
|---|---|
| | *SNKALPAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSVMHEALH NHYTQKSLSLSPGK*<u>LDPKFWVLVVVGGVLACYSLLVTVAFIIFWVTRGS</u> |
| SEQ ID NO: 107 | DVQLQQSGPGLVAPSQSLSITCTVSGFLLTDYGVNWVRQSPGKCLEWLGVIWDGITDYNS ALKSRLSVTKDNSKSQVFLKMNSLQSGDSARYYCVTGLFDYWGQGTTLTVSSPARFSGSLI GDKAALTITGAQTEDEAIYFCVLWYSDHWVFGCGTKLTVLGGGGSGGGGSGGGGSGGGGS DAVVTQESALTSSPGETVTLTCRSSTGAVTTSNYASWVQEKPDHLFTGLIGGTNNRAPGVP ARFSGSLIGDKAALTITGAQTEDEAIYFCVLWYSDHWVFGCGTKLTVL*TSDKTHTCPPCPK GKHLCPSPLFPGPSK*<u>LDPKFWVLVVVGGVLACYSLLVTVAFIIFWVTRGS</u> |
| SEQ ID NO: 108 | DVQLQQSGPGLVAPSQSLSITCTVSGFLLTDYGVNWVRQSPGKCLEWLGVIWDGITDYNS ALKSRLSVTKDNSKSQVFLKMNSLQSGDSARYYCVTGLFDYWGQGTTLTVSSPARFSGSLI GDKAALTITGAQTEDEAIYFCVLWYSDHWVFGCGTKLTVLGGGGSGGGGSGGGGSGGGGS DAVVTQESALTSSPGETVTLTCRSSTGAVTTSNYASWVQEKPDHLFTGLIGGTNNRAPGVP ARFSGSLIGDKAALTITGAQTEDEAIYFCVLWYSDHWVFGCGTKLTVL*TSDKTHTCPPCP APELLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTP PVLDSDGSFFLYSKLTVDKSRWQQGNVFSCSVMHEALHNHYTQKSLSLSPGK*<u>LDP KFWVLVVVGGVLACYSLLVTVAFIIFWVTRGS</u> |
| SEQ ID NO: 109 | DAVVTQESALTSSPGETVTLTCRSSTGAVTTSNYASWVQEKPDHLFTGLIGGTNNRAPGVP ARFSGSLIGDKAALTITGAQTEDEAIYFCVLWYSDHWVFGCGTKLTVLGGGGSGGGGSGG GGSGGGGSDVQLQQSGPGLVAPSQSLSITCTVSGFLLTDYGVNWVRQSPGKCLEW LGVIWDGITDYNSALKSRLSVTKDNSKSQVFLKMNSLQSGDSARYYCVTGLFDY WGQGTTLT*VSSTSDKTHTCPPCPKGKHLCPSPLFPGPSKPLDPKFWVLVVVGGVL <u>ACYSLLVTVAFIIFWVTRGS</u>RSKRSRLLHSDYMNMTPRRPGPTRKHYQPYAPPRD FAAYRSRVKFSRSADAPAYQQGQNQLYNELNLGRREEYDVLDKRRGRDPEMGGKP RRKNPQEGLYNELQKDKMAEAYSEIGMKGERRRGKGHDGLYQGLSTATKDTYDAL HMQALPPR |
| SEQ ID NO: 110 | DAVVTQESALTSSPGETVTLTCRSSTGAVTTSNYASWVQEKPDHLFTGLIGGTNNRAPGVP ARFSGSLIGDKAALTITGAQTEDEAIYFCVLWYSDHWVFGCGTKLTVLGGGGSGGGGSGG GGSGGGGSDVQLQQSGPGLVAPSQSLSITCTVSGFLLTDYGVNWVRQSPGKCLEW LGVIWDGITDYNSALKSRLSVTKDNSKSQVFLKMNSLQSGDSARYYCVTGLFDY WGQGTTLTVSS*TSDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTCLVKGF YPSDIAVEWESNGQPENNYKTTPPVLDSDGSFFLYSKLTVDKSRWQQGNVFSCSV MHEALHNHYTQKSLSLSPGK*<u>LDPKFWVLVVVGGVLACYSLLVTVAFIIFWVTRGS</u> RSKRSRLLHSDYMNMTPRRPGPTRKHYQPYAPPRDFAAYRSRVKFSRSADAPAYQ QGQNQLYNELNLGRREEYDVLDKRRGRDPEMGGKPRRKNPQEGLYNELQKDKMAE AYSEIGMKGERRRGKGHDGLYQGLSTATKDTYDALHMQALPPR |
| SEQ ID NO: 111 | DVQLQQSGPGLVAPSQSLSITCTVSGFLLTDYGVNWVRQSPGKCLEWLGVIWDGITDYNS ALKSRLSVTKDNSKSQVFLKMNSLQSGDSARYYCVTGLFDYWGQGTTLTVSSPARFSGSLI GDKAALTITGAQTEDEAIYFCVLWYSDHWVFGCGTKLTVLGGGGSGGGGSGGGGSGGGGS DAVVTQESALTSSPGETVTLTCRSSTGAVTTSNYASWVQEKPDHLFTGLIGGTNNRAPGVP ARFSGSLIGDKAALTITGAQTEDEAIYFCVLWYSDHWVFGCGTKLTVL*TSDKTHTC PPCPKGKHLCPSPLFPGPSKPLDPKFWVLVVVGGVLACYSLLVTVAFIIFWVTRG* <u>S</u>RSKRSRLLHSDYMNMTPRRPGPTRKHYQPYAPPRDFAAYRSRVKFSRSADAPAY QQGQNQLYNELNLGRREEYDVLDKRRGRDPEMGGKPRRKNPQEGLYNELQKDKMA EAYSEIGMKGERRRGKGHDGLYQGLSTATKDTYDALHMQALPPR |
| SEQ ID NO: 112 | DVQLQQSGPGLVAPSQSLSITCTVSGFLLTDYGVNWVRQSPGKCLEWLGVIWDGITDYNS ALKSRLSVTKDNSKSQVFLKMNSLQSGDSARYYCVTGLFDYWGQGTTLTVSSPARFSGSLI GDKAALTITGAQTEDEAIYFCVLWYSDHWVFGCGTKLTVLGGGGSGGGGSGGGGSGGGGS DAVVTQESALTSSPGETVTLTCRSSTGAVTTSNYASWVQEKPDHLFTGLIGGTNNRAPGVP PARFSGSLIGDKAALTITGAQTEDEAIYFCVLWYSDHWVFGCGTKLTVL*TSDKTH TCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSLSLS PGK*<u>LDPKFWVLVVVGGVLACYSLLVTVAFIIFWVTRGS</u>RSKRSRLLHSDYMNMTP RRPGPTRKHYQPYAPPRDFAAYRSRVKFSRSADAPAYQQGQNQLYNELNLGRREE YDVLDKRRGRDPEMGGKPRRKNPQEGLYNELQKDKMAEAYSEIGMKGERRRGKGH DGLYQGLSTATKDTYDALHMQALPPR |
| SEQ ID NO: 113 | DAVVTQESALTSSPGETVTLTCRSSTGAVTTSNYASWVQEKPDHLFTGLIGGTNNRAPGVP ARFSGSLIGDKAALTITGAQTEDEAIYFCVLWYSDHWVFGCGTKLTVLGGGGSGGGGSGG GGSGGGGSDVQLQQSGPGLVAPSQSLSITCTVSGFLLTDYGVNWVRQSPGKCLEW LGVIWDGITDYNSALKSRLSVTKDNSKSQVFLKMNSLQSGDSARYYCVTGLFDY WGQGTTLTVSS*TSDKTHTCPPCPKGKHLCPSPLFPGPSKP*<u>LDPKFWVLVVVGGVL ACYSLLVTVAFIIFWVTRGS</u>KRGRKKLLYIFKQPFMRPVQTTQEEDGCSCRFPEE EEGGCELRVKFSRSADAPAYQQGQNQLYNELNLGRREEYDVLDKRRGRDPEMGGK PRRKNPQEGLYNELQKDKMAEAYSEIGMKGERRRGKGHDGLYQGLSTATKDTYDA LHMQALPPR |

TABLE 3-continued

| SEQ ID NO: 114 | DAVVTQESALTSSPGETVTLTCRSSTGAVTTSNYASWVQEKPDHLFTGLIGGTNNRAPGVP<br>ARFSGSLIGDKAALTITGAQTEDEAIYFCVLWYSDHWVFGCGTKLTVLGGGGSGGGGSGG<br>GGSGGGGSDVQLQQSGPGLVAPSQSLSITCTVSGFLLTDYGVNWVRQSPGKCLEW<br>LGVIWGDGITDYNSALKSRLSVIKDNSKSQVFLKMNSLQSGDSARYYCVTGLFDY<br>WGQGTTLTVSS*TSDKTHTCPPCPAPELLGGPSVFLFPPKPKDTLMISRTPEVTCV*<br>*VVDVSHEDPEVKFNWYVDGVEVHNAKTKPREEQYNSTYRVVSVLTVLHQDWLNGK*<br>*EYKCKVSNKALPAPIEKTISKAKGQPREPQVYTLPPSRDELTKNQVSLTCLVKGF*<br>*YPSDIAVEWESNGQPENNYKTTPPVLDSDGSFFLYSKLTVDKSRWQQGNVFSCSV*<br>*MHEALHNHYTQKSLSLSPGK*LDPKFWVLVVVGGVLACYSLLVTVAFIIFWVTRGS<br>KRGRKKLLYIFKQPFMRPVQTTQEEDGCSCRFPEEEEGGCELRVKFSRSADAPAY<br>QQGQNQLYNELNLGRREEYDVLDKRRGRDPEMGGKPRRKNPQEGLYNELQKDKMA<br>EAYSEIGMKGERRRGKGHDGLYQGLSTATKDTYDALHMQALPPR |
| --- | --- |
| SEQ ID NO: 115 | DVQLQQSGPGLVAPSQSLSITCTVSGFLLTDYGVNWVRQSPGKCLEWLGVIWGDGITDYNS<br>ALKSRLSVIKDNSKSQVFLKMNSLQSGDSARYYCVTGLFDYWGQGTTLTVSSPARFSGSLI<br>GDKAALTITGAQTEDEAIYFCVLWYSDHWVFGCGTKLTVLGGGGSGGGGSGGGGSGGGGS<br>DAVVTQESALTSSPGETVTLTCRSSTGAVTTSNYASWVQEKPDHLFTGLIGGTNNRAPGVP<br>ARFSGSLIGDKAALTITGAQTEDEAIYFCVLWYSDHWVFGCGTKLTVL*TSDKTHTCPPCPK*<br>*GKHLCPSPLFPGPSKP*LDPKFWVLVVVGGVLACYSLLVTVAFIIFWVTRGSKRGRKKLLY<br>IFKQPFMRPVQTTQEEDGCSCREPEEEEGGCELRVKFSRSADAPAYQQGQNQLYN<br>ELNLGRREEYDVLDKRRGRDPEMGGKPRRKNPQEGLYNELQKDKMAEAYSEIGMK<br>GERRRGKGHDGLYQGLSTATKDTYDALHMQALPPR |
| SEQ ID NO: 116 | DVQLQQSGPGLVAPSQSLSITCTVSGFLLTDYGVNWVRQSPGKCLEWLGVIWGDGITDYNS<br>ALKSRLSVTKDNSKSQVFLKMNSLQSGDSARYYCVTGLFDYWGQGTTLTVSSPARFSGSLI<br>GDKAALTITGAQTEDEAIYFCVLWYSDHWVFGCGTKLTVLGGGGSGGGGSGGGGSGGGGS<br>DAVVTQESALTSSPGETVTLTCRSSTGAVTTSNYASWVQEKPDHLFTGLIGGTNNRAPGV<br>PARFSGSLIGDKAALTITGAQTEDEAIYFCVLWYSDHWVFGCGTKLTVL*TSDKTH*<br>*TCPPCPAPELLGGPSVFLFPPKPKDTLMISRTPEVTCVVVDVSHEDPEVKFNWYV*<br>*DGVEVHNAKTKPREEQYNSTYRVVSVLTVLHQDWLNGKEYKCKVSNKALPAPIEK*<br>*TISKAKGQPREPQVYTLPPSRDELTKNQVSLTCLVKGFYPSDIAVEWESNGQPEN*<br>*NYKTTPPVLDSDGSFFLYSKLTVDKSRWQQGNVFSCSVMHEALHNHYTQKSLSLS*<br>*PGK*LDPKFWVLVVVGGVLACYSLLVTVAFIIFWVTRGSKRGRKKLLYIFKQPFMR<br>PVQTTQEEDGCSCREPEEEEGGCELRVKFSRSADAPAYQQGQNQLYNELNLGRRE<br>EYDVLDKRRGRDPEMGGKPRRKNPQEGLYNELQKDKMAEAYSEIGMKGERRRGKG<br>HDGLYQGLSTATKDTYDALHMQALPPR |

When A is expressed on the surface of an effector cell in one embodiment A is not connected to an intra-cellular signalling domain.

In an aspect of the disclosure X is presented on the surface of an effector cell by virtue of the fact that A binds a protein expressed on the surface of an effector cell, for example A is independently selected from a full length antibody, a Fab fragment, a Fab' fragment, a sdAb (VHH, VL, VH), a scFv, and an antigen, for example a ligand to a receptor expressed on the surface of the effector cell.

In one embodiment A binds to (is specific to) a protein expressed on the surface of the effector cell.

In one embodiment the effector cell is a cell capable of a cellular response, for example release of a soluble molecules, such as immunoglobulins, cytokines or chemokines.

Examples of effector cells may include cells capable of killing a target cell such as cytotoxic T cells (CD8 positive, granzyme positive, perform positive or granulysin positive cells), intestinal intraepithelial lymphocytes (or other similar tissue resident lymphocytes), B Cells (for example granzyme positive B cells), NK cells, NKT cells (or CD1d positive T cells), gamma delta T cells, monocytes, macrophages, dendritic cells, mast cells, neutrophils, eosinophils, basophils and platelets. These effector cells may provide their effects by multiple mechanisms such as antibody dependent cellular cytotoxicity via Fc receptor interactions, phagocytosis or cell engulfment, recruitment of complement or direct recognition activation of effector cell killing by ligating cell surface receptors. Alternatively cells can induce programmed cell death (for instance via upregulation of Fas ligand or similar death receptors) or can release cytoxic soluble mediators such as cytokines that can also kill cells.

In one embodiment A binds directly to a protein expressed on the surface of the effector cell. In one embodiment the cell protein/marker on the surface of the effector cells is from any cell surface receptor that characterises a cell set or sub-set of interest e.g. CD45, CD2, CD3, CD4, CD5, CD7, CD8, CD11b, CD11c, CD13, CD14, CD15, CD16, CD19, CD20, CD23, CD25, CD27, CD33, CD38, CD56, CD57, CD64, CD80, CD83, CD86, CD123, CD127, CD137, CD138, CD196, CD209, HLA-DR, Lin-1 to -3.

In one embodiment the protein/marker on the effector cell is a B cell marker, for example selected from the group comprising CD19, CD20, CD21, CD22, CD23, CD24, CD27, CD35, CD38, CD40, CD45 (all or specific individual isoforms), CD43, CD81, CD138, CXCR4, BCMA and IL-6R, for example CD38, CD138, CD45, CD27, CD19 or CD20, such as CD38 or CD138.

In one embodiment the protein/marker on the effector cell is a B cell marker, wherein the B cell marker is in a constant region of an antibody light chain or a constant region of an antibody heavy chain, expressed as part of an immunoglobulin on the surface of the cell, for example wherein the marker is specific to antibody isotype selected from the group comprising IgG1, IgG2, IgG3, IgG4, IgA1, IgA2, IgE and IgM.

In one embodiment the protein/marker on the effector cell is a T cell marker, for example selected from the group comprising CD2, CD3, CD4, CD5, CD6, CD7, CD8, CD25, CD127 CD196 (CCR6), CD197 (CCR7), CD62L, CD69 and CD45 (all or specific individual isoforms).

In one embodiment effector cells and antigens on effector cells that can be bound by A or used to identify cells on which A can be expressed include:—

B cell or B cell subsets antigens expressed, either as whole proteins or smaller peptides of the whole proteins, on such cells can be but are not limited to CD19, CD20, CD21, CD22, CD23, CD24, CD35, CD79a, CD79b, CD81, CD138, CD319 etc.

T cell or T cell subsets antigens expressed, either as whole proteins or smaller peptides of the whole proteins, on such cells can be but are not limited to CD2, CD3, CD4, CD5, CD6, CD7, CD8, CD28, CD152, CD154, CD160.

Normal NK cell or NK cell subsets antigens expressed, either as whole proteins or smaller peptides of the whole proteins, on such cells can be but are not limited to CD16, CD56, CD96, CD158, CD159, CD162R, CD223, CD244.

Monocyte/myeloid cell or monocyte/myeloid cell subsets antigens expressed, either as whole proteins or smaller peptides of the whole proteins, on such cells can be but are not limited to CDw12, CD13, CD14, CD33, CD64, CD11, CD112, CD115, CD163, CD204.

Dendritic cell or dendritic subsets antigens expressed, either as whole proteins or smaller peptides of the whole proteins, on such cells can be but are not limited to CD85, CD205, CD209.

Neutrophil cell or neutrophil subset antigens expressed, either as whole proteins or smaller peptides of the whole proteins, on such cells can be but are not limited to CD66a, CD66c, CD170.

Basophil cell or basophil subset antigens expressed, either as whole proteins or smaller peptides of the whole proteins, on such cells can be but are not limited to surface IgE, CD123, CD203e, FceR1a.

Eosinophil cell or eosinophil subset antigens expressed, either as whole proteins or smaller peptides of the whole proteins, on such cells can be but are not limited to siglec-8, CD294.

Mast cell or mast subset antigens expressed, either as whole proteins or smaller peptides of the whole proteins, on such cells can be but are not limited to surface IgE, FceR1a, CD117.

Platelets/megakaryocytes or platelet/megakaryocyte subset antigens expressed, either as whole proteins or smaller peptides of the whole proteins, on such cells can be but are not limited to CD41, CD42a/b/c/d, CD51, CD110.

Haematopoietic progenitor cells or haematopoietic progenitor cell subset antigens expressed, either as whole proteins or smaller peptides of the whole proteins, on such cells can be but are not limited to CD34, CD46, CD55, CD90, CD100, CD117, CD123, CD127, CD243, CD338, SSEA-3, SSEA-5, TRA-1-81, TRA-2-49, TRA-2-54.

Cells which transgress the blood-brain barrier (BBB).

In the method provided herein B may bind a target cell.

In one embodiment B is specific to a cell surface marker on a target cell selected from a stably expressed cell lineage marker and a marker stably expressed on non-lineage cells (for example with the proviso that A and B are not specific to the same cell surface markers where they are targeting the same cell type).

In one embodiment the target cell comprises a cell or tissue which is disease associated to which it is desired to direct an effector cell which can bring a cellular activity to bear on the target cell.

In one embodiment the target cell is one with an aberrant function, for example associated with a disease or pathology. Examples of target cells include cells or tissues associated with disease such as cancer, autoimmunity, infection or degeneration. Examples include tumor cells, T cells and B cells.

In one embodiment B is specific to a surface marker where the target cell is a tumor antigen, for example selected from erbB-2, CEA, NCAM, GD2, CD33, CD44, CD70, EpCAM, CD19, CD20, KDR, Tag-72.

In one embodiment B is specific to a target cell antigen selected from the group comprising TSHR (thyrotropin receptor, thyroid), CD31 (endothelium), CD41 (platelets), CD103 (intraepithelial lymphocytes), CD117 haeompoetic stem cells) Surfactant protein C (SP-C, lung epithelium), Clara cell secretory protein (CC16, lung epithelium), vWF (endothelium).

In one embodiment is B specific to a surface marker on the target cells is a HER receptor, for example HER1, 2, 3 or 4.

In one embodiment B is specific to a B cell marker on a target cell is selected from the group comprising CD19, CD20, CD21, CD22, CD23, CD24, CD27, CD35, CD38, CD40, B220 (also known as CD45), CD43, CD81, CD138, CXCR4, BCMA and IL-6R, for example CD38, CD138, CD45, CD27, CD19 or CD20, such as CD38 or CD138.

In one embodiment B is specific to a B cell marker in a constant region of an antibody light chain or a constant region of an antibody heavy chain, expressed as part of an immunoglobulin on the surface of the cell, for example the marker is specific to antibody isotype selected from the group comprising IgG1, IgG2, IgG3, IgG4, IgA1, IgA2, IgE and IgM.

In one embodiment B is specific a T cell marker is selected from the group comprising CD2, CD3, CD4, CD5, CD6, CD7, CD8, CD25, CD127 CD196 (CCR6), CD197 (CCR7), CD62L, CD69 and CD45.

In one embodiment target cells and antigens on target cells that may be bound by B include:—

B cell or B cell subsets antigens expressed, either as whole proteins or smaller peptides of the whole proteins, on such cells can be but are not limited to CD19, CD20, CD21, CD22, CD23, CD24, CD35, CD79a, CD79b, CD81, CD138, CD139 etc.

T cell or T cell subsets antigens expressed, either as whole proteins or smaller peptides of the whole proteins, on such cells can be but are not limited to CD2, CD3, CD4, CD5, CD6, CD7, CD8, CD28, CD152, CD154, CD160.

Normal NK cell or NK cell subsets antigens expressed, either as whole proteins or smaller peptides of the whole proteins, on such cells can be but are not limited to CD16, CD56, CD96, CD158, CD159, CD162R, CD223, CD244.

Monocyte/myeloid cell or monocyte/myeloid cell subsets antigens expressed, either as whole proteins or smaller peptides of the whole proteins, on such cells can be but are not limited to CDw12, CD13, CD14, CD33, CD64, CD11, CD112, CD115, CD163, CD204.

Dendritic cell or dendritic subsets antigens expressed, either as whole proteins or smaller peptides of the whole proteins, on such cells can be but are not limited to CD85, CD205, CD209.

Neutrophil cell or neutrophil subset antigens expressed, either as whole proteins or smaller peptides of the whole proteins, on such cells can be but are not limited to CD66a, CD66c, CD170.

Basophil cell or basophil subset antigens expressed, either as whole proteins or smaller peptides of the whole proteins, on such cells can be but are not limited to surface IgE, CD123, CD203e, FceR1a.

Eosinophil cell or eosinophil subset antigens expressed, either as whole proteins or smaller peptides of the whole proteins, on such cells can be but are not limited to siglec-8, CD294.

Mast cell or mast subset antigens expressed, either as whole proteins or smaller peptides of the whole proteins, on such cells can be but are not limited to surface IgE, FceR1a, CD117.

Platelets/megakaryocytes or platelet/megakaryocyte subset antigens expressed, either as whole proteins or smaller peptides of the whole proteins, on such cells can be but are not limited to CD41, CD42a/b/c/d, CD51, CD110.

Haematopoietic progenitor cells or haematopoietic progenitor cell subset antigens expressed, either as whole proteins or smaller peptides of the whole proteins, on such cells can be but are not limited to CD34, CD46, CD55, CD90, CD100, CD117, CD123, CD127, CD243, CD338, SSEA-3, SSEA-5, TRA-1-81, TRA-2-49, TRA-2-54.

Erythrocyte or erythrocyte subset antigens expressed, either as whole proteins or smaller peptides of the whole proteins, on such cells can be but are not limited to CD233, CD235a/b, CD236, CD238, CD239, CD241, CD242, Ter119.

Endothelial cells or endothelial cell subset antigens expressed, either as whole proteins or smaller peptides of the whole proteins, on such cells can be but are not limited to CD62E, CD144, CD146, CD201, CD202b.

In one embodiment, when A is expressed on an effector cell that transgresses the blood brain barrier, B may bind a central nervous system expressed target such as alpha-synuclein, Tau isoforms, Abeta amyloid, beta secretase, gamma secretase, TDP43, super oxide dismutase SOD1, prion proteins or Huntingtin protein.

The effector cell may naturally have a desired cellular activity which will be directed by A-X:Y-B to a target cell.

Alternatively the effector cell may have activity augmented or introduced by transfecting the effector cell with a polynucleotide sequence encoding A-X, in particular where A comprises a signalling region.

The formation of the heterodimeric-tether X:Y brings the effector cell and the target cell into proximity of each other. This allows the effector function to exert an effect on the target cell, for example destruction of the target cell and/or modulation of target cell function.

Destruction of a target cell or modulation of target cell function by direction of an effector cell could have therapeutic potential in a wide variety of diseases, affecting multiple tissue types including, but not restricted to skin, stomach, intestine, kidney, bladder, testes, prostate, breast, ovary, adipose, skeletal muscle, lung, bone, pancreas, lymph nodes and CNS. A large number of cell types can be targeted across these tissues with involvement in inflammatory, autoimmune, neoplastic and tumuorigenic pathologies where they can be modulated, inhibited, activated or deleted, such as myofibroblasts, fibroblasts, endothelial cells, epithelial cells, neuronal cells, osteoclasts/blasts/cytes, neutrophils, macrophages, T cells, B cells, dendritic cells and eosinophils. Examples of conditions that could be targeted include any autoimmune condition (for example multiple sclerosis, systemic lupus erythematosus, sarcoidosis, rheumatoid arthritis, idiopathic pulmonary fibrosis), epithelial and haematological malignancies, angiogenesis, allergic inflammatory disease, fibrosis, bone disease (for example osteoporosis), inflammatory disease caused by dysregulation of leukocyte homeostasis (for example neutrophil, macrophage, T cell, B cell and dendritic cell functions), neuroinflammatory and neurodegenerative diseases.

When A is cell expressed to present X on the cell surface, in addition to a transmembrane domain, A may optionally comprise an N terminal spacer region.

In one embodiment the method employs docking the A-X to a cell surface marker whilst the other arm B-Y is employed to target a cell of interest and hold it in the vicinity of the cell to which A-X is bound through the heterodimeric-tether formed by X:Y.

In one embodiment A is independently selected from a full length antibody, a Fab fragment, a Fab' fragment, a sdAb (VHH, VH, VL), a scFv, a protein and a protein ligand; one or more components of a cell surface protein for example a transmembrane domain, or a complex, for example a transmembrane domain and a ligand to a receptor expressed on the surface of the effector cell, or combinations thereof.

In one embodiment B is independently selected from a full length antibody, a Fab fragment, a Fab' fragment, a sdAb (VHH, VH, VL), a scFv, and an antigen, for example a ligand to a receptor expressed on the surface of the target cell, for example is a full length antibody, a Fab fragment, a Fab' fragment, or a sdAb, or a scFv, such as Fab or Fab' fragment, in particular a Fab fragment.

In one example A and B may both bind T or B cells but not via the same markers.

In one example when A is not specific to a B or T cell marker, B may be specific to a B or T cell marker.

When A comprises a transmembrane domain then X may be presented on the cell surface attached to the N-terminal of the protein A, optionally via a spacer.

When A-X is a fusion protein, which is not expressed on the cell surface, in particular where A is an antibody or binding fragment thereof, X may, for example be presented on the C-terminal of the protein, such as on the C-terminal of terminal of the heavy chain.

In one embodiment X is connected or linked to A via a linker, for example a linker disclosed herein.

In one embodiment X is directly linked/fused to A (i.e. no linker is employed).

In one embodiment Y is linked/connected to the C-terminal of the protein B, for example linked to the C-terminal of the heavy chain of an antibody or binding fragment represented by B.

In one embodiment Y is directly linked/fused to B (i.e. no linker is employed).

In one embodiment Y is connect or linked to B via a linker, for example a linker disclosed herein.

In one embodiment the linker is selected from AAASGGG SEQ ID NO: 74, ASGGG SEQ ID NO: 73, ASGGGG SEQ ID NO: 71, SGGGGSGGGGSGGGGS SEQ ID NO: 18, and SGGGGSGGGGSGGGGSGGGS SEQ ID NO: 75.

When A or B is a Fab and the corresponding X or Y is a peptide then the linker to the respective X or Y may, for example be ASGGGG, ASGGG, AAASGGG SEQ ID NO: 74.

When A or B is a scFv and the corresponding X or Y is a peptide then the linker may, for example be ASGGG, ASGGGG or AAASGGG.

When A or B is a scFv and the corresponding X or Y is a scFv or sdAb then the linker may, for example be selected from SGGGGSGGGGSGGGGS and SGGGGSGGGGSGGGGSGGGS.

In one embodiment there is provided a method of treatment comprising adoptive transfer of effector cells presenting X on the surface, for example cells expressing A-X, such that X is expressed on the surface.

Methods for adoptive cell transfer/therapy or engraftment are well known in the art, including techniques where cells are transfected both in vivo and ex vivo (Feldmann et al., 2015, Seminars in Oncology, 42, 4, 626-639 and Dunkin et al., 2014, Digestive Diseases, 32, 61-66).

The antibody format of the disclosure is such that the bispecific protein complexes can be readily assembled in vitro or in vivo and these can be used to treat patients There is no difficulty expressing the unit A-X or the unit B-Y. The amount of purification required after expression of each unit (A-X or B-Y) is minimal or in fact, unnecessary. The bispecific complex can be formed in a 1:1 molar ratio by simply admixing the relevant units i.e. without recourse to conjugation and coupling chemistry. The binding partners X and Y drive the equilibrium in favour of forming the requisite heterodimer bispecific complex. Again little or no purification is required after formation of the complex after heterodimerisation. Thus large number of A-X and B-Y can be readily prepared and combined.

In one embodiment A and/or B comprise an Fc region.

In one embodiment the A and/or B in the constructs of the present disclosure lack an Fc region.

In one embodiment one or more scFvs employed in the bispecific protein complex according to the present disclosure is disulfide stabilised.

The ability to prepare a bispecific complex lacking the Fc fragment CH2-CH3 also ensures that the biological activity observed is in fact due solely to the variable region pairs in the complex. The simplicity of the bispecific complex of the invention and the methods of preparing it are a huge advantage in the context of rapid and extensive screening for characterisations, isolation purposes, etc.

In one embodiment the heterodimerically-tethered bispecific protein complex A-X:Y-B is prepared by mixing A-X and B-Y in vitro before introducing the complex to the cells for treatment. Thus in one embodiment the method comprises an in vitro mixing step bringing A-X and B-Y into contact.

In one embodiment the components A-X and B-Y are introduced a separate fusion proteins but at approximately the same time to the cells for treatment and come together to form the complex A-X:Y-B after their addition to the sample of cells.

In one embodiment A-X or B-Y is first added to the cells (including in vivo) for treatment and later the corresponding reagent, respectively B-Y and A-X is added. The time difference may be, for example 15 mins to 24 hours. Only after addition of the second fusion protein does the complex A-X:Y-B form.

Thus in one embodiment the fusion proteins A-X and B-Y are not co-expressed in the same cell. This is advantageous because it allows, for example 100 fusion proteins to expressed and optionally purified and the subsequent mixing of the 100 fusion proteins in the various permutations can provide 10,000 heterodimerically-tethered bispecific protein complexes, of which 5,000 are unique pairs.

However, if desired the A-X and B-Y may be expressed in the same cell.

The binding partners X and Y have affinity for each other and act as biological equivalent of Velcro® or a bar and magnet and hold the complex together. Advantageously, this means that the fusion proteins A-X and Y-B can be readily assembled into a bispecific protein complex simply by mixing the fusion proteins together. Thus the bispecific protein complex of the present disclosure has a modular structure which allows for two different proteins to be easily assembled in order to produce large panels of permutations of bispecific protein complexes with different combinations of antigen specificities in, for example a grid-like fashion. This allows for the efficient and systematic screening of a large number of bispecific protein complexes for use in treatment of various disease states.

Given X and Y are specific for each other this significantly reduces the ability to form homodimers. X and Y are collectively referred to herein as a binding pair or binding partners. In one embodiment X does not have high affinity for other Xs. In one embodiment Y does not have high affinity for other Ys. Advantageously, when X and Y do not form homodimers, this prevents the formation of undesired monospecific protein complexes, increases yield of the desired bispecific protein complexes, and removes the need for onerous purification steps to remove the monospecific protein complexes.

This allows rapid assembly of bispecific protein complexes with a yield and/or purity which cannot be obtained efficiently by most prior art methods, in particular prior art methods generally require extensive purification steps. The yield of bispecific complex is typically 75% or higher in the present invention.

DETAILED DESCRIPTION

Figure 1:
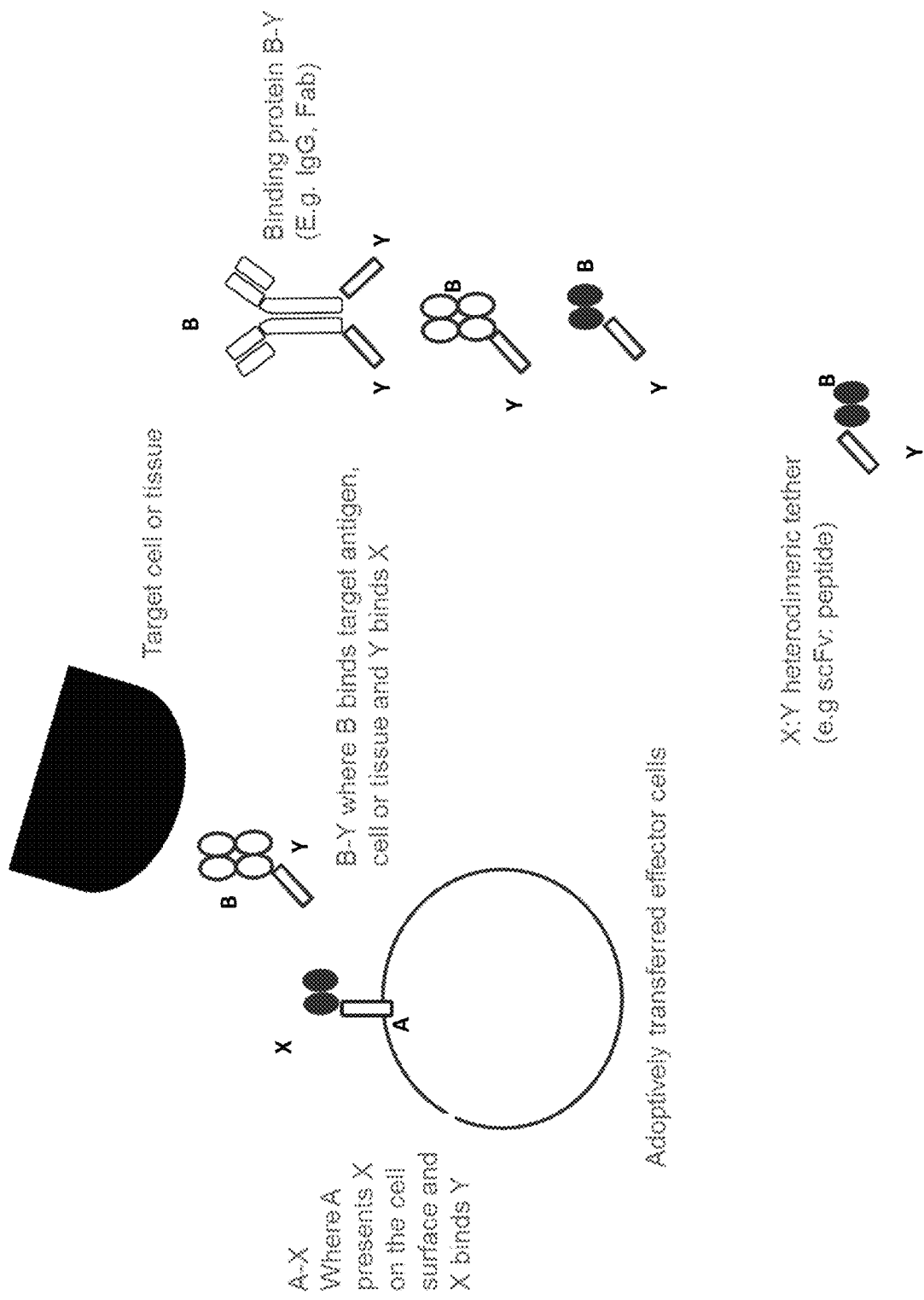
FIG. 1 shows an A-X fusion protein expressed on the surface of a cell (wherein A is a surface protein which is not connected to an intra-cellular signalling domain and X is a scFv) and B is a Fab specific to an epitope on the surface of a target cell or tissue and Y is a peptide specific to X. Alternative formats for B-Y are also provided.

"Bispecific protein complex" as used herein refers to a molecule comprising two proteins (A and B referred to herein as bispecific components also referred to herein as the first protein component and second protein component, respectively of the bispecific) which are retained together by a heterodimeric-tether. In one embodiment one or both of the proteins have a binding domain, for example one or both of the proteins are antibodies or fragments thereof (in particular a Fab or Fab' fragment, such complexes are also referred to as Fab-Kd-Fab). "Fusion proteins" as employed herein comprise a protein component A or B fused to a binding partner X or Y (as appropriate). In one embodiment the fusion protein is a translational protein expressed by recombinant techniques from a genetic construct, for example expressed in a host from a DNA construct. In the context of the present disclosure one of the key characteristics of a fusion protein is that it can be expressed as a "single protein/unit" from a cell (of course in the case of fusion proteins comprising a Fab/Fab' fragment there will be two chains but this will be considered a single protein for the purpose of the present specification with one chain, typically the heavy chain fused at its C-terminus to X or Y as appropriate, optionally via a linker as described herein below).

The function of the heterodimeric tether X:Y is to retain the proteins A and B in proximity to each other so that function of A and B or the cells appended thereto can be effected.

The term "heterodimeric-tether" as used herein refers to a tether comprising two different binding partners X and Y which form an interaction: (such as a binding) between each other which has an overall affinity that is sufficient to retain the two binding partners together. In one embodiment X and/or Y are unsuitable for forming homodimers.

Heterodimerically-tethered and heterodimeric-tether are used interchangeably herein.

In one embodiment "unsuitable for forming homodimers" as employed herein refers to formation of the heterodimers of X-Y are more preferable, for example more stable, such as thermodynamically stable, once formed than homodimers. In one embodiment the binding interaction between X and Y is monovalent.

The term "protein ligand" as used herein means a binding partner (such as a ligand, a cytokine, a chemokine) of a cell surface protein (such as a transmembrane bound receptor).

A "component of a cell surface protein or a complex thereof" as used herein means a defined region of a cell surface protein and include, but is not limited to, a transmembrane region, an intracellular signalling region and the like.

In one embodiment the X-Y interaction is more favourable than the X-X or Y-Y interaction. This reduces the formation of homodimers X-X or Y-Y when the fusion proteins A-X and B-Y are mixed. Typically greater than 75% heterodimer is formed following 1:1 molar ratio mixing.

If desired, a purification step (in particular a one-step purification), such as column chromatography may be employed, for example to purify the fusion protein units and/or bispecific protein complexes according to the present disclosure.

In one embodiment a purification step is provided after expression of each fusion protein, although typically aggregate levels are low. Thus in one embodiment prior to in vitro mixing, the fusion protein(s) is/are provided in substantially pure form. Substantially pure form as employed herein refers to wherein the fusion protein is 90, 91, 92, 93, 94, 95, 96, 97, 98, 99 or 100% monomer.

In one embodiment no purification of the fusion protein or proteins is performed.

In one embodiment each fusion protein unit is expressed in a different expression experiment/run.

In one embodiment no purification of the fusion protein or proteins is performed before mixing to generate a bispecific protein complex. In one embodiment no purification of the fusion protein or proteins is performed before and/or after mixing.

In one embodiment no purification is required after the bispecific protein complex formation.

In one embodiment after mixing, and generally without further purification, at least 50% of the composition is the desired bispecific protein complex, for example at least 60, 65, 70, 75, 80% of the composition is the required bispecific protein complex.

In one embodiment the ratio of A-X to B-Y employed in the in vitro mixing step is 1:1, in particular a 1:1 molar ratio.

The present disclosure also extends to a method of preparing a bispecific complex according to the present disclosure comprising admixing a fusion protein A-X and B-Y, for example in a 1:1 molar ratio.

In one embodiment the mixing occurs in vitro.

In one embodiment mixing occurs in a cell, for example a host cell expressing said fusion proteins.

In one embodiment, the mixing occurs in vivo, i.e. the fusion proteins A-X and B-Y interact with each other within a subject's body to form the heterodimeric-tether and in consequence, the bispecific protein complex.

This is advantageous because one component, for example A-X may be administered or introduced and it is not activated until the further component B-Y is added and forms the heterodimeric-tether.

In one embodiment, X and Y are completely specific for each other and do not bind to any other peptides/proteins in a cell or within a subject's body. This can be achieved for example by ensuring that X and Y are not naturally present in the target cell or in the target subject's body. This can be achieved, for example by selecting X or Y to be from a species or entity which is different to the subject (e.g. a yeast protein) and ensuring the other variable is specific to it. Advantageously, this prevents the binding of the fusion proteins A-X and/or B-Y to an undesired target, thereby generating unwanted off-target effects.

Generally at least one of X or Y will be an antigen, such as a peptide. In the present disclosure the antigen, such as a peptide employed in X or Y has been chosen to be non-mammalian. That is not from a mammalian protein, such as not similar to or identical to a mammalian protein. In one embodiment a peptide or antigen employed in an X or Y is 90% identical or similar or less (such as 85, 80, 75, 70, 65, 60% or less) to a mammalian sequence over the same length. As discussed above this helps to ensure that the X:Y are specific for each other when employed in vivo and reduces the risk of off-target effects to patients.

In one embodiment one (or at least one) of the binding partners is incapable of forming a homodimer, for example an amino acid sequence of the binding partner is mutated to eliminate or minimise the formation of homodimers.

In one embodiment both of the binding partners are incapable of forming a homodimer.

Incapable of forming homodimers or aggregates as employed herein, refers to a low or zero propensity to form homodimers or aggregate. Low as employed herein refers to 5% or less, such as 4, 3, 2, 1, 0.5% or less aggregate, for example after mixing or expression or purification.

Small amounts of aggregate in the fusion proteins or residual in the heterodimerically-tethered bispecific protein complex may be acceptable in pharmaceutical compositions of the heterodimerically-tethered bispecific protein complex of the disclosure.

In one embodiment: is a binding interaction based on attractive forces, for example Van der Waals forces, such as hydrogen bonding and electrostatic interactions, in particular, based on antibody specificity for an antigen (such as a peptide).

In one embodiment conjugation/coupling chemistry is not employed to prepare the bispecific protein complexes of the present disclosure.

"Form the complex" as employed herein refers to an interaction, including a binding interaction or a chemical reaction, which is sufficiently specific and strong when the fusion protein components A-X and B-Y are brought into contact under appropriate conditions that the complex is assembled and the fusion proteins are retained together.

"Retained together" as employed herein refers to the holding of the components (the fusion proteins) in the proximity of each other, such that after X:Y binding the complex can be handled as if it were one molecule, and in many instances behaves and acts like a single molecule. In one embodiment the retention renders the complex suitable for use in the method disclosed herein, i.e. suitable for use in at least one functional screen.

Specificity as employed herein refers to where, for example the partners in the interaction e.g. X:Y or A and antigen or B and antigen only recognise each other or have significantly higher affinity for each other in comparison to non-partners, for example at least 2, 3, 4, 5, 6, 7, 8, 9, 10 times higher affinity, than for example a background level of binding to an unrelated non partner protein.

Specificity in relation to X and Y as employed herein refers to where the binding partners X and Y in the interaction only recognise each other or have significantly higher affinity for each other in comparison to non-partners, for example at least 2, 3, 4, 5, 6, 7, 8, 9, 10 times higher affinity.

In one embodiment the binding interaction is reversible. In one embodiment the binding interaction is essentially irreversible.

Essentially irreversible as employed herein refers to a slow off rate (dissociation constant) of the antibody or binding fragment.

In one embodiment, the binding interaction between X and Y has a low dissociation constant. Examples of a low dissociation constant include $1-9\times10^{-2}$ $s^{-1}$ or less, for example $1-9\times10^{-3}$ $s^{-1}$, $1-9\times10^{-4}$ $s^{-1}$, $1-9\times10^{-5}$ $s^{-1}$, $1-9\times10^{-6}$ $s^{-1}$ or $1-9\times10^{-7}$ $s^{-1}$. Particularly suitable dissociation constants include $2\times10^{-4}$ $s^{-1}$ or less, for example $1\times10^{-5}$ $s^{-1}$, $1\times10^{-6}$ $s^{-1}$ or $1\times10^{-7}$ $s^{-1}$.

Whilst not wishing to be bound by theory it is thought that the low dissociation constant (also referred to as off rate) allows the molecules to be sufficiently stable to render the bispecific protein complex useful, in treatment.

In another embodiment, the affinity of X and Y for each other is 5 nM or stronger, for example 900 pM or stronger, such as 800, 700, 600, 500, 400 or 300 pM.

Affinity is a value calculated from the on and off rate of the entity. The term "affinity" as used herein refers to the strength of the sum total of non-covalent interactions between a single binding site of a molecule (e.g. an antibody) and its binding partner (e.g. a peptide).

The affinity of a molecule for its binding partner can generally be represented by the dissociation constant (KD). Cell surface marker is a moiety, for example a protein expressed on the surface of the cell that be employed alone or in combination with other surface marker to identify and/or isolate the cell. The marker may be associated with the lineage of the cell or activation status of the cell, a molecule expressed by the cell or the like.

In one embodiment the cell surface marker is a tumor antigen, such as erbB-2, CEA, NCAM, GD2, CD33, CD44, CD70, EpCAM, CD19, CD20, KDR, Tag-72, In another embodiment the cell surface marker is a protein such as a membrane protein which effects transfer through the blood-brain barrier (e.g. a transporter) of proteins, cells and other molecules from the blood to the brain.

In another embodiment the cell surface marker is on cells that are able to transgress the blood brain barrier.

Transmembrane domain or region is employed interchangeably herein to refer to a protein which spans the cell membrane thereby bridging the intra-cellular domain and the extracellular domain. See for example WO2004/039840 and WO2007/060406 both incorporated herein by reference.

A transmembrane region generally serves to anchor A-X to the cell membrane (thus the extracellular ligand-binding region is membrane-bound) and includes any protein (or nucleic acid encoding such a protein). Such a region can be derived from a wide variety of sources such as all or part of the alpha, beta, or zeta chain of the T cell receptor (TCR), CD28, CD4, CD5, CD8, CD3ε, CD16, CD22, CD23, CD45, CD80, CD86, CD64, CD9, CD37, CD122, CD137 or CD154, a cytokine receptor such as an interleukin receptor, TNF-R, a tyrosine kinase receptor or interferon receptor, or a colony stimulating factor receptor. Alternatively, the transmembrane region may be synthetic. Suitable synthetic transmembrane regions will comprise predominantly hydrophobic amino acids such as leucine and valine.

When A comprises a transmembrane region, a spacer region may optionally be included at the N terminal of the transmembrane region. Furthermore, an intracellular signalling region may optionally be included at the C terminal of that transmembrane region.

Spacer domain as employed herein refers to a polypeptide region separating the transmembrane region of A from X and may like in the case of artificial T cell receptors (Cytotherapy 2003 5 (3) 211-226) be necessary for optimal effector cell function. Examples of spacer regions are domains derived from naturally expressed cell surface molecules such as immunoglobulin, CD28, CD4, CD8, MHC. Combinations of region from these molecules may also be combined. Specific examples include the hinge, CH2 and CH3 region of human IgG1 or the hinge region of human IgG1 combined with an extracellular domain of human CD28 as described (J. Immunol 1998 161 2791-2797).

An intracellular signalling region includes any protein (or nucleic acid encoding such a protein) that can participate in the generation of a signal that results in direct or indirect production of an intracellular messenger system. Particular intracellular messenger systems include one or more kinase pathways such as a tyrosine kinase pathway, a MAP kinase pathway, or protein kinase C pathway; a G-protein or phospholipase-mediated pathway; a calcium-mediated pathway; a cAMP- or cGMP-mediated pathway; or one or more pathways involving synthesis of one or more cytokines such as an interleukin, e.g. IL-2, or transcription factors such as NFκB, NFAT or AP-1. The intracellular signalling regions are most preferably selected such that they act cooperatively.

Intracellular signalling regions may be derived from one or more naturally-occurring protein signalling sequences. Suitable examples include without limitation sequences derived from the TCR such as part of the zeta, eta or epsilon chain. and include the first (TCRζ1), second (TCRζ2) and third (TCRζ3) immunoreceptor tyrosine-based activation motifs (ITAMs) of the TCR zeta chain, FcRγ such as FcRIIIγ or FcRIγ, FcRβ such as FcRIβ; CD3γ; CD3δ; CD3ε; and CD5, CD22, CD79a, CD79b, or CD66d. Particularly preferred ITAMs include those derived from TCRζ1, TCRζ2, TCRζ3 and FcεRIγ; CD4; CD8; and the gamma chain of a Fc receptor.

Signalling regions can be derived from activating or inhibitory immune check point receptors or ligands (Nat Rev Drug Discovery. 2015. 14. 561-584) including:— CD40, CD40L, TL1A, TBFRSF25, GITR, GITR, CD137, CD137L, CD134, CD134L, CD70, CD27, HHLA2, TMIGD2, ICOSL, ICOS, CD80, CD86, CD28, LAG3, CTLA-4, PD1, PDL1, PDL2, VISTA, BTNL2, B7-H3, B7-H4, CD48, CD244, BTLA, CD160, LIGHT, HVEM, Butryophilin or siglec family members.

Chimeric receptor as employed herein as employed herein refers an engineered receptor which grafts two sequences from different origins onto a cell, in particular an effector cell. The bispecific protein complexes may be tethered to a solid substrate surface, for example attached to a bead, or they may be suspended in a liquid (e.g. a solution or media) form, for example within a well or within a droplet.

In one embodiment, at least one of the first binding partner, X, and the second binding partner, Y, of the binding pair are independently selected from a peptide and a protein; for example the first binding partner or second binding partner is a peptide.

Suitable peptides include the group comprising GCN4, Fos/Jun (human and murine Fos have a Uniprot number P01100 and P01101 respectively and human and murine jun have a Uniprot number 05412 and 05627 respectively), HA-tag which correspond to amino acids 98 to 106 of human influenza hemagglutinin, polyhistidine (His), c-myc and FLAG. Other peptides are also contemplated as suitable for use in the present disclosure and particularly suitable peptides are affinity tags for protein purification because such peptides have a tendency to bind with high affinity to their respective binding partners.

In one embodiment the peptide is not E5B9.

The term "peptide" as used herein refers to a short polymer of amino acids linked by peptide bonds, wherein the peptide contains in the range of 2 to 100 amino acids, for example 5 to 99, such as 6 to 98, 7 to 97, 8 to 96 or 5 to 25. In one embodiment a peptide employed in the present disclosure is an amino acid sequence of 50 amino acid residues or less, for example 40, 30, 20, 10 or less. Polypeptide and protein are employed interchangeably herein. In one embodiment, the protein is an antibody or an antibody fragment.

The term "antibody" as used herein refers to an immunoglobulin molecule capable of specific binding to a target antigen, such as a carbohydrate, polynucleotide, lipid, polypeptide, peptide etc., via at least one antigen recognition site (also referred to as a binding site herein), located in the variable region of the immunoglobulin molecule.

As used herein "antibody molecule" includes antibodies and binding fragments thereof.

"Antibody fragments" as employed herein refer to antibody binding fragments including but not limited to Fab, modified Fab, Fab', modified Fab', F(ab')2, Fv, single domain antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216:165-181). Other antibody fragments for use in the present disclosure include the Fab and Fab' fragments described in International patent applications WO05/003169, WO05/003170 and WO05/003171. Multivalent antibodies may comprise multiple specificities e.g. bispecific or may be monospecific (see for example WO92/22853, WO05/113605, WO2009/040562 and WO2010/035012).

A "binding fragment" as employed herein refers to a fragment capable of binding a target peptide or antigen with sufficient affinity to characterise the fragment as specific for the peptide or antigen.

The term "Fab fragment" as used herein refers to an antibody fragment comprising a light chain fragment comprising a VL (variable light) domain and a constant domain of a light chain (CL), and a VH (variable heavy) domain and a first constant domain (CH1) of a heavy chain. In one example the heavy chain sequences of the Fab fragment "terminates" at the interchain cysteine of CH1. In one embodiment the Fab fragment employed in a fusion protein of the present disclosure, such as A-X and/or B-Y is monovalent.

A Fab' fragment as employed herein refers to a Fab fragment further comprising all or part of a hinge region. In one embodiment the Fab' fragment employed in a fusion protein of the present disclosure, such as A-X and/or B-Y is monovalent.

The term "single-chain Fv" or abbreviated as "scFv", as used herein refers to an antibody fragment that comprises VH and VL antibody domains linked (for example by a peptide linker) to form a single polypeptide chain. The constant regions of the heavy and light chain are omitted in this format. Single-chain Fv as employed herein includes disulfide stabilised versions thereof wherein in addition to the peptide linker a disulfide bond is present between the variable regions.

Disulfide stabilised scFv may eliminate the propensity of some variable regions to dynamically breath, which relates to variable regions separating and coming together again. The term "single domain antibody" as used herein refers to an antibody fragment consisting of a single monomeric variable antibody domain. Examples of single domain antibodies include VH or VL or VHH.

In one embodiment the antibody binding fragment and/or the bispecific antibody complex does not comprise an Fc region. "Does not comprise an Fc region" as employed herein refers to the lower constant domains, such as CH2, CH3 and CH4 which are absent. However, constant domains such as CH1, CKappa/CLambda may be present.

In one embodiment, the antibody heavy chain comprises a CH1 domain and the antibody light chain comprises a CL domain, either kappa or lambda.

In one embodiment, the antibody heavy chain comprises a CH1 domain, a CH2 domain and a $CH_3$ domain and the antibody light chain comprises a CL domain, either kappa or lambda.

In one embodiment, the first protein, A, and/or second protein, B, of the bispecific protein complex is an antibody or antibody fragment. Such a bispecific protein complex may be referred to as a bispecific antibody complex.

Bispecific protein complex comprise a protein capable of binding the cell surface and protein capable of binding a soluble molecule secrete from the cell, tethered together by X and Y.

In one embodiment the bispecific protein complex is an bispecific antibody complex.

In one embodiment "Bispecific antibody complex" as employed herein refers to a bispecific protein complex comprising at least two antibody binding sites wherein the component antibodies, fragments or both are complexed together by a heterodimeric-tether.

Complexed (or in complex with) as employed herein generally refers to where A-X and B-Y are tethered together by the interaction X:Y.

Uncomplexed as employed herein refers to where A-X and B-Y are separate molecules.

In one embodiment each antibody or fragment employed in the bispecific antibody complex of the disclosure comprises one binding site i.e. each binding site is monovalent for each target antigen.

Antigen as employed herein as employed herein refers to a molecule which under appropriate conditions stimulates the body to raise antibodies to it.

The full length antibody or antibody fragment employed in the fusion proteins (A-X or B-Y) may be monospecific, monovalent, multivalent or bispecific.

In one embodiment, the antibody or antibody fragment employed in the first fusion protein (A-X) is a monospecific antibody or antibody fragment, in particular a monovalent Fab, Fab', scFv, Fv, VHH or similar.

In one embodiment, the antibody or antibody fragment employed in the second fusion protein (B-Y) is a monospecific antibody or antibody fragment, in particular a monovalent Fab, Fab', scFv or similar.

"Monospecific" as employed herein refers to the ability to bind only one target antigen.

"Monovalent" as employed herein refers to the antibody or antibody fragment having a single binding site and therefore only binding the target antigen only once.

In one embodiment, the antibody or antibody fragment employed in the first fusion protein (A-X) is multivalent, that is has two or more binding domains.

In one embodiment, the antibody or antibody fragment employed in the second fusion protein (B-Y) is multivalent, that is has two or more binding domains.

In one embodiment, the antibody or antibody fragment employed in the first fusion protein (A-X) is monovalent and the antibody or antibody fragment employed in the second fusion protein (B-X) is monovalent.

In one embodiment, the antibody or antibody fragment employed in the first fusion protein (A-X) is monovalent and the antibody or antibody fragment employed in the second fusion protein (B-Y) is multivalent.

In one embodiment, the antibody or antibody fragment employed in the first fusion protein (A-X) is multivalent and the antibody or antibody fragment employed in the second fusion protein (B-Y) is monovalent.

In one embodiment, the antibody or antibody fragment employed in the first fusion protein (A-X) is multivalent and the antibody or antibody fragment employed in the second fusion protein (B-Y) is multivalent.

In one embodiment A-X or B-Y is not a fusion protein comprising two scFvs one specific to the antigen CD33 and one specific to the antigen CD3 or alternatively a bispecific complex format specific to these two antigens.

In one embodiment the A-X or B-Y is not a fusion protein comprising a scFv (or alternatively another antibody format) specific to CD3 linked to a peptide E5B9.

A "binding domain or site" as employed herein is the part of the antibody that contacts the antigen/epitope and participates in a binding interaction therewith. In one embodiment the binding domain contains at least one variable domain or a derivative thereof, for example a pair of variable domains or derivatives thereof, such as a cognate pair of variable domains or a derivative thereof.

In one embodiment the binding domain comprises 3 CDRs, in particular where the binding domain is a domain antibody such as a VH, VL or VHH. In one embodiment the binding domain comprises two variable domains and 6 CDRs and a framework and together these elements contribute to the specificity of the binding interaction of the antibody or binding fragment with the antigen/epitope.

A "cognate pair" as employed herein refers to a heavy and light chain pair isolated from a host as a pre-formed couple. This definition does not include variable domains isolated from a library, wherein the original pairings from a host is not retained. Cognate pairs may be advantageous because they are often affinity matured in the host and therefore may have high affinity for the antigen to which they are specific.

A "derivative of a naturally occurring domain" as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained. Examples of modifications are those to remove glycosylation sites, or solvent exposed lysines. These modifications can be achieved by replacing the relevant amino acid residues with a conservative amino acid substitution.

In one embodiment, the bispecific antibody complexes of the present disclosure or antibody/fragment components thereof are processed to provide improved affinity for a target antigen or antigens. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment, the first antibody or antibody fragment (A) is specific to a first antigen and the second antibody or antibody fragment (B) is specific to a second antigen, and generally the first and second antigens are different. Advantageously, the bispecfic or antibody complex may be specific for two different antigens. This presents the possibility of the antibody complex binding to two different antigens, each located on a different entity, thereby bringing the two entities into close physical proximity with each other.

In one embodiment, the first antibody/fragment (A), second antibody/fragment (B) or both the first and second antibody/fragment of the bispecific antibody complex of the present disclosure may be a Fab.

In one embodiment, the first antibody/fragment (A), second antibody/fragment (B) or both the first and second antibody/fragment of the bispecific antibody complex of the present disclosure may be a Fab'.

In one embodiment, the first antibody/fragment (A), second antibody/fragment (B) or both the first and second antibody/fragment of the bispecific antibody complex of the present disclosure may be a scFv.

In one embodiment, the first (A) or second (B) antibody/fragment or both the first and second antibody/fragment of the bispecific antibody complex of the present disclosure is/are a VHH. For convenience bispecific protein complexes of the present disclosure are referred to herein as A-X:Y-B. A and B and X and Y are nominal labels referred to for assisting the explanation of the present technology.

"Attached" as employed herein refers to connected or joined directly or indirectly via a linker, such as a peptide linker examples of which are discussed below. Directly connected includes fused together (for example a peptide bond) or conjugated chemically.

"Binding partner" as employed herein refers to one component part of a binding pair.

In one embodiment, the affinity of the binding partners is high, 5 nM or stronger, such as 900, 800, 700, 600, 500, 400, 300 pM or stronger.

"Binding pair" as employed herein refers to two binding partners which specifically bind to each other. Examples of a binding pair include a peptide and an antibody or binding fragment specific thereto, or an enzyme and ligand, or an enzyme and an inhibitor of that enzyme.

In one embodiment, the first binding partner (X) is selected from the group comprising: a full length antibody, a Fab, a Fab', Fv, dsFv, a scFv and a sdAb, wherein examples of a sdAb include VH or VL or $V_HH$.

When X is an antibody or binding fragment thereof then Y is a protein or peptide, in particular a peptide.

In one embodiment, the second partner (Y) is selected from the group comprising: a full length antibody, a Fab, a Fab', Fv, dsFv, a scFv and a sdAb, wherein examples of a sdAb include VH or VL or VHH.

When Y is an antibody or binding fragment thereof then X is a protein or peptide, in particular a peptide.

In one embodiment, where A is an antibody or fragment thereof the first binding partner (X) is attached to the C-terminal of the heavy or light chain of the first antibody or antibody fragment, for example, the first binding partner (X) is attached to the C-terminal of the heavy chain of the first antibody or antibody fragment (A).

In another embodiment, where B is an antibody or fragment thereof the second binding partner (Y) is attached to the C-terminal of the heavy or light chain of the second antibody or antibody fragment, for example the second binding partner (Y) is attached to the C-terminal of the heavy chain of the second antibody or antibody fragment (B).

In one embodiment X is attached to the C-terminal of the heavy chain of the antibody or fragment (protein A) and Y is attached to the C-terminal of the heavy chain of the antibody or fragment (protein B).

In one embodiment X is attached via a linker (such as ASGGGG SEQ ID NO: 71 or ASGGGGSG SEQ ID NO: 72) or any other suitable linker known in the art or described herein below, to the C-terminal of the heavy chain of the antibody or fragment (protein A) and Y is attached via a linker (such as ASGGGG SEQ ID NO: 71 or ASGGGGSG SEQ ID NO: 72) to the C-terminal of the heavy chain of the antibody or fragment (protein B).

Examples of a suitable binding pair (X or Y) may include GCN4 (SEQ ID NOs: 1 or 76-98 or lacking the HIS tag, amino acids 1-38 of SEQ ID NOs: 1 or 76-98) or a variant thereof and 52SR4 (SEQ ID NOs: 3, 99 or 100 or lacking the HIS tag amino acids 1 to 243 of SEQ ID NO:3) or a variant thereof, which is a scFv specific for GCN4.

In a one embodiment, the first binding partner (nominally X) is GCN4 (for example as shown in SEQ ID NOs: 1, 76-98) or a fragment or variant thereof (for example without the His tag) and the second binding partner (nominally Y) is a scFv or sdAb specific for GCN4 (for example as shown in SEQ ID NOs: 3, 99 or 100) or a variant thereof.

In one embodiment, the first binding partner (nominally X) is a sFv or sdAb specific for GCN4 (for example as shown in SEQ ID NO: 3) or a variant thereof and the second binding partner (nominally Y) is GCN4 (for example as shown in SEQ ID NO: 1) or a fragment or variant thereof.

GCN4 variants include an amino acid sequence with at least 80%, 85%, 90%, 91%, 92%, 93%, 94% 95%, 96%, 97% or 98%, or 99% identity to SEQ ID NO: 1. GCN4 variants also include an amino acid having at least 80%, 85%, 90%, 91%, 92%, 93%, 94%, 95%, 96%, 97%, 98%, or 99% to a sequence encoded by a nucleotide sequence SEQ ID NO: 2.

A suitable scFv specific to GCN4 is 52SR4 (SEQ ID NOs: 3, 99 or 100 or amino acids 1-243 of SEQ ID NO: 3) or a variant thereof. Variants of 52SR4 include an amino acid sequence with at least 80%, or 85%, or 90%, or 95%, or 98%, or 99% identity to SEQ ID NO: 3. 52SR4 variants also include an amino acid sequence having at least at least 80%, or 85%, or 90%, or 95%, or 98%, or 99% to a sequence encoded by a nucleotide sequence SEQ ID NO: 4.

The present inventors have found that the single chain antibody 52SR4 and peptide GCN4, are a binding pair suitable for use in the bispecific protein complexes of the present disclosure.

Alternatively, any suitable antibody/fragment and antigen (such as a peptide) may be employed as X and Y. Preferably such an X and Y pair result in greater than 75% heterodimer when A-X and Y-B are combined in a 1:1 molar ratio.

In one embodiment, the first binding partner (X) and the second binding partner (Y) are a protein.

In one embodiment, the first binding partner (X) is an enzyme or an active fragment thereof and the second binding partner (Y) is a ligand or vice versa.

In one embodiment, the first binding partner (X) is an enzyme or an active fragment thereof and the second binding partner (Y) is an inhibitor of that enzyme or vice versa.

"Active fragment" as employed herein refers to an amino acid fragment, which is less than the whole amino acid sequence for the entity and retains essentially the same biological activity or a relevant biological activity, for example greater than 50% activity such as 60%, 70%, 80%, 85%, 90%, 91%, 92%, 93%, 94%, 95%, 96%, 97%, 98%, 99% or 100%.

In another embodiment, the first binding partner X is glutathione (GSH) and the second binding partner Y is glutathione-S-transferase (GST) or vice versa.

In another embodiment, X is Fos and Y is Jun or vice versa.

In another embodiment, X is His and Y is anti-His or vice versa.

In another embodiment, the binding pair is clamodulin binding peptide and Y is calmodulin or vice versa.

In another embodiment, X is maltose-binding protein and Y is an anti-maltose binding protein or fragment thereof or vice versa.

Other enzyme-ligand combinations are also contemplated for use in binding partners. Also suitable are affinity tags known in the art for protein purification because these have a tendency to bind with high affinity to their respective binding partners.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

In one embodiment, the first or second binding partner (X or Y) is a protein or peptide.

In one embodiment, the first and second fusion proteins comprise one or more peptide linkers. The linkers may be incorporated at various locations in the fusion proteins. For example, a linker may be introduced between a binding partner and the protein attached thereto.

In one embodiment, the linker is a peptide linker.

The term "peptide linker" as used herein refers to a peptide with an amino acid sequence. A range of suitable peptide linkers will be known to the person of skill in the art.

In one embodiment, the binding partners of the bispecific protein complexes are joined to their respective proteins via peptide linkers.

In one embodiment the fusion proteins are a translational fusion, that is a fusion protein expressed in a host cell comprising a genetic construct from which the fusion protein is expressed.

In one embodiment the fusion protein is prepared by fusing the heavy chain or light chain of A to X and/or the heavy chain or light chain of B to Y optionally via a peptide linker.

In one embodiment, the peptide linker is 50 amino acids in length or less, for example 20 amino acids or less.

Generally it will be more efficient to express the fusion protein recombinantly and therefore a direct peptide bond or a peptide linker that can be expressed by a host cell may be advantageous.

In one embodiment, the linker is selected from a sequence shown in sequence 5 to 75 or PPP (Tables 5, 6 and 7)

TABLE 5

| SEQ ID NO: | SEQUENCE |
| --- | --- |
| 5 | DKTHTCAA |
| 6 | DKTHTCPPCPA |
| 7 | DKTHTCPPCPATCPPCPA |
| 8 | DKTHTCPPCPATCPPCPATCPPCPA |

TABLE 5-continued

| SEQ ID NO: | SEQUENCE |
| --- | --- |
| 9 | DKTHTCPPCPAGKPTLYNSLVMSDTAGTCY |
| 10 | DKTHTCPPCPAGKPTHVNVSVVMAEVDGTCY |
| 11 | DKTHTCCVECPPCPA |
| 12 | DKTHTCPRCPEPKSCDTPPPCPRCPA |
| 13 | DKTHTCPSCPA |

TABLE 6

| SEQ ID NO: | SEQUENCE |
| --- | --- |
| 14 | SGGGGSE |
| 15 | DKTHTS |
| 16 | (S)GGGGS |
| 17 | (S)GGGGSGGGGS |
| 18 | (S)GGGGSGGGGSGGGGS |
| 19 | (S)GGGGSGGGGSGGGGSGGGGS |
| 20 | (S)GGGGSGGGGSGGGGSGGGGSGGGGS |
| 21 | AAAGSG-GASAS |
| 22 | AAAGSG-XGGGS-GASAS |
| 23 | AAAGSG-XGGGSXGGGS-GASAS |
| 24 | AAAGSG-XGGGSXGGGSXGGGS-GASAS |
| 25 | AAAGSG-XGGGSXGGGSXGGGSXGGGS-GASAS |
| 26 | AAAGSG-XS-GASAS |
| 27 | PGGNRGTTTTRRPATTTGSSPGPTQSHY |
| 28 | ATTTGSSPGPT |
| 29 | ATTTGS |
| 30 | AAAAAAAAAAAA |
| 31 | EPSGPISTINSPPSKESHKSP |
| 32 | GTVAAPSVFIFPPSD |
| 33 | GGGGIAPSMVGGGGS |
| 34 | GGGGKVEGAGGGGGS |
| 35 | GGGGSMKSHDGGGGS |
| 36 | GGGGNLITIVGGGGS |
| 37 | GGGGVVPSLPGGGGS |
| 38 | GGEKSIPGGGGS |
| 39 | RPLSYRPPFPFGFPSVRP |
| 40 | YPRSIYIRRRHPSPSLTT |
| 41 | TPSHLSHILPSFGLPTFN |
| 42 | RPVSPFTFPRLSNSWLPA |
| 43 | SPAAHFPRSIPRPGPIRT |

TABLE 6-continued

| SEQ ID NO: | SEQUENCE |
|---|---|
| 44 | APGPSAPSHRSLPSRAFG |
| 45 | PRNSIHFLHPLLVAPLGA |
| 46 | MPSLSGVLQVRYLSPPDL |
| 47 | SPQYPSPLTLTLPPHPSL |
| 48 | NPSLNPPSYLHRAPSRIS |
| 49 | LPWRTSLLPSLPLRRRP |
| 50 | PPLFAKGPVGLLSRSFPP |
| 51 | VPPAPVVSLRSAHARPPY |
| 52 | LRPTPPRVRSYTCCPTP- |
| 53 | PNVAHVLPLLTVPWDNLR |
| 54 | CNPLLPLCARSPAVRTFP |

(S) is optional in sequences 17 to 20. Another linker may be peptide sequence GS.

Examples of rigid linkers include the peptide sequences GAPAPAAPAPA (SEQ ID NO: 69), PPPP (SEQ ID NO: 70) and PPP.

TABLE 7

| SEQ ID NO: | SEQUENCE |
|---|---|
| 55 | DLCLRDWGCLW |
| 56 | DICLPRWGCLW |
| 57 | MEDICLPRWGCLWGD |
| 58 | QRLMEDICLPRWGCLWEDDE |
| 59 | QGLIGDICLPRWGCLWGRSV |
| 60 | QGLIGDICLPRWGCLWGRSVK |
| 61 | EDICLPRWGCLWEDD |
| 62 | RLMEDICLPRWGCLWEDD |
| 63 | MEDICLPRWGCLWEDD |
| 64 | MEDICLPRWGCLWED |
| 65 | RLMEDICLARWGCLWEDD |
| 66 | EVRSFCTRWPAEKSCKPLRG |
| 67 | RAPESFVCYWETICFERSEQ |
| 68 | EMCYFPGICWM |

In one aspect, there is provided a method of producing a bispecific protein complex of the present disclosure, comprising the steps of:
(a) producing a first fusion protein (A-X), comprising a first protein (A), attached to a first binding partner (X) of a binding pair;
(b) producing a second fusion protein (B-Y), comprising a second protein (B), attached to a second binding partner (Y) of a binding pair; and
(c) mixing the first (A-X) and second fusion proteins (B-Y) prepared in step a) and b) together.

Typically the mixing of A-X and B-Y in step (c) is in a 1:1 molar ratio.

In one embodiment each fusion proteins employed in the complexes of the present disclosure are produced by expression in a host cell or host cells in an expression experiment.

In one aspect, there is provided a method of preparing a bispecific protein complex of the present disclosure, comprising the steps of:
(a) expressing a first fusion protein (A-X), comprising a first protein (A), attached to a first binding partner (X) of a binding pair;
(b) expressing a second fusion protein (B-Y), comprising a second protein (B), attached to a second binding partner (Y) of a binding pair;
wherein fusion protein A-X and B-Y are expressed from the same host cell or distinct host cells.

Distinct host cells as employed herein refers to individual cells, including cells of the same type (even same clonal type).

In one embodiment the expression is transient expression. The use of transient expression is highly advantageous when combined with the ability to generate bispecific complexes without recourse to purification. This results in a rapid method to generate bispecific protein complexes as transient transfection is much simpler and less resource intensive than stable transfection.

In one embodiment the expression is stable expression i.e. wherein the DNA encoding the fusion protein in question is stably integrated into the host cell genome.

In one embodiment the fusion proteins of the present disclosure are mixed in an aqueous environment, for example one fusion protein may be bound to a solid surface such as a bead or a plate and the other fusion protein can be introduced thereto in an aqueous solution/suspension. The solid phase allows excess components and reagents to be washed away readily. In one embodiment neither fusion is attached a solid phase and are simply mixed in a liquid/solution/medium. Thus in one embodiment A-X and B-Y are mixed as free proteins in an aqueous media.

Advantageously, the method of the present disclosure can be employed to prepare complexes formed between heterogenous pairs (i.e. between the first fusion protein [A-X] and second fusion protein [B-Y]) wherein interactions between homogenous pairs (i.e. between two first fusion proteins [A-X] or two second fusion proteins [B-Y]) are minimised. Thus the present method allows large numbers of bispecific protein complexes to be prepared, with minimal or no contamination with homodimeric complexes. An advantage of the constructs and method of the present disclosure is that the ratio of A-X to B-Y is controlled by the properties of the A-X and B-Y and in particular a molar ratio of 1:1 can be achieved. This element of control is a significant improvement over the certain prior art methods.

If present constant region domains of a bispecific antibody complex or antibody molecule of the present disclosure, if present, may be selected having regard to the proposed function of the complex or antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., 1993, Molecular Immunology, 1993, 30:105-108 may be used. Accordingly, in the embodiment where the antibody is an IgG4 antibody, the antibody may include the mutation S241P.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

The present disclosure also provides a composition comprising one or more bispecific protein complexes as described above, wherein the composition predominantly comprises heterodimeric bispecific complexes according to the present disclosure, for example with minimal or no contamination with homodimeric complexes.

In one embodiment, at least 60%, at least 65%, at least 70%, at least 75%, at least 80%, at least 90%, or at least 95% of the fusion proteins in the composition are in a bispecific protein complex form.

In one embodiment, at least 60% of the fusion proteins in the composition are in a bispecific protein complex form.

In one embodiment the complexes formed require one purification step, for example column chromatography.

In one embodiment the method further comprises at least one purification step, for example after expression of a fusion protein according to the present disclosure and before mixing the fusion proteins.

In one aspect the present disclosure relates to a fusion protein, a heterodimerically-tethered bispecific protein complex, a composition comprising a fusion protein or said bispecific protein complex, a multiple, array, library as defined herein.

In one embodiment, the bispecific protein complex is in solution or suspension.

In one embodiment, the bispecific protein complexes are fixed on a solid substrate surface.

In one embodiment, the multiplex is in the form of an array, for example in a microplate, such as a 96 or 384 well plate. Such arrays can be readily implemented in screening assays to identify bispecific protein complexes with desired functionality.

In another embodiment, the bispecific protein complexes are conjugated to beads.

A fusion protein as defined above is a component of the bispecific protein complex according to the present disclosure. In one aspect, the present disclosure relates to a fusion protein described herein.

In one embodiment there is provided a fusion protein obtained or obtainable for a method of the present disclosure.

In one embodiment there is provided an bispecific antibody complex obtained or obtainable from a method of the present disclosure The present disclosure also extends to a kit, for example comprising A-X and B-Y in a complexed or uncomplexed form, for use in the method of the present disclosure.

In another embodiment, the kit further comprises instructions for use.

In yet another embodiment, the kit further comprises one or more reagents for performing one or more functional assays.

In a further aspect, there is provided a nucleotide sequence, for example a DNA sequence encoding a fusion protein and/or a bispecific protein complex as defined above.

In one embodiment, there is provided a nucleotide sequence, for example a DNA sequence encoding a bispecific protein complex according to the present disclosure.

In one embodiment there is provided a nucleotide sequence, for example a DNA sequence encoding a bispecific or multispecific antibody molecule according to the present disclosure.

The disclosure herein also extends to a vector comprising a nucleotide sequence as defined above including a vector suitable for use in vivo, such as for expression of A-X in an effector cell, under the control of a suitable promoter.

The term "vector" as used herein refers to a nucleic acid molecule capable of transporting another nucleic acid to which it has been linked. An example of a vector is a "plasmid," which is a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell, where they are subsequently replicated along with the host genome. In the present specification, the terms "plasmid" and "vector" may be used interchangeably as a plasmid is the most commonly used form of vector.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

The term "selectable marker" as used herein refers to a protein whose expression allows one to identify cells that have been transformed or transfected with a vector containing the marker gene. A wide range of selection markers are known in the art. For example, typically the selectable marker gene confers resistance to drugs, such as G418, hygromycin or methotrexate, on a host cell into which the vector has been introduced. The selectable marker can also be a visually identifiable marker such as a fluorescent marker for example. Examples of fluorescent markers include rhodamine, FITC, TRITC, Alexa Fluors and various conjugates thereof.

Also provided is a host cell comprising one or more cloning or expression vectors comprising one or more DNA sequences encoding an antibody of the present disclosure. Any suitable host cell/vector system may be used for expression of the DNA sequences encoding the antibody molecule of the present disclosure. Bacterial, for example E. coli, and other microbial systems may be used or eukaryotic, for example mammalian, host cell expression systems may also be used. Suitable mammalian host cells include CHO, myeloma or hybridoma cells.

The present disclosure also provides a process for the production of a fusion protein according to the present disclosure comprising culturing a host cell containing a vector of the present disclosure under conditions suitable for leading to expression of protein from DNA encoding the molecule of the present disclosure, and isolating the molecule.

The bispecific antibody complexes of the present disclosure may for example be conjugated to a fluorescent marker which facilitates the detection of bound antibody-antigen complexes. Such bispecific antibody complexes can be used for immunofluorescence microscopy.

Alternatively, the bispecific antibody complexes may also be used for western blotting or ELISA.

In one embodiment, there is provided a process for purifying an antibody (in particular an antibody or fragment according to the invention).

In one embodiment, there is provided a process for purifying a fusion protein or bispecific protein complex according the present disclosure comprising the steps: performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

"Purified form" as used supra is intended to refer to at least 90% purity, such as 91, 92, 93, 94, 95, 96, 97, 98, 99% w/w or more pure.

In the context of this specification "comprising" is to be interpreted as "including".

Aspects of the disclosure comprising certain elements are also intended to extend to alternative embodiments "consisting" or "consisting essentially" of the relevant elements.

Positive embodiments employed herein may serve basis for the excluding certain aspects of the disclosure.

Disclosures in the context of the method relating to the bispecific complexes apply equally to the complexes per se and vice versa.

REFERENCES

1. Ribosome display efficiently selects and evolves high-affinity antibodies in vitro from immune libraries. Hanes J, Jermutus L, Weber-Bornhauser S, Bosshard H R, Plückthun A. (1998) Proc. Natl. Acad. Sci. U.S.A. 95, 14130-14135
2. Directed in Vitro Evolution and Crystallographic Analysis of a Peptide-binding Single Chain Antibody Fragment (scFv) with Low Picomolar Affinity. Zhand C, Spinelli S, Luginbuhl B, Amstutz P, Cambillau C, Pluckthun A. (2004) J. Biol. Chem. 279, 18870-18877
3. Antigen recognition by conformational selection. Berger C, Weber-Bornhauser S, Eggenberger Y, Hanes J, Pluckthun A, Bosshard H. R. (1999) F.E.B.S. Letters 450, 149-153

EXAMPLES

Figure 2:
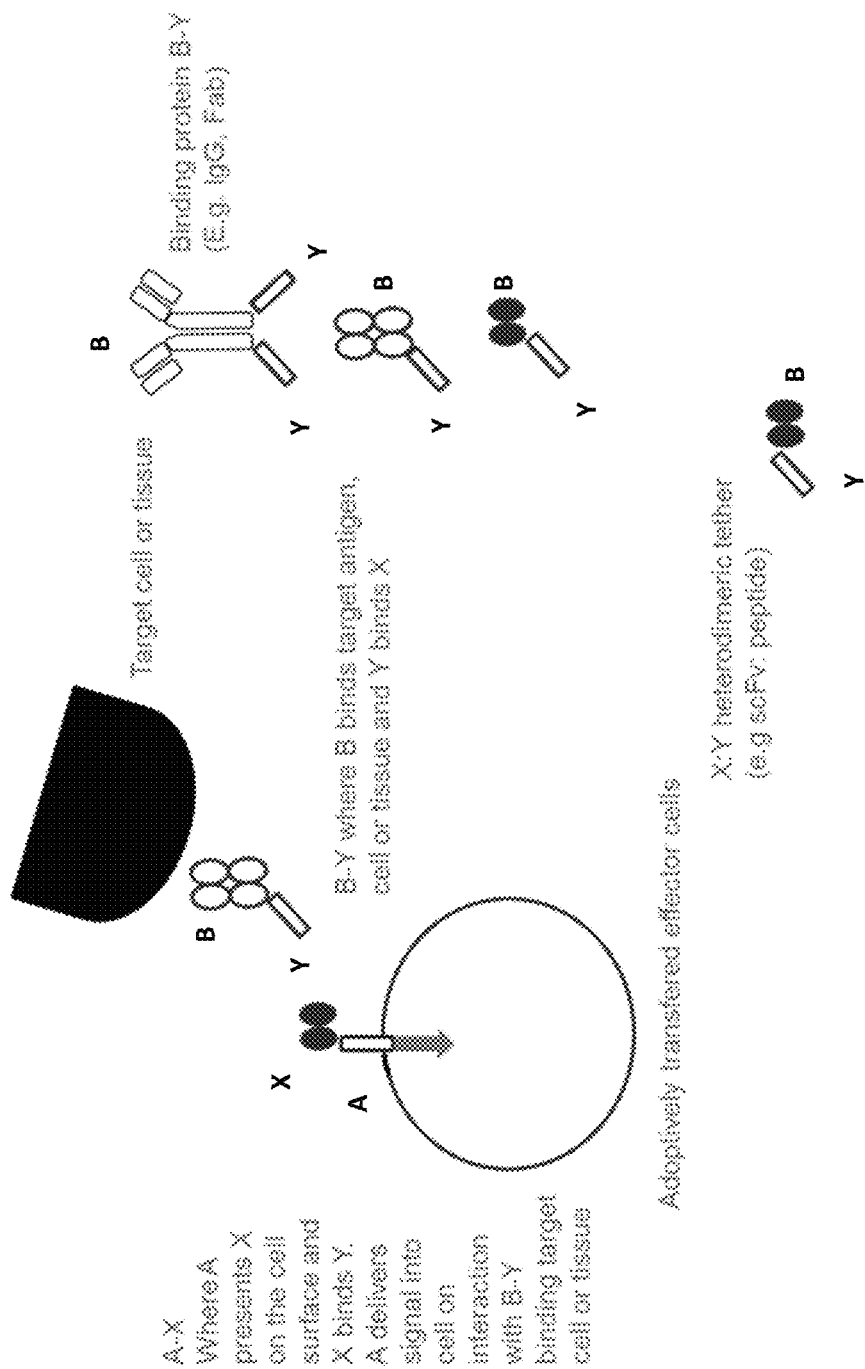
FIG. 2 shows an A-X fusion protein expressed on the surface of a cell (wherein A is a surface protein which is connected to an intra-cellular signalling domain [also referred to herein as a chimeric receptor] and X is a scFv) and B is a Fab specific to an epitope on the surface of a target cell or tissue and Y is a peptide specific to X. Alternative formats for B-Y are also provided.
Figure 4:
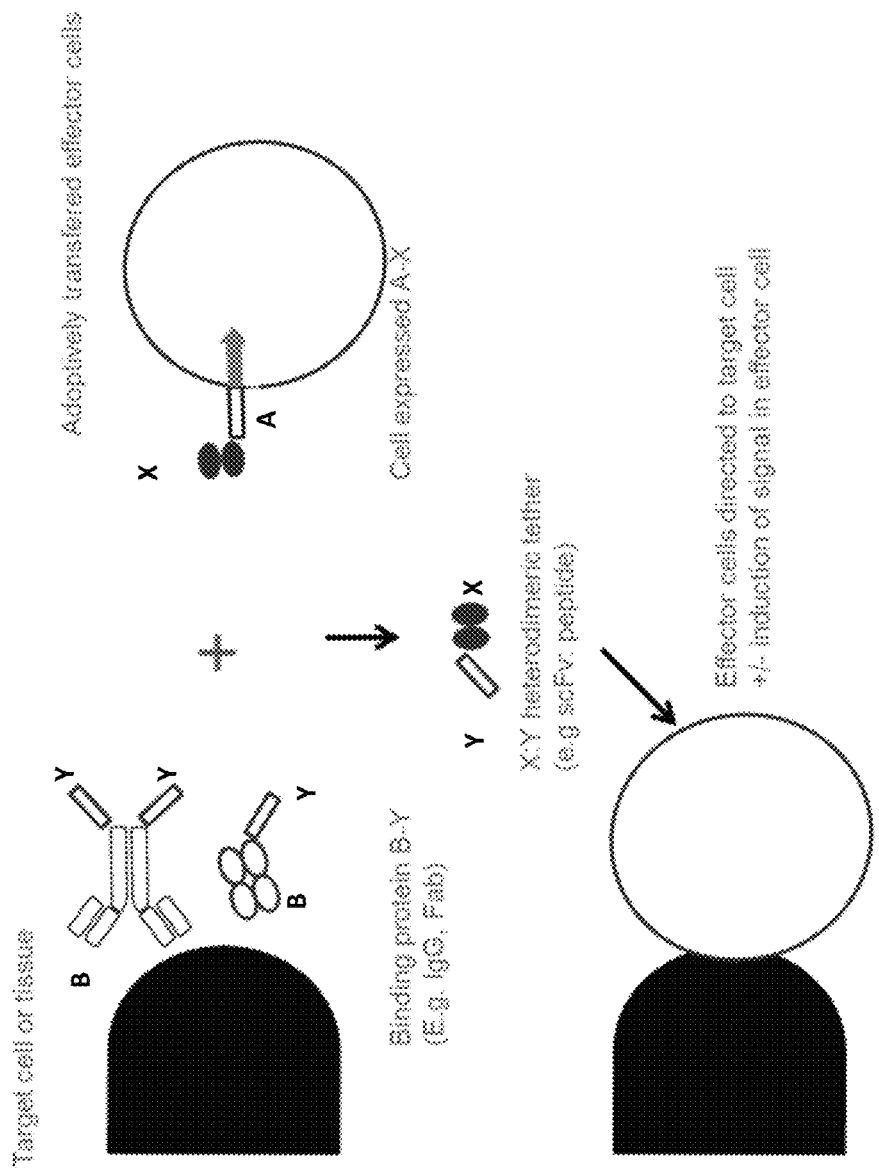
FIG. 4 shows an A-X fusion protein expressed on the surface of a cell (wherein A is a surface protein which is connected to an intra-cellular signalling domain [also referred to herein as a chimeric receptor] and X is a scFv) and B is a Fab specific to surface antigen on the target cell and Y is a peptide. Alternatively B is a full length antibody comprising two Y peptides.

Example 1: Directing Engrafted T Cells or NK Cells to Kill Cancer Cells (Illustrated in FIGS. 2 and 4)

In this example A-X, is a fusion of X (a scFv (52SR4 having amino acid sequence such as that shown in SEQ ID NOs: 99 or 100) with binding specificity for Y (GCN4) with A comprising a spacer region, a transmembrane region and a signalling region capable of delivering an activating signal to T cells or NK cells. The components of A could be those commonly used in the chimeric antigen receptors used to direct T cells to cancer cells (Nat Revs Drug Discovery 2015: vol 14 p 499-509) and having amino acid sequence as shown in X-A SEQ ID NO: 109-116). B-Y is a fusion of B, an antibody or antibody fragment or derivative specific for the cancer antigen fused to Y (GCN4 peptide having an amino acid sequence as shown in SEQ ID NO: 76-98).

The A-X fusion polynucleotide sequence is delivered to and protein expressed on T or NK cells for infusion into patients. A-X can be pre-complexed with B-Y before infusion or cells expressing A-X can be infused and B-Y delivered to the patient subsequently to form the A-X:Y-B complex in vivo.

The time of delivery and half-life of B-Y can be tuned to reduce side effects of cell infusion & rapid target lysis. Targeting can be stopped by withdrawal of administration of B-Y.

During the course of disease & treatment the specificity of B in B-Y can be changed. This could facilitate the re-direction of engrafted cells to a second tumour antigen in the case of tumour cell escape or target the engrafted cells for destruction to terminate treatment.

This modular ability to deliver engrafted cell specificity has advantages over receptors utilising CD16 to capture of IgG specificities (Cancer Res 2013 74 (1) 93-103) as these could bind to autoantibodies in vivo and hence target engrafted T cells to self-antigens & tissues generating acute autoimmunity. The specificity of X for Y only expressed on the targeting moiety of choice would prevent this.

Example 2: Directing Engrafted T Regulatory Cells to a Selected Location to Prevent Autoimmunity (Illustrated in FIG. 1)

In this example A-X, is a fusion of X (a scFv (52SR4 having amino acid sequence such as that shown in SEQ ID NOs: 99 or 100) with binding specificity for Y (GCN4 peptide having an amino acid sequence as shown in SEQ ID NO: 76-98) with A comprising a spacer region, a transmembrane region to facilitate cell surface expression of X. X-A having amino acid sequence such as that shown in SEQ ID NOs: 105-109. B-Y is a fusion of B, an antibody or antibody fragment or derivative specific for a tissue specific antigen fused to Y (GCN4).

The A-X fusion polynucleotide sequence is delivered to and protein expressed on T regulatory cells for infusion into patients. A-X can be pre-complexed with B-Y before infusion or cells expressing A-X can be infused and B-Y delivered to the patient subsequently to form the A-X:Y-B complex in vivo.

The time of delivery and half-life of B-Y can be tuned to reduce side effects of cell infusion & rapid target lysis. During the course of disease & treatment the specificity of B in B-Y can be changed. This could facilitate the redirection of engrafted cells to a different site or target the engrafted cells for destruction to terminate treatment.

Example 3: Directing Haemopoetic Stem Cells to a Selected Location to Expand & Differentiate for Treatment of a Wide Range of Diseases (Illustrated in FIG. 1)

In this example A-X, is a fusion of X (a scFv (52SR4 having amino acid sequence such as that shown in SEQ ID NOs: 99 or 100) with binding specificity for Y (GCN4 peptide having an amino acid sequence as shown in SEQ ID NO: 76-98) with A comprising a spacer region, a transmembrane region to facilitate cell surface expression of X. X-A having amino acid sequence such as that shown in SEQ ID NOs: 105-109. B-Y is a fusion of B, an antibody or antibody fragment or derivative specific for a tissue specific antigen fused to Y (GCN4).

The A-X fusion polynucleotide sequence is delivered to and expressed on haemopoetic stem cells for infusion into patients. A-X can be pre-complexed with B-Y before infusion or cells expressing A-X can be infused and B-Y delivered to the patient subsequently to form the A-X:Y-B complex in vivo.

The time of delivery and half-life of B-Y can be tuned to reduce side effects of cell infusion & rapid target lysis. During the course of disease & treatment the specificity of B in B-Y can be changed. This could facilitate the redirection of engrafted cells to a different site or target the engrafted cells for destruction to terminate treatment.

Figure 3:
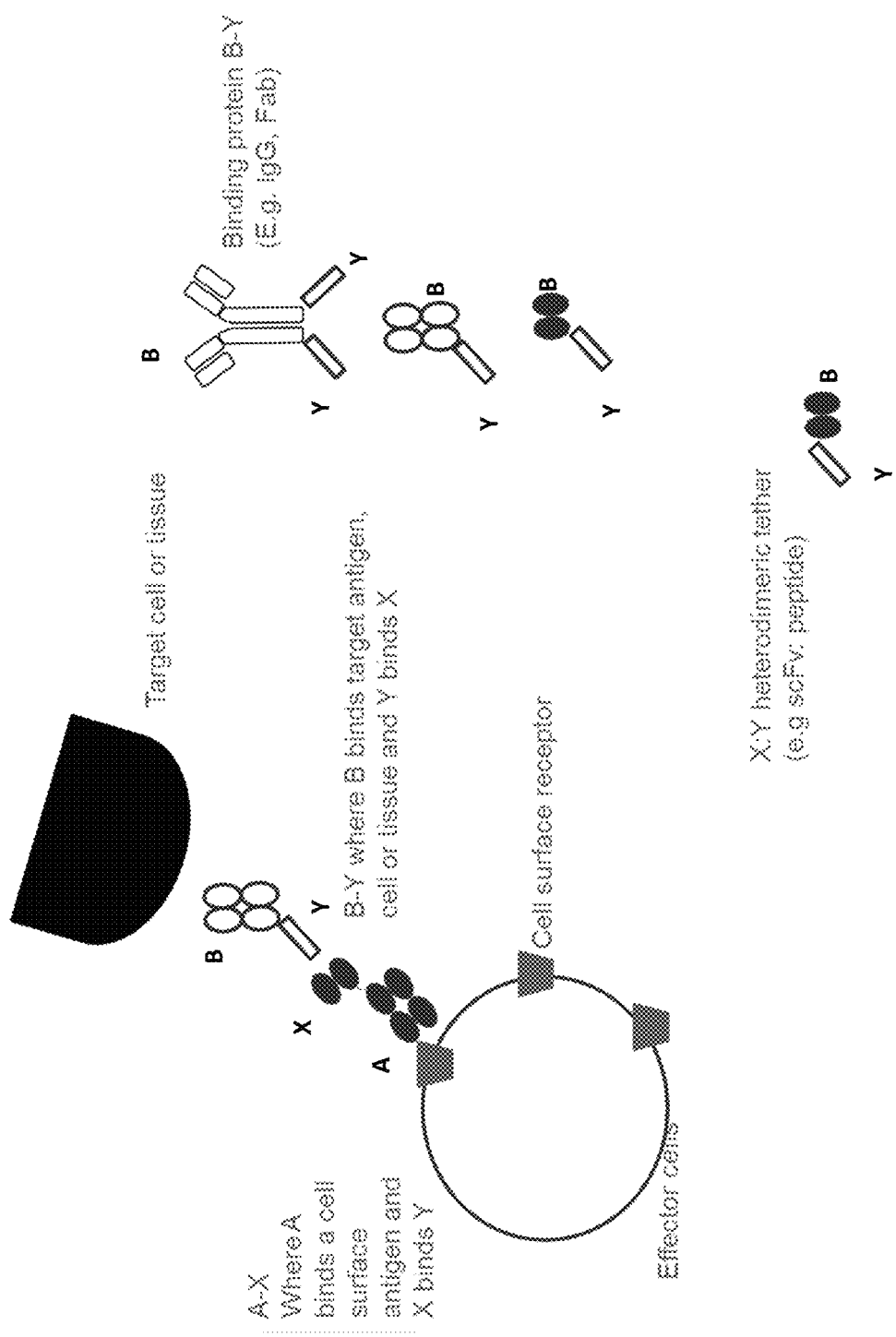
FIG. 3 shows A-X wherein in A is a Fab or Fab' specific to an antigen expressed on the surface of the cell (an effector cell) and X is a single chain Fv specific to Y. B is a Fab specific to an epitope on the surface of a target cell or tissue and Y is a peptide specific to X. Alternative formats for B-Y are also shown.
Figure 5:
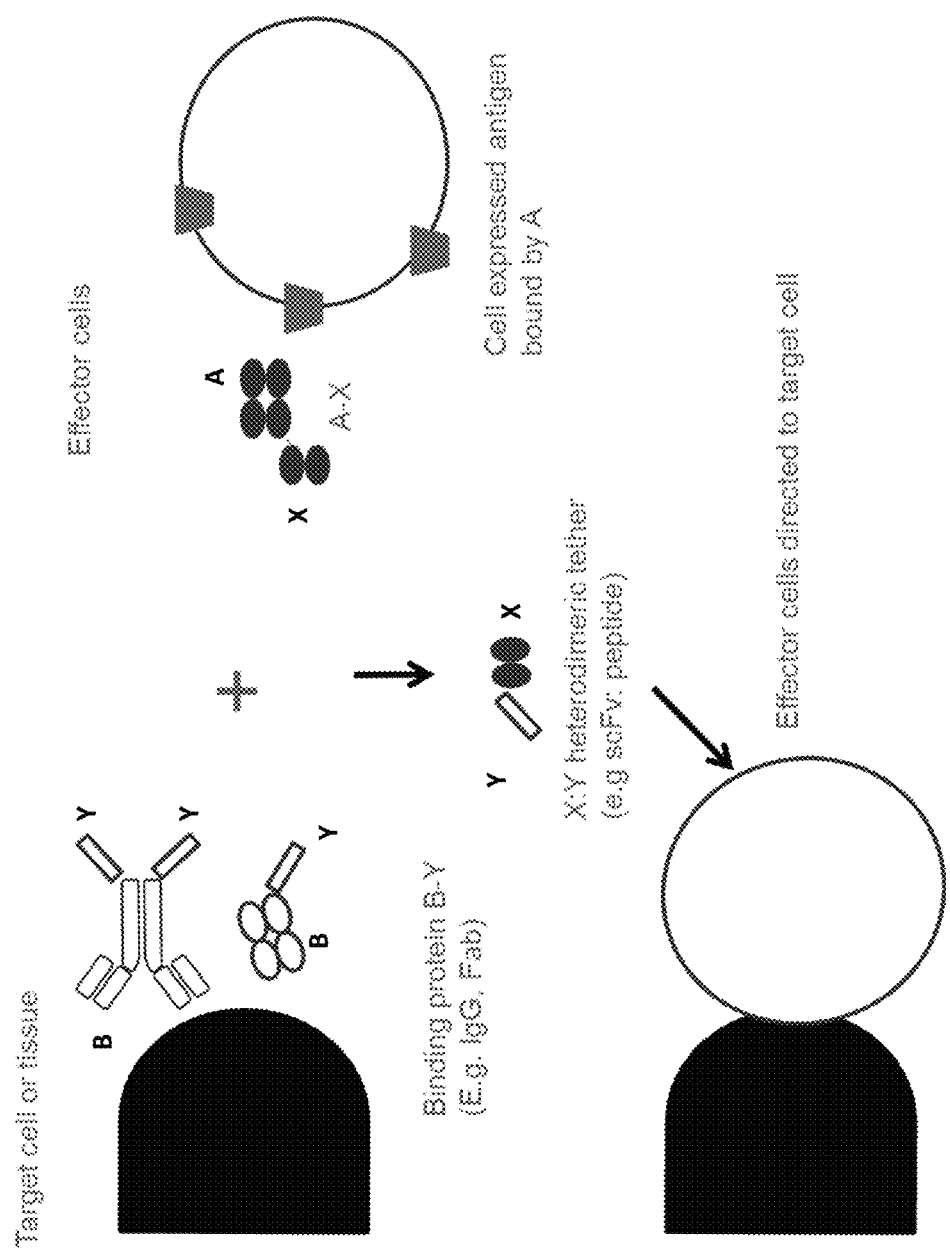
FIG. 5 shows A-X wherein in A is a Fab or Fab' specific to an antigen expressed on the surface of the cell (an effector cell) and X is a scFv) and B is a Fab specific to surface antigen on the target cell and Y is a peptide. Alternatively B is a full length antibody comprising two Y peptides.

Example 4: Directing T Cells or NK Cells In Vivo to Kill Cancer Cells (Illustrated in FIGS. 3 and 5)

In this example A-X, is a fusion of X (a scFv (52SR4) with binding specificity for Y (GCN4) with A comprising an antibody or antibody fragment or derivative specific to T cells or NK cells. B-Y is a fusion of B, an antibody or antibody fragment or derivative specific for a tissue specific antigen fused to Y (GCN4).

A-X can be pre-complexed with B-Y before delivery or B-Y can delivered to the patient subsequently to form the A-X:Y-B complex in vivo. This would allow pre-loading of either effector or target cells whichever proved clinically of most benefit.

The time of delivery and half-life of either or both A-X and B-Y can be tuned to complement treatment.

Example 5: Directing T Regulatory Cells In Vivo to a Selected Location to Prevent Autoimmunity (Illustrated in FIGS. 3 and 5)

In this example A-X, is a fusion of X (a scFv (52SR4) with binding specificity for Y (GCN4) with A comprising an antibody or antibody fragment or derivative specific to T regulatory cells. B-Y is a fusion of B, an antibody or antibody fragment or derivative specific for a tissue specific antigen fused to Y (GCN4).

A-X can be pre-complexed with B-Y before delivery or B-Y can delivered to the patient subsequently to form the A-X:Y-B complex in vivo. This would allow pre-loading of either effector or target cells whichever proved clinically of most benefit.

The time of delivery and half-life of either or both A-X and B-Y can be tuned to complement treatment.

Example 6: Directing Haemopoetic Stem Cells to a Selected Location to Expand & Differentiate for Treatment of a Wide Range of Diseases (Illustrated in FIGS. 3 and 5)

In this example A-X, is a fusion of X (a scFv (52SR4) with binding specificity for Y (GCN4) with A comprising an antibody or antibody fragment or derivative specific to haemopoetic stem cells. B-Y is a fusion of B, an antibody or antibody fragment or derivative specific for a tissue specific antigen fused to Y (GCN4).

A-X can be pre-complexed with B-Y before delivery or B-Y can delivered to the patient subsequently to form the A-X:Y-B complex in vivo. This would allow pre-loading of either effector or target cells whichever proved clinically of most benefit.

The time of delivery and half-life of either or both A-X and B-Y can be tuned to complement treatment.

Example 7: The Use of the Complex of A-X:Y-B for Screening

The formation of the complex of A-X:Y-B for screening can be used to generate large numbers of different B molecules in B-X and different A molecules in A-Y for screening the optimal combination of molecules in in vitro or in vivo assays mimicking the clinical scenarios of examples 1 to 6. This would facilitate selection of optimal A and B molecules in a bispecific format for cell direction and function in vivo.

Example 8: Utilising Cells that can Cross the Blood Brain Barrier to Direct Antibody Specificities to a Central Nervous System (CNS) Target for Treatment of Neurodegenerative and/or Neuroinflammatory Diseases (Illustrated in FIGS. 3 and 5)

In this example A-X, is a fusion of X (a scFv (52SR4) with binding specificity for Y (GCN4) with A comprising an antibody or antibody fragment or derivative specific to effector cells that are able to transgress the blood brain barrier or A is a protein that facilitates expression of X on the surface of effector cells able to transgress the blood brain barrier. These effector cells act to carry a cargo of B-Y. B-Y is a fusion of B, an antibody or antibody fragment or derivative specific for a CNS expressed antigen fused to Y (GCN4). The binding of B to its target antigen in the CNS provides therapeutic benefit.

A-X can be pre-complexed with B-Y before delivery or B-Y can delivered to the patient subsequently to form the A-X:Y-B complex in vivo. This would allow optimal loading of guidance cells for clinically benefit.

The time of delivery and half-life of either or both A-X and B-Y can be tuned to complement treatment.

The invention claimed is:

1. A method of identifying a bispecific protein complex that destroys a target cell or modulates a function of a target cell, comprising
   (a) generating fusion proteins of formula A-X and B-Y and heterodimerically-tethered bispecific protein complexes of formula A-X:Y-B;
   (b) contacting a population of cells comprising an effector cell and a target cell with:
      i. a combination of the fusion proteins A-X and B-Y in an uncomplexed form, or
      ii. A-X:Y-B in a heterodimerically-tethered bispecific protein complex form; and
   (c) monitoring the population of cells for destruction of the target cell or modulation of the function of the target cell, thereby identifying the bispecific protein complex that destroys the target cell or modulates the function of the target cell,
   wherein
   X:Y is a heterodimeric-tether;
   : is a binding interaction between X and Y;
   A is a first protein component of the bispecific protein complex selected from an antibody or binding fragment thereof, and a protein, wherein A specifically binds a protein expressed on the surface of an effector cell;
   B is a second protein component of the bispecific protein complex selected from an antibody or binding fragment or an antigen, wherein B specifically binds a target cell;
   X is a scFv and Y is a peptide GCN4 or a fragment thereof (SEQ ID NO: 1 or amino acids 1-38 of SEQ ID NO: 1 or SEQ ID NO: 76 to 98), or
   X is a peptide GCN4 or a fragment thereof (SEQ ID NO: 1 or amino acids 1-38 of SEQ ID NO: 1 or SEQ ID NO: 76 to 98) and Y is a scFv; and
      wherein X or Y is specific to the peptide GCN4 or a fragment thereof (SEQ ID NO: 1 or amino acids 1-38 of SEQ ID NO: 1 or SEQ ID NO: 76 to 98), and wherein the scFv is 52SR4 (SEQ ID NO: 3 or amino acids 1-243 of SEQ ID NO: 3 or SEQ ID NO.99-100).

2. The method according to claim 1, wherein X or Y is an antigen with no corresponding mammalian sequence.

3. The method according to claim 1, wherein a binding affinity between X and Y is 5 nM, 900, 800, 700, 600, 500, 400 or 300 pM.

4. The method according to claim 1 where the bispecific protein complex comprises no more than two scFv and/or at least one Fab or Fab' fragment.

5. The method according to claim 1,
   i. wherein the effector cell is a cell capable of a cellular response, wherein the cellular response is phagocytosis, cytotoxicity, generating an antibody, release of a soluble molecule, or a combination thereof; and/or
   ii. wherein A is independently selected from the group consisting of a full length antibody, a Fab fragment, a Fab' fragment, a sdAb, a scFv, and an antigen.

6. The method according to claim 1,
   wherein the effector cell is selected from the group consisting of a B cell, T cell, an NK cell, monocyte, macrophage, dendritic cell, mast cell, neutrophil, eosinophil and basophil.

7. The method according to claim 6, wherein the effector cell is a B cell, wherein the B cell comprises a marker that is in a constant region of an antibody light chain or a constant region of an antibody heavy chain, expressed as part of an immunoglobulin on the surface of the cell.

8. The method according to claim 1, wherein B is a full length antibody, a Fab fragment, a Fab' fragment, a sdAb, or a scFv.

9. The method according to claim 1, wherein the effector cell transgresses the blood brain barrier (BBB), wherein B binds a central nervous system expressed target.

10. The method according to claim 1, wherein B binds a cell surface marker on the target cell, wherein the cell surface marker is:
    i. a tumor antigen selected from erbB-2, CEA, NCAM, GD2, CD33, CD44, CD70, EpCAM, CD19, CD20, KDR, and Tag-72; or
    ii. a HER receptor; or
    iii. a B cell marker or T cell marker.

11. The method according to claim 1, wherein:
    i. X is fused to the N-terminal or C-terminal of A; or
    ii. X and/or Y is fused to the C-terminal of the heavy chain of an antibody or an antigen binding fragment thereof; or
    iii. Y is fused to the C-terminal of B.

12. The method of claim 1, wherein A is an antibody, an antigen binding fragment thereof or an antigen, wherein B is an antibody or an antigen binding fragment or a protein ligand.

13. The method of claim 6, wherein the protein expressed on the surface of the effector cell is CD45, CD2, CD3, CD4, CD5, CD7, CD8, CD11b, CD11c, CD13, CD14, CD15, CD16, CD19, CD20, CD23, CD25, CD27, CD33, CD38, CD56, CD57, CD64, CD80, CD83, CD86, CD123, CD127, CD137, CD138, CD196, CD209, HLA-DR, Lin- 1 to -3, or a combination thereof.

14. The method of claim 6, wherein the effector cell is a B cell comprising a marker, and the B cell marker is selected from the group consisting of CD19, CD20, CD21, CD22, CD23, CD24, CD27, CD35, CD38, CD40, CD45, CD43, CD81, CD138, CXCR4, BCMA and IL-6R.

15. The method of claim 6, wherein the effector cell is a T cell comprising a marker and the T cell marker is selected from the group consisting of CD2, CD3, CD4, CD5, CD6, CD7, CD8, CD25, CD127 CD196 (CCR6), CD197 (CCR7), CD62L, CD69 and CD45.

16. The method of claim 5, wherein the cellular response is release of an immunoglobulin, a cytokine, a chemokine, or a combination thereof.

* * * * *

SEQUENCE LISTING

<160> NUMBER OF SEQ ID NOS: 116

<210> SEQ ID NO 1
<211> LENGTH: 44
<212> TYPE: PRT
<213> ORGANISM: Artificial Sequence
<220> FEATURE:
<223> OTHER INFORMATION: CN4(7P14P) sequence

<400> SEQUENCE: 1

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Lys Leu Val Gly Glu Arg His His His His His His
        35                  40

<210> SEQ ID NO 2
<211> LENGTH: 132
<212> TYPE: DNA
<213> ORGANISM: Artificial Sequence
<220> FEATURE:
<223> OTHER INFORMATION: DNA encoding

<400> SEQUENCE: 2
gctagcggag gcggaagaat gaaacaactt gaacccaagg ttgaagaatt gcttccgaaa      60
aattatcact ggaaaatga ggttgccaga ttaaagaaat tagttggcga acgccatcac     120
catcaccatc ac                                                        132

<210> SEQ ID NO 3
<211> LENGTH: 262
<212> TYPE: PRT
<213> ORGANISM: Artificial Sequence
<220> FEATURE:
<223> OTHER INFORMATION: 52SR4 ds scFv sequence

<400> SEQUENCE: 3

Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Ser Gly Gly Gly Ser Gly Gly Gly
        115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

```
Trp Leu Gly Val Ile Trp Gly Asp Gly Ile Thr Asp Tyr Asn Ser Ala
                180                 185                 190

Leu Lys Ser Arg Leu Ser Val Thr Lys Asp Asn Ser Lys Ser Gln Val
            195                 200                 205

Phe Leu Lys Met Asn Ser Leu Gln Ser Gly Asp Ser Ala Arg Tyr Tyr
        210                 215                 220

Cys Val Thr Gly Leu Phe Asp Tyr Trp Gly Gln Gly Thr Thr Leu Thr
225                 230                 235                 240

Val Ser Ser Ala Ala Ala His His His His His His Glu Gln Lys Leu
                245                 250                 255

Ile Ser Glu Glu Asp Leu
            260

<210> SEQ ID NO 4
<211> LENGTH: 792
<212> TYPE: DNA
<213> ORGANISM: Artificial Sequence
<220> FEATURE:
<223> OTHER INFORMATION: DNA encoding

<400> SEQUENCE: 4
gatgcggtgg tgacccagga aagcgcgctg accagcagcc cgggcgaaac cgtgaccctg      60
acctgccgca gcagcaccgg cgcggtgacc accagcaact atgcgagctg ggtgcaggaa     120
aaaccggatc atctgtttac cggcctgatt ggcggcacca caaccgcgc gccgggcgtg     180 ccggcgcgct ttagcggcag cctgattggc gataaagcgg cgctgaccat taccggcgcg     240
cagaccgaag atgaagcgat ttatttttgc gtgctgtggt atagcgacca ttgggtgttt     300
ggctgcggca ccaaactgac cgtgctgggt ggaggcggtg gctcaggcgg aggtggctca     360
ggcggtggcg ggtctggcgg cggcggcagc gatgtgcagc tgcagcagag cggcccgggc     420
ctggtggcgc cgagccagag cctgagcatt acctgcaccg tgagcggctt tctcctgacc     480
gattatggcg tgaactgggt cgccagagc ccgggcaaat gcctggaatg gctgggcgtg     540
atttggggcg atggcattac cgattataac agcgcgctga aaagccgcct gagcgtgacc     600
aaagataaca gcaaaagcca ggtgtttctg aaaatgaaca gcctgcagag cggcgatagc     660
gcgcgctatt attgcgtgac cggcctgttt gattattggg gccagggcac caccctgacc     720
gtgagcagcg cggccgccca tcaccatcac catcacgaac agaaactgat tagcgaagaa     780
gatctgtaat ag                                                          792

<210> SEQ ID NO 5
<211> LENGTH: 8
<212> TYPE: PRT
<213> ORGANISM: Artificial Sequence
<220> FEATURE:
<223> OTHER INFORMATION: FLEXIBLE PEPTIDE LINKER

<400> SEQUENCE: 5

Asp Lys Thr His Thr Cys Ala Ala
1               5

<210> SEQ ID NO 6
<211> LENGTH: 11
<212> TYPE: PRT
<213> ORGANISM: Artificial Sequence
<220> FEATURE:
<223> OTHER INFORMATION: FLEXIBLE PEPTIDE LINKER

<400> SEQUENCE: 6
```

```
Asp Lys Thr His Thr Cys Pro Pro Cys Pro Ala
1               5                   10
```

<210> SEQ ID NO 7
<211> LENGTH: 18
<212> TYPE: PRT
<213> ORGANISM: Artificial Sequence
<220> FEATURE:
<223> OTHER INFORMATION: FLEXIBLE PEPTIDE LINKER

<400> SEQUENCE: 7

```
Asp Lys Thr His Thr Cys Pro Pro Cys Pro Ala Thr Cys Pro Pro Cys
1               5                   10                  15

Pro Ala
```

<210> SEQ ID NO 8
<211> LENGTH: 25
<212> TYPE: PRT
<213> ORGANISM: Artificial Sequence
<220> FEATURE:
<223> OTHER INFORMATION: FLEXIBLE PEPTIDE LINKER

<400> SEQUENCE: 8

```
Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25
```

<210> SEQ ID NO 9
<211> LENGTH: 30
<212> TYPE: PRT
<213> ORGANISM: Artificial Sequence
<220> FEATURE:
<223> OTHER INFORMATION: FLEXIBLE PEPTIDE LINKER

<400> SEQUENCE: 9

```
Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30
```

<210> SEQ ID NO 10
<211> LENGTH: 31
<212> TYPE: PRT
<213> ORGANISM: Artificial Sequence
<220> FEATURE:
<223> OTHER INFORMATION: FLEXIBLE PEPTIDE LINKER

<400> SEQUENCE: 10

```
Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30
```

<210> SEQ ID NO 11
<211> LENGTH: 15
<212> TYPE: PRT
<213> ORGANISM: Artificial Sequence
<220> FEATURE:
<223> OTHER INFORMATION: FLEXIBLE PEPTIDE LINKER

<400> SEQUENCE: 11

```
Asp Lys Thr His Thr Cys Cys Val Glu Cys Pro Pro Cys Pro Ala
1               5                   10                  15
```

```
<210> SEQ ID NO 12
<211> LENGTH: 26
<212> TYPE: PRT
<213> ORGANISM: Artificial Sequence
<220> FEATURE:
<223> OTHER INFORMATION: FLEXIBLE PEPTIDE LINKER

<400> SEQUENCE: 12

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

<210> SEQ ID NO 13
<211> LENGTH: 11
<212> TYPE: PRT
<213> ORGANISM: Artificial Sequence
<220> FEATURE:
<223> OTHER INFORMATION: FLEXIBLE PEPTIDE LINKER

<400> SEQUENCE: 13

Asp Lys Thr His Thr Cys Pro Ser Cys Pro Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Flexible linker

<400> SEQUENCE: 14

Ser Gly Gly Gly Gly Ser Glu
1               5

<210> SEQ ID NO 15
<211> LENGTH: 6
<212> TYPE: PRT
<213> ORGANISM: Artificial Sequence
<220> FEATURE:
<223> OTHER INFORMATION: Flexible linker

<400> SEQUENCE: 15

Asp Lys Thr His Thr Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Flexible linker

<400> SEQUENCE: 16

Ser Gly Gly Gly Gly Ser
1               5

<210> SEQ ID NO 17
<211> LENGTH: 11
<212> TYPE: PRT
<213> ORGANISM: Artificial Sequence
<220> FEATURE:
<223> OTHER INFORMATION: Flexible linker

<400> SEQUENCE: 17
```

```
Ser Gly Gly Gly Gly Ser Gly Gly Gly Ser
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Flexible linker

<400> SEQUENCE: 18

Ser Gly Gly Gly Gly Ser Gly Gly Gly Gly Ser Gly Gly Gly Gly Ser
1               5                   10                  15

<210> SEQ ID NO 19
<211> LENGTH: 21
<212> TYPE: PRT
<213> ORGANISM: Artificial Sequence
<220> FEATURE:
<223> OTHER INFORMATION: Flexible linker

<400> SEQUENCE: 19

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 20
<211> LENGTH: 26
<212> TYPE: PRT
<213> ORGANISM: Artificial Sequence
<220> FEATURE:
<223> OTHER INFORMATION: Flexible linker

<400> SEQUENCE: 20

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 21
<211> LENGTH: 11
<212> TYPE: PRT
<213> ORGANISM: Artificial Sequence
<220> FEATURE:
<223> OTHER INFORMATION: Flexible linker

<400> SEQUENCE: 21

Ala Ala Ala Gly Ser Gly Gly Ala Ser Ala Ser
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Ala Ala Ala Gly Ser Gly Xaa Gly Gly Gly Ser Gly Ala Ser Ala Ser
1               5                   10                  15
```

```
<210> SEQ ID NO 23
<211> LENGTH: 21
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 23

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 24
<211> LENGTH: 26
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 24

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 25
<211> LENGTH: 31
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 25

Ala Ala Ala Gly Ser Gly Xaa Gly Gly Gly Ser Xaa Gly Gly Gly Ser
1               5                   10                  15
```

```
Xaa Gly Gly Gly Ser Xaa Gly Gly Ser Gly Ala Ser Ala Ser
            20                  25              30

<210> SEQ ID NO 26
<211> LENGTH: 13
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 26

Ala Ala Ala Gly Ser Gly Xaa Ser Gly Ala Ser Ala Ser
1               5                   10

<210> SEQ ID NO 27
<211> LENGTH: 28
<212> TYPE: PRT
<213> ORGANISM: Artificial Sequence
<220> FEATURE:
<223> OTHER INFORMATION: Flexible linker

<400> SEQUENCE: 27

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25

<210> SEQ ID NO 28
<211> LENGTH: 11
<212> TYPE: PRT
<213> ORGANISM: Artificial Sequence
<220> FEATURE:
<223> OTHER INFORMATION: Flexible linker

<400> SEQUENCE: 28

Ala Thr Thr Thr Gly Ser Ser Pro Gly Pro Thr
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Flexible linker

<400> SEQUENCE: 29

Ala Thr Thr Thr Gly Ser
1               5

<210> SEQ ID NO 30
<211> LENGTH: 13
<212> TYPE: PRT
<213> ORGANISM: Artificial Sequence
<220> FEATURE:
<223> OTHER INFORMATION: Flexible linker

<400> SEQUENCE: 30

Ala Ala Ala Ala Ala Ala Ala Ala Ala Ala Ala Ala Ala
1               5                   10

<210> SEQ ID NO 31
<211> LENGTH: 21
```

```
<212> TYPE: PRT
<213> ORGANISM: Artificial Sequence
<220> FEATURE:
<223> OTHER INFORMATION: Flexible linker

<400> SEQUENCE: 31

Glu Pro Ser Gly Pro Ile Ser Thr Ile Asn Ser Pro Pro Ser Lys Glu
1               5                   10                  15

Ser His Lys Ser Pro
            20

<210> SEQ ID NO 32
<211> LENGTH: 15
<212> TYPE: PRT
<213> ORGANISM: Artificial Sequence
<220> FEATURE:
<223> OTHER INFORMATION: Flexible linker

<400> SEQUENCE: 32

Gly Thr Val Ala Ala Pro Ser Val Phe Ile Phe Pro Pro Ser Asp
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Flexible linker

<400> SEQUENCE: 33

Gly Gly Gly Gly Ile Ala Pro Ser Met Val Gly Gly Gly Gly Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Flexible linker

<400> SEQUENCE: 34

Gly Gly Gly Gly Lys Val Glu Gly Ala Gly Gly Gly Gly Gly Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Flexible linker

<400> SEQUENCE: 35

Gly Gly Gly Gly Ser Met Lys Ser His Asp Gly Gly Gly Gly Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Flexible linker

<400> SEQUENCE: 36

Gly Gly Gly Gly Asn Leu Ile Thr Ile Val Gly Gly Gly Gly Ser
1               5                   10                  15
```

-continued

```
<210> SEQ ID NO 37
<211> LENGTH: 15
<212> TYPE: PRT
<213> ORGANISM: Artificial Sequence
<220> FEATURE:
<223> OTHER INFORMATION: Flexible linker

<400> SEQUENCE: 37

Gly Gly Gly Gly Val Val Pro Ser Leu Pro Gly Gly Gly Gly Ser
1               5                   10                  15

<210> SEQ ID NO 38
<211> LENGTH: 12
<212> TYPE: PRT
<213> ORGANISM: Artificial Sequence
<220> FEATURE:
<223> OTHER INFORMATION: Flexible linker

<400> SEQUENCE: 38

Gly Gly Glu Lys Ser Ile Pro Gly Gly Gly Gly Ser
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Flexible linker

<400> SEQUENCE: 39

Arg Pro Leu Ser Tyr Arg Pro Pro Phe Pro Phe Gly Phe Pro Ser Val
1               5                   10                  15

Arg Pro

<210> SEQ ID NO 40
<211> LENGTH: 18
<212> TYPE: PRT
<213> ORGANISM: Artificial Sequence
<220> FEATURE:
<223> OTHER INFORMATION: Flexible linker

<400> SEQUENCE: 40

Tyr Pro Arg Ser Ile Tyr Ile Arg Arg Arg His Pro Ser Pro Ser Leu
1               5                   10                  15

Thr Thr

<210> SEQ ID NO 41
<211> LENGTH: 18
<212> TYPE: PRT
<213> ORGANISM: Artificial Sequence
<220> FEATURE:
<223> OTHER INFORMATION: Flexible linker

<400> SEQUENCE: 41

Thr Pro Ser His Leu Ser His Ile Leu Pro Ser Phe Gly Leu Pro Thr
1               5                   10                  15

Phe Asn

<210> SEQ ID NO 42
<211> LENGTH: 18
<212> TYPE: PRT
<213> ORGANISM: Artificial Sequence
<220> FEATURE:
<223> OTHER INFORMATION: Flexible linker

<400> SEQUENCE: 42
```

```
Arg Pro Val Ser Pro Phe Thr Phe Pro Arg Leu Ser Asn Ser Trp Leu
1               5                   10                  15

Pro Ala

<210> SEQ ID NO 43
<211> LENGTH: 18
<212> TYPE: PRT
<213> ORGANISM: Artificial Sequence
<220> FEATURE:
<223> OTHER INFORMATION: Flexible linker

<400> SEQUENCE: 43

Ser Pro Ala Ala His Phe Pro Arg Ser Ile Pro Arg Pro Gly Pro Ile
1               5                   10                  15

Arg Thr

<210> SEQ ID NO 44
<211> LENGTH: 18
<212> TYPE: PRT
<213> ORGANISM: Artificial Sequence
<220> FEATURE:
<223> OTHER INFORMATION: Flexible linker

<400> SEQUENCE: 44

Ala Pro Gly Pro Ser Ala Pro Ser His Arg Ser Leu Pro Ser Arg Ala
1               5                   10                  15

Phe Gly

<210> SEQ ID NO 45
<211> LENGTH: 18
<212> TYPE: PRT
<213> ORGANISM: Artificial Sequence
<220> FEATURE:
<223> OTHER INFORMATION: Flexible linker

<400> SEQUENCE: 45

Pro Arg Asn Ser Ile His Phe Leu His Pro Leu Leu Val Ala Pro Leu
1               5                   10                  15

Gly Ala

<210> SEQ ID NO 46
<211> LENGTH: 18
<212> TYPE: PRT
<213> ORGANISM: Artificial Sequence
<220> FEATURE:
<223> OTHER INFORMATION: Flexible linker

<400> SEQUENCE: 46

Met Pro Ser Leu Ser Gly Val Leu Gln Val Arg Tyr Leu Ser Pro Pro
1               5                   10                  15

Asp Leu

<210> SEQ ID NO 47
<211> LENGTH: 18
<212> TYPE: PRT
<213> ORGANISM: Artificial Sequence
<220> FEATURE:
<223> OTHER INFORMATION: Flexible linker

<400> SEQUENCE: 47

Ser Pro Gln Tyr Pro Ser Pro Leu Thr Leu Thr Leu Pro Pro His Pro
1               5                   10                  15
```

Ser Leu

<210> SEQ ID NO 48
<211> LENGTH: 18
<212> TYPE: PRT
<213> ORGANISM: Artificial Sequence
<220> FEATURE:
<223> OTHER INFORMATION: Flexible linker

<400> SEQUENCE: 48

Asn Pro Ser Leu Asn Pro Pro Ser Tyr Leu His Arg Ala Pro Ser Arg
1               5                   10                  15

Ile Ser

<210> SEQ ID NO 49
<211> LENGTH: 17
<212> TYPE: PRT
<213> ORGANISM: Artificial Sequence
<220> FEATURE:
<223> OTHER INFORMATION: Flexible linker

<400> SEQUENCE: 49

Leu Pro Trp Arg Thr Ser Leu Leu Pro Ser Leu Pro Leu Arg Arg Arg
1               5                   10                  15

Pro

<210> SEQ ID NO 50
<211> LENGTH: 18
<212> TYPE: PRT
<213> ORGANISM: Artificial Sequence
<220> FEATURE:
<223> OTHER INFORMATION: Flexible linker

<400> SEQUENCE: 50

Pro Pro Leu Phe Ala Lys Gly Pro Val Gly Leu Leu Ser Arg Ser Phe
1               5                   10                  15

Pro Pro

<210> SEQ ID NO 51
<211> LENGTH: 18
<212> TYPE: PRT
<213> ORGANISM: Artificial Sequence
<220> FEATURE:
<223> OTHER INFORMATION: Flexible linker

<400> SEQUENCE: 51

Val Pro Pro Ala Pro Val Val Ser Leu Arg Ser Ala His Ala Arg Pro
1               5                   10                  15

Pro Tyr

<210> SEQ ID NO 52
<211> LENGTH: 17
<212> TYPE: PRT
<213> ORGANISM: Artificial Sequence
<220> FEATURE:
<223> OTHER INFORMATION: Flexible linker

<400> SEQUENCE: 52

Leu Arg Pro Thr Pro Pro Arg Val Arg Ser Tyr Thr Cys Cys Pro Thr
1               5                   10                  15

Pro

<210> SEQ ID NO 53

```
<211> LENGTH: 18
<212> TYPE: PRT
<213> ORGANISM: Artificial Sequence
<220> FEATURE:
<223> OTHER INFORMATION: Flexible linker

<400> SEQUENCE: 53

Pro Asn Val Ala His Val Leu Pro Leu Leu Thr Val Pro Trp Asp Asn
1               5                   10                  15

Leu Arg

<210> SEQ ID NO 54
<211> LENGTH: 18
<212> TYPE: PRT
<213> ORGANISM: Artificial Sequence
<220> FEATURE:
<223> OTHER INFORMATION: Flexible linker

<400> SEQUENCE: 54

Cys Asn Pro Leu Leu Pro Leu Cys Ala Arg Ser Pro Ala Val Arg Thr
1               5                   10                  15

Phe Pro

<210> SEQ ID NO 55
<211> LENGTH: 11
<212> TYPE: PRT
<213> ORGANISM: Artificial Sequence
<220> FEATURE:
<223> OTHER INFORMATION: Linker

<400> SEQUENCE: 55

Asp Leu Cys Leu Arg Asp Trp Gly Cys Leu Trp
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Linker

<400> SEQUENCE: 56

Asp Ile Cys Leu Pro Arg Trp Gly Cys Leu Trp
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Linker

<400> SEQUENCE: 57

Met Glu Asp Ile Cys Leu Pro Arg Trp Gly Cys Leu Trp Gly Asp
1               5                   10                  15

<210> SEQ ID NO 58
<211> LENGTH: 20
<212> TYPE: PRT
<213> ORGANISM: Artificial Sequence
<220> FEATURE:
<223> OTHER INFORMATION: Linker

<400> SEQUENCE: 58

Gln Arg Leu Met Glu Asp Ile Cys Leu Pro Arg Trp Gly Cys Leu Trp
1               5                   10                  15
```

Glu Asp Asp Glu
            20

<210> SEQ ID NO 59
<211> LENGTH: 20
<212> TYPE: PRT
<213> ORGANISM: Artificial Sequence
<220> FEATURE:
<223> OTHER INFORMATION: Linker

<400> SEQUENCE: 59

Gln Gly Leu Ile Gly Asp Ile Cys Leu Pro Arg Trp Gly Cys Leu Trp
1               5                   10                  15

Gly Arg Ser Val
            20

<210> SEQ ID NO 60
<211> LENGTH: 21
<212> TYPE: PRT
<213> ORGANISM: Artificial Sequence
<220> FEATURE:
<223> OTHER INFORMATION: Linker

<400> SEQUENCE: 60

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 61
<211> LENGTH: 15
<212> TYPE: PRT
<213> ORGANISM: Artificial Sequence
<220> FEATURE:
<223> OTHER INFORMATION: Linker

<400> SEQUENCE: 61

Glu Asp Ile Cys Leu Pro Arg Trp Gly Cys Leu Trp Glu Asp Asp
1               5                   10                  15

<210> SEQ ID NO 62
<211> LENGTH: 18
<212> TYPE: PRT
<213> ORGANISM: Artificial Sequence
<220> FEATURE:
<223> OTHER INFORMATION: Linker

<400> SEQUENCE: 62

Arg Leu Met Glu Asp Ile Cys Leu Pro Arg Trp Gly Cys Leu Trp Glu
1               5                   10                  15

Asp Asp

<210> SEQ ID NO 63
<211> LENGTH: 16
<212> TYPE: PRT
<213> ORGANISM: Artificial Sequence
<220> FEATURE:
<223> OTHER INFORMATION: Linker

<400> SEQUENCE: 63

Met Glu Asp Ile Cys Leu Pro Arg Trp Gly Cys Leu Trp Glu Asp Asp
1               5                   10                  15

<210> SEQ ID NO 64

```
<211> LENGTH: 15
<212> TYPE: PRT
<213> ORGANISM: Artificial Sequence
<220> FEATURE:
<223> OTHER INFORMATION: Linker

<400> SEQUENCE: 64

Met Glu Asp Ile Cys Leu Pro Arg Trp Gly Cys Leu Trp Glu Asp
1               5                   10                  15

<210> SEQ ID NO 65
<211> LENGTH: 18
<212> TYPE: PRT
<213> ORGANISM: Artificial Sequence
<220> FEATURE:
<223> OTHER INFORMATION: Linker

<400> SEQUENCE: 65

Arg Leu Met Glu Asp Ile Cys Leu Ala Arg Trp Gly Cys Leu Trp Glu
1               5                   10                  15

Asp Asp

<210> SEQ ID NO 66
<211> LENGTH: 20
<212> TYPE: PRT
<213> ORGANISM: Artificial Sequence
<220> FEATURE:
<223> OTHER INFORMATION: Linker

<400> SEQUENCE: 66

Glu Val Arg Ser Phe Cys Thr Arg Trp Pro Ala Glu Lys Ser Cys Lys
1               5                   10                  15

Pro Leu Arg Gly
            20

<210> SEQ ID NO 67
<211> LENGTH: 20
<212> TYPE: PRT
<213> ORGANISM: Artificial Sequence
<220> FEATURE:
<223> OTHER INFORMATION: Linker

<400> SEQUENCE: 67

Arg Ala Pro Glu Ser Phe Val Cys Tyr Trp Glu Thr Ile Cys Phe Glu
1               5                   10                  15

Arg Ser Glu Gln
            20

<210> SEQ ID NO 68
<211> LENGTH: 11
<212> TYPE: PRT
<213> ORGANISM: Artificial Sequence
<220> FEATURE:
<223> OTHER INFORMATION: Linker

<400> SEQUENCE: 68

Glu Met Cys Tyr Phe Pro Gly Ile Cys Trp Met
1               5                   10

<210> SEQ ID NO 69
<211> LENGTH: 11
<212> TYPE: PRT
<213> ORGANISM: Artificial Sequence
<220> FEATURE:
<223> OTHER INFORMATION: peptide sequence
```

```
<400> SEQUENCE: 69

Gly Ala Pro Ala Pro Ala Ala Pro Ala Pro Ala
1               5                   10

<210> SEQ ID NO 70
<211> LENGTH: 4
<212> TYPE: PRT
<213> ORGANISM: Artificial Sequence
<220> FEATURE:
<223> OTHER INFORMATION: peptide sequence

<400> SEQUENCE: 70

Pro Pro Pro Pro
1

<210> SEQ ID NO 71
<211> LENGTH: 6
<212> TYPE: PRT
<213> ORGANISM: Artificial sequence
<220> FEATURE:
<223> OTHER INFORMATION: Linker

<400> SEQUENCE: 71

Ala Ser Gly Gly Gly Gly
1               5

<210> SEQ ID NO 72
<211> LENGTH: 8
<212> TYPE: PRT
<213> ORGANISM: Artificial Sequence
<220> FEATURE:
<223> OTHER INFORMATION: Linker

<400> SEQUENCE: 72

Ala Ser Gly Gly Gly Gly Ser Gly
1               5

<210> SEQ ID NO 73
<211> LENGTH: 5
<212> TYPE: PRT
<213> ORGANISM: Artificial Sequence
<220> FEATURE:
<223> OTHER INFORMATION: Linker

<400> SEQUENCE: 73

Ala Ser Gly Gly Gly
1               5

<210> SEQ ID NO 74
<211> LENGTH: 7
<212> TYPE: PRT
<213> ORGANISM: Artificial Sequence
<220> FEATURE:
<223> OTHER INFORMATION: Linker

<400> SEQUENCE: 74

Ala Ala Ala Ser Gly Gly Gly
1               5

<210> SEQ ID NO 75
<211> LENGTH: 20
<212> TYPE: PRT
<213> ORGANISM: Artificial Sequence
<220> FEATURE:
<223> OTHER INFORMATION: Linker

<400> SEQUENCE: 75
```

-continued

Ser Gly Gly Gly Gly Ser Gly Gly Gly Ser Gly Gly Gly Ser
1               5                   10                  15

Gly Gly Gly Ser
        20

<210> SEQ ID NO 76
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 76

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Lys Lys
            20                  25                  30

Leu Val Gly Glu Arg His His His His His His
        35                  40

<210> SEQ ID NO 77
<211> LENGTH: 43
<212> TYPE: PRT
<213> ORGANISM: artificial sequence
<220> FEATURE:
<223> OTHER INFORMATION: GCN4 peptide variant

<400> SEQUENCE: 77

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Lys Ala
            20                  25                  30

Leu Val Gly Glu Arg His His His His His His
        35                  40

<210> SEQ ID NO 78
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 78

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Ala Lys
            20                  25                  30

Leu Val Gly Glu Arg His His His His His His
        35                  40

<210> SEQ ID NO 79
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 79

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Gln Lys
            20                  25                  30

Leu Val Gly Glu Arg His His His His His
        35                  40

<210> SEQ ID NO 80
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 80

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Asn Lys
            20                  25                  30

Leu Val Gly Glu Arg His His His His His His
        35                  40

<210> SEQ ID NO 81
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 81

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Ala Ala
            20                  25                  30

Leu Val Gly Glu Arg His His His His His His
        35                  40

<210> SEQ ID NO 82
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 82

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Gln Ala
            20                  25                  30

Leu Val Gly Glu Arg His His His His His His
        35                  40

<210> SEQ ID NO 83
<211> LENGTH: 43
<212> TYPE: PRT
<213> ORGANISM: Artificial Sequence
<220> FEATURE:
<223> OTHER INFORMATION: GCN4 peptide variant

<400> SEQUENCE: 83

Gly Gly Gly Gly Ser Gly Gly Gly Ser Gly Gly Gly Gly Ser Gly
1               5                   10                  15

Gly Gly Gly Ser Tyr His Leu Glu Asn Glu Val Ala Arg Leu Asn Ala
            20                  25                  30

Leu Val Gly Glu Arg His His His His His His
        35                  40

```
<210> SEQ ID NO 84
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 84

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Lys Leu Val Gly Glu Arg His His His His His His
            35                  40

<210> SEQ ID NO 85
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 85

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Ala Leu Val Gly Glu Arg His His His His His His
            35                  40

<210> SEQ ID NO 86
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 86

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Ala Leu Val Gly Glu Arg His His His His His His
            35                  40

<210> SEQ ID NO 87
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 87

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Lys Leu Val Gly Glu Arg His His His His His His
            35                  40

<210> SEQ ID NO 88
```

<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 88

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Lys Leu Val Gly Glu Arg His His His His His His
        35                  40

<210> SEQ ID NO 89
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 89

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Lys Leu Val Gly Glu Arg His His His His His His
        35                  40

<210> SEQ ID NO 90
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 90

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Lys Leu Val Gly Glu Arg His His His His His His
        35                  40

<210> SEQ ID NO 91
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 91

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Lys Leu Val Gly Glu Arg His His His His His His
        35                  40

<210> SEQ ID NO 92
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 92

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Lys Leu Val Gly Glu Arg His His His His His His
        35                  40

<210> SEQ ID NO 93
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 93

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Ala Leu Val Gly Glu Arg His His His His His His
        35                  40

<210> SEQ ID NO 94
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 94

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Ala Leu Val Gly Glu Arg His His His His His His
        35                  40

<210> SEQ ID NO 95
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 95

Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Ala Leu Val Gly Glu Arg His His His His His His
        35                  40

<210> SEQ ID NO 96
<211> LENGTH: 44
<212> TYPE: PRT
<213> ORGANISM: Artificial Sequence
<220> FEATURE:
<223> OTHER INFORMATION: GCN4 peptide variant

```
<400> SEQUENCE: 96

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Ala
            20                  25                  30

Ala Leu Val Gly Glu Arg His His His His His His
        35                  40

<210> SEQ ID NO 97
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 97

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Gln
            20                  25                  30

Ala Leu Val Gly Glu Arg His His His His His His
        35                  40

<210> SEQ ID NO 98
<211> LENGTH: 44
<212> TYPE: PRT
<213> ORGANISM: Artificial Sequence
<220> FEATURE:
<223> OTHER INFORMATION: GCN4 peptide variant

<400> SEQUENCE: 98

Ala Ser Gly Gly Gly Ala Met Lys Gln Leu Glu Pro Lys Val Glu Glu
1               5                   10                  15

Leu Leu Pro Lys Asn Tyr His Leu Glu Asn Glu Val Ala Arg Leu Asn
            20                  25                  30

Ala Leu Val Gly Glu Arg His His His His His His
        35                  40

<210> SEQ ID NO 99
<211> LENGTH: 243
<212> TYPE: PRT
<213> ORGANISM: Artificial Sequence
<220> FEATURE:
<223> OTHER INFORMATION: 52SR4 scFV variant

<400> SEQUENCE: 99

Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110
```

Gly Gly Ser Gly Gly Gly Ser Gly Gly Gly Ser Gly Gly
            115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser

<210> SEQ ID NO 100
<211> LENGTH: 292
<212> TYPE: PRT
<213> ORGANISM: Artificial Sequence
<220> FEATURE:
<223> OTHER INFORMATION: 52SR4 scFv variant

<400> SEQUENCE: 100

Asp Val Gln Leu Gln Gln Ser Gly Pro Gly Leu Val Ala Pro Ser Gln
1               5                   10                  15

Ser Leu Ser Ile Thr Cys Thr Val Ser Gly Phe Leu Leu Thr Asp Tyr
            20                  25                  30

Gly Val Asn Trp Val Arg Gln Ser Pro Gly Lys Cys Leu Glu Trp Leu
        35                  40                  45

Gly Val Ile Trp Gly Asp Gly Ile Thr Asp Tyr Asn Ser Ala Leu Lys
    50                  55                  60

Ser Arg Leu Ser Val Thr Lys Asp Asn Ser Lys Ser Gln Val Phe Leu
65                  70                  75                  80

Lys Met Asn Ser Leu Gln Ser Gly Asp Ser Ala Arg Tyr Tyr Cys Val
                85                  90                  95

Thr Gly Leu Phe Asp Tyr Trp Gly Gln Gly Thr Thr Leu Thr Val Ser
            100                 105                 110

Ser Pro Ala Arg Phe Ser Gly Ser Leu Ile Gly Asp Lys Ala Ala Leu
        115                 120                 125

Thr Ile Thr Gly Ala Gln Thr Glu Asp Glu Ala Ile Tyr Phe Cys Val
    130                 135                 140

Leu Trp Tyr Ser Asp His Trp Val Phe Gly Cys Gly Thr Lys Leu Thr
145                 150                 155                 160

Val Leu Gly Gly Gly Gly Ser Gly Gly Gly Ser Gly Gly
                165                 170                 175

Gly Ser Gly Gly Gly Ser Asp Ala Val Val Thr Gln Glu Ser Ala
            180                 185                 190

Leu Thr Ser Ser Pro Gly Glu Thr Val Thr Leu Thr Cys Arg Ser Ser
        195                 200                 205

Thr Gly Ala Val Thr Thr Ser Asn Tyr Ala Ser Trp Val Gln Glu Lys
    210                 215                 220

-continued

Pro Asp His Leu Phe Thr Gly Leu Ile Gly Gly Thr Asn Asn Arg Ala
225                 230                 235                 240

Pro Gly Val Pro Ala Arg Phe Ser Gly Ser Leu Ile Gly Asp Lys Ala
            245                 250                 255

Ala Leu Thr Ile Thr Gly Ala Gln Thr Glu Asp Glu Ala Ile Tyr Phe
        260                 265                 270

Cys Val Leu Trp Tyr Ser Asp His Trp Val Phe Gly Cys Gly Thr Lys
    275                 280                 285

Leu Thr Val Leu
    290

<210> SEQ ID NO 101
<211> LENGTH: 20
<212> TYPE: PRT
<213> ORGANISM: Artificial Sequence
<220> FEATURE:
<223> OTHER INFORMATION: signal sequence

<400> SEQUENCE: 101

Met Ser Val Pro Thr Gln Val Leu Gly Leu Leu Leu Leu Trp Leu Thr
1               5                   10                  15

Asp Ala Arg Cys
            20

<210> SEQ ID NO 102
<211> LENGTH: 19
<212> TYPE: PRT
<213> ORGANISM: Artificial Sequence
<220> FEATURE:
<223> OTHER INFORMATION: signal sequence

<400> SEQUENCE: 102

Met Glu Trp Ser Trp Val Phe Leu Phe Phe Leu Ser Val Thr Thr Gly
1               5                   10                  15

Val His Ser

<210> SEQ ID NO 103
<211> LENGTH: 19
<212> TYPE: PRT
<213> ORGANISM: Artificial Sequence
<220> FEATURE:
<223> OTHER INFORMATION: signal sequence

<400> SEQUENCE: 103

Met Asp Trp Leu Trp Thr Leu Leu Phe Leu Met Ala Ala Ala Gln Ser
1               5                   10                  15

Ala Gln Ala

<210> SEQ ID NO 104
<211> LENGTH: 19
<212> TYPE: PRT
<213> ORGANISM: Artificial Sequence
<220> FEATURE:
<223> OTHER INFORMATION: signal sequence

<400> SEQUENCE: 104

Met Gly Trp Ser Trp Thr Phe Leu Phe Leu Leu Ser Gly Thr Ser Gly
1               5                   10                  15

Val Leu Ser

<210> SEQ ID NO 105
<211> LENGTH: 307

```
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 105

Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Thr Ser Asp Lys Thr His Thr Cys Pro Pro Cys Pro Lys
                245                 250                 255

Gly Lys His Leu Cys Pro Ser Pro Leu Phe Pro Gly Pro Ser Lys Pro
            260                 265                 270

Leu Asp Pro Lys Phe Trp Val Leu Val Val Val Gly Val Leu Ala
        275                 280                 285

Cys Tyr Ser Leu Leu Val Thr Val Ala Phe Ile Ile Phe Trp Val Thr
    290                 295                 300

Arg Gly Ser
305

<210> SEQ ID NO 106
<211> LENGTH: 507
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 106
```

-continued

```
Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Thr Ser Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
```

```
                420             425             430
Ser Lys Leu Thr Val Asp Lys Ser Arg Trp Gln Gln Gly Asn Val Phe
                435             440             445

Ser Cys Ser Val Met His Glu Ala Leu His Asn His Tyr Thr Gln Lys
                450             455             460

Ser Leu Ser Leu Ser Pro Gly Lys Leu Asp Pro Lys Phe Trp Val Leu
465             470             475             480

Val Val Val Gly Gly Val Leu Ala Cys Tyr Ser Leu Leu Val Thr Val
                485             490             495

Ala Phe Ile Ile Phe Trp Val Thr Arg Gly Ser
                500             505

<210> SEQ ID NO 107
<211> LENGTH: 356
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 107

Asp Val Gln Leu Gln Gln Ser Gly Pro Gly Leu Val Ala Pro Ser Gln
1               5                   10                  15

Ser Leu Ser Ile Thr Cys Thr Val Ser Gly Phe Leu Leu Thr Asp Tyr
                20                  25                  30

Gly Val Asn Trp Val Arg Gln Ser Pro Gly Lys Cys Leu Glu Trp Leu
                35                  40                  45

Gly Val Ile Trp Gly Asp Gly Ile Thr Asp Tyr Asn Ser Ala Leu Lys
            50                  55                  60

Ser Arg Leu Ser Val Thr Lys Asp Asn Ser Lys Ser Gln Val Phe Leu
65              70                  75                  80

Lys Met Asn Ser Leu Gln Ser Gly Asp Ser Ala Arg Tyr Tyr Cys Val
                85                  90                  95

Thr Gly Leu Phe Asp Tyr Trp Gly Gln Gly Thr Thr Leu Thr Val Ser
                100                 105                 110

Ser Pro Ala Arg Phe Ser Gly Ser Leu Ile Gly Asp Lys Ala Ala Leu
                115                 120                 125

Thr Ile Thr Gly Ala Gln Thr Glu Asp Glu Ala Ile Tyr Phe Cys Val
            130                 135                 140

Leu Trp Tyr Ser Asp His Trp Val Phe Gly Cys Gly Thr Lys Leu Thr
145             150                 155                 160

Val Leu Gly Gly Gly Gly Ser Gly Gly Gly Ser Gly Gly Gly
                165                 170                 175

Gly Ser Gly Gly Gly Ser Asp Ala Val Val Thr Gln Glu Ser Ala
                180                 185                 190

Leu Thr Ser Ser Pro Gly Glu Thr Val Thr Leu Thr Cys Arg Ser Ser
                195                 200                 205

Thr Gly Ala Val Thr Thr Ser Asn Tyr Ala Ser Trp Val Gln Glu Lys
            210                 215                 220

Pro Asp His Leu Phe Thr Gly Leu Ile Gly Gly Thr Asn Asn Arg Ala
225             230                 235                 240

Pro Gly Val Pro Ala Arg Phe Ser Gly Ser Leu Ile Gly Asp Lys Ala
                245                 250                 255

Ala Leu Thr Ile Thr Gly Ala Gln Thr Glu Asp Glu Ala Ile Tyr Phe
                260                 265                 270
```

```
Cys Val Leu Trp Tyr Ser Asp His Trp Val Phe Gly Cys Gly Thr Lys
            275                 280                 285

Leu Thr Val Leu Thr Ser Asp Lys Thr His Thr Cys Pro Pro Cys Pro
    290                 295                 300

Lys Gly Lys His Leu Cys Pro Ser Pro Leu Phe Pro Gly Pro Ser Lys
305                 310                 315                 320

Pro Leu Asp Pro Lys Phe Trp Val Leu Val Val Val Gly Gly Val Leu
                325                 330                 335

Ala Cys Tyr Ser Leu Leu Val Thr Val Ala Phe Ile Ile Phe Trp Val
            340                 345                 350

Thr Arg Gly Ser
            355

<210> SEQ ID NO 108
<211> LENGTH: 556
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 108

Asp Val Gln Leu Gln Gln Ser Gly Pro Gly Leu Val Ala Pro Ser Gln
1               5                   10                  15

Ser Leu Ser Ile Thr Cys Thr Val Ser Gly Phe Leu Leu Thr Asp Tyr
            20                  25                  30

Gly Val Asn Trp Val Arg Gln Ser Pro Gly Lys Cys Leu Glu Trp Leu
        35                  40                  45

Gly Val Ile Trp Gly Asp Gly Ile Thr Asp Tyr Asn Ser Ala Leu Lys
    50                  55                  60

Ser Arg Leu Ser Val Thr Lys Asp Asn Ser Lys Ser Gln Val Phe Leu
65                  70                  75                  80

Lys Met Asn Ser Leu Gln Ser Gly Asp Ser Ala Arg Tyr Tyr Cys Val
                85                  90                  95

Thr Gly Leu Phe Asp Tyr Trp Gly Gln Gly Thr Thr Leu Thr Val Ser
            100                 105                 110

Ser Pro Ala Arg Phe Ser Gly Ser Leu Ile Gly Asp Lys Ala Ala Leu
        115                 120                 125

Thr Ile Thr Gly Ala Gln Thr Glu Asp Glu Ala Ile Tyr Phe Cys Val
    130                 135                 140

Leu Trp Tyr Ser Asp His Trp Val Phe Gly Cys Gly Thr Lys Leu Thr
145                 150                 155                 160

Val Leu Gly Gly Gly Gly Ser Gly Gly Gly Ser Gly Gly Gly Gly Gly
                165                 170                 175

Gly Ser Gly Gly Gly Gly Ser Asp Ala Val Val Thr Gln Glu Ser Ala
            180                 185                 190

Leu Thr Ser Ser Pro Gly Glu Thr Val Thr Leu Thr Cys Arg Ser Ser
        195                 200                 205

Thr Gly Ala Val Thr Thr Ser Asn Tyr Ala Ser Trp Val Gln Glu Lys
    210                 215                 220

Pro Asp His Leu Phe Thr Gly Leu Ile Gly Gly Thr Asn Asn Arg Ala
225                 230                 235                 240

Pro Gly Val Pro Ala Arg Phe Ser Gly Ser Leu Ile Gly Asp Lys Ala
                245                 250                 255

Ala Leu Thr Ile Thr Gly Ala Gln Thr Glu Asp Glu Ala Ile Tyr Phe
            260                 265                 270
```

Cys Val Leu Trp Tyr Ser Asp His Trp Val Phe Gly Cys Gly Thr Lys
            275                 280                 285
Leu Thr Val Leu Thr Ser Asp Lys Thr His Thr Cys Pro Pro Cys Pro
        290                 295                 300
Ala Pro Glu Leu Gly Gly Pro Ser Val Phe Leu Phe Pro Pro Lys
305                 310                 315                 320
Pro Lys Asp Thr Leu Met Ile Ser Arg Thr Pro Glu Val Thr Cys Val
                325                 330                 335
Val Val Asp Val Ser His Glu Asp Pro Glu Val Lys Phe Asn Trp Tyr
            340                 345                 350
Val Asp Gly Val Glu Val His Asn Ala Lys Thr Lys Pro Arg Glu Glu
        355                 360                 365
Gln Tyr Asn Ser Thr Tyr Arg Val Val Ser Val Leu Thr Val Leu His
    370                 375                 380
Gln Asp Trp Leu Asn Gly Lys Glu Tyr Lys Cys Lys Val Ser Asn Lys
385                 390                 395                 400
Ala Leu Pro Ala Pro Ile Glu Lys Thr Ile Ser Lys Ala Lys Gly Gln
                405                 410                 415
Pro Arg Glu Pro Gln Val Tyr Thr Leu Pro Pro Ser Arg Asp Glu Leu
            420                 425                 430
Thr Lys Asn Gln Val Ser Leu Thr Cys Leu Val Lys Gly Phe Tyr Pro
        435                 440                 445
Ser Asp Ile Ala Val Glu Trp Glu Ser Asn Gly Gln Pro Glu Asn Asn
    450                 455                 460
Tyr Lys Thr Thr Pro Pro Val Leu Asp Ser Asp Gly Ser Phe Phe Leu
465                 470                 475                 480
Tyr Ser Lys Leu Thr Val Asp Lys Ser Arg Trp Gln Gln Gly Asn Val
                485                 490                 495
Phe Ser Cys Ser Val Met His Glu Ala Leu His Asn His Tyr Thr Gln
            500                 505                 510
Lys Ser Leu Ser Leu Ser Pro Gly Lys Leu Asp Pro Lys Phe Trp Val
        515                 520                 525
Leu Val Val Val Gly Gly Val Leu Ala Cys Tyr Ser Leu Leu Val Thr
    530                 535                 540
Val Ala Phe Ile Ile Phe Trp Val Thr Arg Gly Ser
545                 550                 555

<210> SEQ ID NO 109
<211> LENGTH: 460
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 109

Asp Ala Val Val Thr Gln Glu Ser Ala Leu Thr Ser Ser Pro Gly Glu
1               5                   10                  15
Thr Val Thr Leu Thr Cys Arg Ser Ser Thr Gly Ala Val Thr Thr Ser
            20                  25                  30
Asn Tyr Ala Ser Trp Val Gln Glu Lys Pro Asp His Leu Phe Thr Gly
        35                  40                  45
Leu Ile Gly Gly Thr Asn Asn Arg Ala Pro Gly Val Pro Ala Arg Phe
    50                  55                  60
Ser Gly Ser Leu Ile Gly Asp Lys Ala Ala Leu Thr Ile Thr Gly Ala

```
                 65                  70                  75                  80
Gln Thr Glu Asp Glu Ala Ile Tyr Phe Cys Val Leu Trp Tyr Ser Asp
                 85                  90                  95
His Trp Val Phe Gly Cys Gly Thr Lys Leu Thr Val Leu Gly Gly Gly
                100                 105                 110
Gly Gly Ser Gly Gly Gly Gly Ser Gly Gly Gly Gly Ser Gly Gly Gly
                115                 120                 125
Gly Ser Asp Val Gln Leu Gln Gln Ser Gly Pro Gly Leu Val Ala Pro
            130                 135                 140
Ser Gln Ser Leu Ser Ile Thr Cys Thr Val Ser Gly Phe Leu Leu Thr
145                 150                 155                 160
Asp Tyr Gly Val Asn Trp Val Arg Gln Ser Pro Gly Lys Cys Leu Glu
                165                 170                 175
Trp Leu Gly Val Ile Trp Gly Asp Gly Ile Thr Asp Tyr Asn Ser Ala
                180                 185                 190
Leu Lys Ser Arg Leu Ser Val Thr Lys Asp Asn Ser Lys Ser Gln Val
                195                 200                 205
Phe Leu Lys Met Asn Ser Leu Gln Ser Gly Asp Ser Ala Arg Tyr Tyr
            210                 215                 220
Cys Val Thr Gly Leu Phe Asp Tyr Trp Gly Gln Gly Thr Thr Leu Thr
225                 230                 235                 240
Val Ser Ser Thr Ser Asp Lys Thr His Thr Cys Pro Pro Cys Pro Lys
                245                 250                 255
Gly Lys His Leu Cys Pro Ser Pro Leu Phe Pro Gly Pro Ser Lys Pro
                260                 265                 270
Leu Asp Pro Lys Phe Trp Val Leu Val Val Val Gly Val Leu Ala
            275                 280                 285
Cys Tyr Ser Leu Leu Val Thr Val Ala Phe Ile Ile Phe Trp Val Thr
            290                 295                 300
Arg Gly Ser Arg Ser Lys Arg Ser Arg Leu Leu His Ser Asp Tyr Met
305                 310                 315                 320
Asn Met Thr Pro Arg Arg Pro Gly Pro Thr Arg Lys His Tyr Gln Pro
                325                 330                 335
Tyr Ala Pro Pro Arg Asp Phe Ala Ala Tyr Arg Ser Arg Val Lys Phe
                340                 345                 350
Ser Arg Ser Ala Asp Ala Pro Ala Tyr Gln Gln Gly Gln Asn Gln Leu
            355                 360                 365
Tyr Asn Glu Leu Asn Leu Gly Arg Arg Glu Glu Tyr Asp Val Leu Asp
370                 375                 380
Lys Arg Arg Gly Arg Asp Pro Glu Met Gly Gly Lys Pro Arg Arg Lys
385                 390                 395                 400
Asn Pro Gln Glu Gly Leu Tyr Asn Glu Leu Gln Lys Asp Lys Met Ala
                405                 410                 415
Glu Ala Tyr Ser Glu Ile Gly Met Lys Gly Glu Arg Arg Arg Gly Lys
                420                 425                 430
Gly His Asp Gly Leu Tyr Gln Gly Leu Ser Thr Ala Thr Lys Asp Thr
            435                 440                 445
Tyr Asp Ala Leu His Met Gln Ala Leu Pro Pro Arg
450                 455                 460

<210> SEQ ID NO 110
<211> LENGTH: 660
<212> TYPE: PRT
<213> ORGANISM: Artificial Sequence
```

<220> FEATURE:
<223> OTHER INFORMATION: X-A fusion with transmembrane and intracellular
      regions

<400> SEQUENCE: 110

```
Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Thr Ser Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
```

```
385                 390                 395                 400
Asp Ile Ala Val Glu Trp Glu Ser Asn Gly Gln Pro Glu Asn Tyr
                405                 410                 415
Lys Thr Thr Pro Pro Val Leu Asp Ser Asp Gly Ser Phe Phe Leu Tyr
                420                 425                 430
Ser Lys Leu Thr Val Asp Lys Ser Arg Trp Gln Gln Gly Asn Val Phe
                435                 440                 445
Ser Cys Ser Val Met His Glu Ala Leu His Asn His Tyr Thr Gln Lys
                450                 455                 460
Ser Leu Ser Leu Ser Pro Gly Lys Leu Asp Pro Lys Phe Trp Val Leu
465                 470                 475                 480
Val Val Val Gly Gly Val Leu Ala Cys Tyr Ser Leu Leu Val Thr Val
                485                 490                 495
Ala Phe Ile Ile Phe Trp Val Thr Arg Gly Ser Arg Ser Lys Arg Ser
                500                 505                 510
Arg Leu Leu His Ser Asp Tyr Met Asn Met Thr Pro Arg Arg Pro Gly
                515                 520                 525
Pro Thr Arg Lys His Tyr Gln Pro Tyr Ala Pro Pro Arg Asp Phe Ala
                530                 535                 540
Ala Tyr Arg Ser Arg Val Lys Phe Ser Arg Ser Ala Asp Ala Pro Ala
545                 550                 555                 560
Tyr Gln Gln Gly Gln Asn Gln Leu Tyr Asn Glu Leu Asn Leu Gly Arg
                565                 570                 575
Arg Glu Glu Tyr Asp Val Leu Asp Lys Arg Gly Arg Asp Pro Glu
                580                 585                 590
Met Gly Gly Lys Pro Arg Arg Lys Asn Pro Gln Glu Gly Leu Tyr Asn
                595                 600                 605
Glu Leu Gln Lys Asp Lys Met Ala Glu Ala Tyr Ser Glu Ile Gly Met
                610                 615                 620
Lys Gly Glu Arg Arg Arg Gly Lys Gly His Asp Gly Leu Tyr Gln Gly
625                 630                 635                 640
Leu Ser Thr Ala Thr Lys Asp Thr Tyr Asp Ala Leu His Met Gln Ala
                645                 650                 655
Leu Pro Pro Arg
                660

<210> SEQ ID NO 111
<211> LENGTH: 509
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 111

Asp Val Gln Leu Gln Gln Ser Gly Pro Gly Leu Val Ala Pro Ser Gln
1                5                  10                  15
Ser Leu Ser Ile Thr Cys Thr Val Ser Gly Phe Leu Leu Thr Asp Tyr
                20                  25                  30
Gly Val Asn Trp Val Arg Gln Ser Pro Gly Lys Cys Leu Glu Trp Leu
                35                  40                  45
Gly Val Ile Trp Gly Asp Gly Ile Thr Asp Tyr Asn Ser Ala Leu Lys
                50                  55                  60
Ser Arg Leu Ser Val Thr Lys Asp Asn Ser Lys Ser Gln Val Phe Leu
65                  70                  75                  80
```

-continued

```
Lys Met Asn Ser Leu Gln Ser Gly Asp Ser Ala Arg Tyr Tyr Cys Val
                 85                  90                  95
Thr Gly Leu Phe Asp Tyr Trp Gly Gln Gly Thr Thr Leu Thr Val Ser
            100                 105                 110
Ser Pro Ala Arg Phe Ser Gly Ser Leu Ile Gly Asp Lys Ala Ala Leu
            115                 120                 125
Thr Ile Thr Gly Ala Gln Thr Glu Asp Glu Ala Ile Tyr Phe Cys Val
        130                 135                 140
Leu Trp Tyr Ser Asp His Trp Val Phe Gly Cys Gly Thr Lys Leu Thr
145                 150                 155                 160
Val Leu Gly Gly Gly Gly Ser Gly Gly Gly Ser Gly Gly Gly Gly
                165                 170                 175
Gly Ser Gly Gly Gly Ser Asp Ala Val Val Thr Gln Glu Ser Ala
            180                 185                 190
Leu Thr Ser Ser Pro Gly Glu Thr Val Thr Leu Thr Cys Arg Ser Ser
        195                 200                 205
Thr Gly Ala Val Thr Thr Ser Asn Tyr Ala Ser Trp Val Gln Glu Lys
        210                 215                 220
Pro Asp His Leu Phe Thr Gly Leu Ile Gly Gly Thr Asn Asn Arg Ala
225                 230                 235                 240
Pro Gly Val Pro Ala Arg Phe Ser Gly Ser Leu Ile Gly Asp Lys Ala
                245                 250                 255
Ala Leu Thr Ile Thr Gly Ala Gln Thr Glu Asp Glu Ala Ile Tyr Phe
            260                 265                 270
Cys Val Leu Trp Tyr Ser Asp His Trp Val Phe Gly Cys Gly Thr Lys
        275                 280                 285
Leu Thr Val Leu Thr Ser Asp Lys Thr His Thr Cys Pro Pro Cys Pro
290                 295                 300
Lys Gly Lys His Leu Cys Pro Ser Pro Leu Phe Pro Gly Pro Ser Lys
305                 310                 315                 320
Pro Leu Asp Pro Lys Phe Trp Val Leu Val Val Val Gly Gly Val Leu
                325                 330                 335
Ala Cys Tyr Ser Leu Leu Val Thr Val Ala Phe Ile Ile Phe Trp Val
            340                 345                 350
Thr Arg Gly Ser Arg Ser Lys Arg Ser Arg Leu Leu His Ser Asp Tyr
        355                 360                 365
Met Asn Met Thr Pro Arg Arg Pro Gly Pro Thr Arg Lys His Tyr Gln
        370                 375                 380
Pro Tyr Ala Pro Pro Arg Asp Phe Ala Ala Tyr Arg Ser Arg Val Lys
385                 390                 395                 400
Phe Ser Arg Ser Ala Asp Ala Pro Ala Tyr Gln Gln Gly Gln Asn Gln
                405                 410                 415
Leu Tyr Asn Glu Leu Asn Leu Gly Arg Arg Glu Glu Tyr Asp Val Leu
            420                 425                 430
Asp Lys Arg Arg Gly Arg Asp Pro Glu Met Gly Gly Lys Pro Arg Arg
        435                 440                 445
Lys Asn Pro Gln Glu Gly Leu Tyr Asn Glu Leu Gln Lys Asp Lys Met
        450                 455                 460
Ala Glu Ala Tyr Ser Glu Ile Gly Met Lys Gly Glu Arg Arg Arg Gly
465                 470                 475                 480
Lys Gly His Asp Gly Leu Tyr Gln Gly Leu Ser Thr Ala Thr Lys Asp
                485                 490                 495
Thr Tyr Asp Ala Leu His Met Gln Ala Leu Pro Pro Arg
```

-continued

```
                500             505
```

<210> SEQ ID NO 112
<211> LENGTH: 709
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 112

```
Asp Val Gln Leu Gln Gln Ser Gly Pro Gly Leu Val Ala Pro Ser Gln
1               5                   10                  15

Ser Leu Ser Ile Thr Cys Thr Val Ser Gly Phe Leu Leu Thr Asp Tyr
            20                  25                  30

Gly Val Asn Trp Val Arg Gln Ser Pro Gly Lys Cys Leu Glu Trp Leu
        35                  40                  45

Gly Val Ile Trp Gly Asp Gly Ile Thr Asp Tyr Asn Ser Ala Leu Lys
    50                  55                  60

Ser Arg Leu Ser Val Thr Lys Asp Asn Ser Lys Ser Gln Val Phe Leu
65                  70                  75                  80

Lys Met Asn Ser Leu Gln Ser Gly Asp Ser Ala Arg Tyr Tyr Cys Val
                85                  90                  95

Thr Gly Leu Phe Asp Tyr Trp Gly Gln Gly Thr Thr Leu Thr Val Ser
            100                 105                 110

Ser Pro Ala Arg Phe Ser Gly Ser Leu Ile Gly Asp Lys Ala Ala Leu
        115                 120                 125

Thr Ile Thr Gly Ala Gln Thr Glu Asp Glu Ala Ile Tyr Phe Cys Val
    130                 135                 140

Leu Trp Tyr Ser Asp His Trp Val Phe Gly Cys Gly Thr Lys Leu Thr
145                 150                 155                 160

Val Leu Gly Gly Gly Gly Ser Gly Gly Gly Ser Gly Gly Gly
                165                 170                 175

Gly Ser Gly Gly Gly Ser Asp Ala Val Val Thr Gln Glu Ser Ala
            180                 185                 190

Leu Thr Ser Ser Pro Gly Glu Thr Val Thr Leu Thr Cys Arg Ser Ser
        195                 200                 205

Thr Gly Ala Val Thr Thr Ser Asn Tyr Ala Ser Trp Val Gln Glu Lys
    210                 215                 220

Pro Asp His Leu Phe Thr Gly Leu Ile Gly Gly Thr Asn Asn Arg Ala
225                 230                 235                 240

Pro Gly Val Pro Ala Arg Phe Ser Gly Ser Leu Ile Gly Asp Lys Ala
                245                 250                 255

Ala Leu Thr Ile Thr Gly Ala Gln Thr Glu Asp Glu Ala Ile Tyr Phe
            260                 265                 270

Cys Val Leu Trp Tyr Ser Asp His Trp Val Phe Gly Cys Gly Thr Lys
        275                 280                 285

Leu Thr Val Leu Thr Ser Asp Lys Thr His Thr Cys Pro Pro Cys Pro
    290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
            340                 345                 350
```

Val Asp Gly Val Glu Val His Asn Ala Lys Thr Lys Pro Arg Glu Glu
355                 360                 365

Gln Tyr Asn Ser Thr Tyr Arg Val Val Ser Val Leu Thr Val Leu His
370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
            405                 410                 415

Pro Arg Glu Pro Gln Val Tyr Thr Leu Pro Pro Ser Arg Asp Glu Leu
        420                 425                 430

Thr Lys Asn Gln Val Ser Leu Thr Cys Leu Val Lys Gly Phe Tyr Pro
    435                 440                 445

Ser Asp Ile Ala Val Glu Trp Glu Ser Asn Gly Gln Pro Glu Asn Asn
450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
            485                 490                 495

Phe Ser Cys Ser Val Met His Glu Ala Leu His Asn His Tyr Thr Gln
        500                 505                 510

Lys Ser Leu Ser Leu Ser Pro Gly Lys Leu Asp Pro Lys Phe Trp Val
    515                 520                 525

Leu Val Val Val Gly Gly Val Leu Ala Cys Tyr Ser Leu Leu Val Thr
530                 535                 540

Val Ala Phe Ile Ile Phe Trp Val Thr Arg Gly Ser Arg Ser Lys Arg
545                 550                 555                 560

Ser Arg Leu Leu His Ser Asp Tyr Met Asn Met Thr Pro Arg Arg Pro
            565                 570                 575

Gly Pro Thr Arg Lys His Tyr Gln Pro Tyr Ala Pro Pro Arg Asp Phe
        580                 585                 590

Ala Ala Tyr Arg Ser Arg Val Lys Phe Ser Arg Ser Ala Asp Ala Pro
    595                 600                 605

Ala Tyr Gln Gln Gly Gln Asn Gln Leu Tyr Asn Glu Leu Asn Leu Gly
610                 615                 620

Arg Arg Glu Glu Tyr Asp Val Leu Asp Lys Arg Arg Gly Arg Asp Pro
625                 630                 635                 640

Glu Met Gly Gly Lys Pro Arg Arg Lys Asn Pro Gln Glu Gly Leu Tyr
            645                 650                 655

Asn Glu Leu Gln Lys Asp Lys Met Ala Glu Ala Tyr Ser Glu Ile Gly
        660                 665                 670

Met Lys Gly Glu Arg Arg Arg Gly Lys Gly His Asp Gly Leu Tyr Gln
    675                 680                 685

Gly Leu Ser Thr Ala Thr Lys Asp Thr Tyr Asp Ala Leu His Met Gln
690                 695                 700

Ala Leu Pro Pro Arg
705

<210> SEQ ID NO 113
<211> LENGTH: 461
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 113

```
Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Gly Ser Gly Gly Gly Gly Ser Gly Gly Gly
            115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Thr Ser Asp Lys Thr His Thr Cys Pro Pro Cys Pro Lys
                245                 250                 255

Gly Lys His Leu Cys Pro Ser Pro Leu Phe Pro Gly Pro Ser Lys Pro
            260                 265                 270

Leu Asp Pro Lys Phe Trp Val Leu Val Val Val Gly Gly Val Leu Ala
        275                 280                 285

Cys Tyr Ser Leu Leu Val Thr Val Ala Phe Ile Ile Phe Trp Val Thr
    290                 295                 300

Arg Gly Ser Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415
```

```
Ala Glu Ala Tyr Ser Glu Ile Gly Met Lys Gly Glu Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 114
<211> LENGTH: 661
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 114

Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Ser Gly Gly Gly Ser Gly Gly Gly
            115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205

Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Thr Ser Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320
```

Tyr Asn Ser Thr Tyr Arg Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys Leu Asp Pro Lys Phe Trp Val Leu
465                 470                 475                 480

Val Val Val Gly Gly Val Leu Ala Cys Tyr Ser Leu Leu Val Thr Val
                485                 490                 495

Ala Phe Ile Ile Phe Trp Val Thr Arg Gly Ser Lys Arg Gly Arg Lys
            500                 505                 510

Lys Leu Leu Tyr Ile Phe Lys Gln Pro Phe Met Arg Pro Val Gln Thr
        515                 520                 525

Thr Gln Glu Glu Asp Gly Cys Ser Cys Arg Phe Pro Glu Glu Glu Glu
    530                 535                 540

Gly Gly Cys Glu Leu Arg Val Lys Phe Ser Arg Ser Ala Asp Ala Pro
545                 550                 555                 560

Ala Tyr Gln Gln Gly Gln Asn Gln Leu Tyr Asn Glu Leu Asn Leu Gly
                565                 570                 575

Arg Arg Glu Glu Tyr Asp Val Leu Asp Lys Arg Arg Gly Arg Asp Pro
            580                 585                 590

Glu Met Gly Gly Lys Pro Arg Arg Lys Asn Pro Gln Glu Gly Leu Tyr
        595                 600                 605

Asn Glu Leu Gln Lys Asp Lys Met Ala Glu Ala Tyr Ser Glu Ile Gly
    610                 615                 620

Met Lys Gly Glu Arg Arg Arg Gly Lys Gly His Asp Gly Leu Tyr Gln
625                 630                 635                 640

Gly Leu Ser Thr Ala Thr Lys Asp Thr Tyr Asp Ala Leu His Met Gln
                645                 650                 655

Ala Leu Pro Pro Arg
            660

<210> SEQ ID NO 115
<211> LENGTH: 510
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 115

Asp Val Gln Leu Gln Gln Ser Gly Pro Gly Leu Val Ala Pro Ser Gln

-continued

```
1               5                   10                  15
Ser Leu Ser Ile Thr Cys Thr Val Ser Gly Phe Leu Leu Thr Asp Tyr
                20                  25                  30

Gly Val Asn Trp Val Arg Gln Ser Pro Gly Lys Cys Leu Glu Trp Leu
                35                  40                  45

Gly Val Ile Trp Gly Asp Gly Ile Thr Asp Tyr Asn Ser Ala Leu Lys
                50                  55                  60

Ser Arg Leu Ser Val Thr Lys Asp Asn Ser Lys Ser Gln Val Phe Leu
65                  70                  75                  80

Lys Met Asn Ser Leu Gln Ser Gly Asp Ser Ala Arg Tyr Tyr Cys Val
                85                  90                  95

Thr Gly Leu Phe Asp Tyr Trp Gly Gln Gly Thr Leu Thr Val Ser
                100                 105                 110

Ser Pro Ala Arg Phe Ser Gly Ser Leu Ile Gly Asp Lys Ala Ala Leu
                115                 120                 125

Thr Ile Thr Gly Ala Gln Thr Glu Asp Glu Ala Ile Tyr Phe Cys Val
                130                 135                 140

Leu Trp Tyr Ser Asp His Trp Val Phe Gly Cys Gly Thr Lys Leu Thr
145                 150                 155                 160

Val Leu Gly Gly Gly Gly Ser Gly Gly Gly Ser Gly Gly Gly
                165                 170                 175

Gly Ser Gly Gly Gly Ser Asp Ala Val Val Thr Gln Glu Ser Ala
                180                 185                 190

Leu Thr Ser Ser Pro Gly Glu Thr Val Thr Leu Thr Cys Arg Ser Ser
                195                 200                 205

Thr Gly Ala Val Thr Thr Ser Asn Tyr Ala Ser Trp Val Gln Glu Lys
                210                 215                 220

Pro Asp His Leu Phe Thr Gly Leu Ile Gly Gly Thr Asn Asn Arg Ala
225                 230                 235                 240

Pro Gly Val Pro Ala Arg Phe Ser Gly Ser Leu Ile Gly Asp Lys Ala
                245                 250                 255

Ala Leu Thr Ile Thr Gly Ala Gln Thr Glu Asp Glu Ala Ile Tyr Phe
                260                 265                 270

Cys Val Leu Trp Tyr Ser Asp His Trp Val Phe Gly Cys Gly Thr Lys
                275                 280                 285

Leu Thr Val Leu Thr Ser Asp Lys Thr His Thr Cys Pro Pro Cys Pro
                290                 295                 300

Lys Gly Lys His Leu Cys Pro Ser Pro Leu Phe Pro Gly Pro Ser Lys
305                 310                 315                 320

Pro Leu Asp Pro Lys Phe Trp Val Leu Val Val Val Gly Gly Val Leu
                325                 330                 335

Ala Cys Tyr Ser Leu Leu Val Thr Val Ala Phe Ile Ile Phe Trp Val
                340                 345                 350

Thr Arg Gly Ser Lys Arg Gly Arg Lys Lys Leu Leu Tyr Ile Phe Lys
                355                 360                 365

Gln Pro Phe Met Arg Pro Val Gln Thr Thr Gln Glu Glu Asp Gly Cys
                370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430
```

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
        450                 455                 460

Met Ala Glu Ala Tyr Ser Glu Ile Gly Met Lys Gly Glu Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 116
<211> LENGTH: 710
<212> TYPE: PRT
<213> ORGANISM: Artificial Sequence
<220> FEATURE:
<223> OTHER INFORMATION: X-A fusion with transmembrane and intracellular
      regions

<400> SEQUENCE: 116

Asp Val Gln Leu Gln Gln Ser Gly Pro Gly Leu Val Ala Pro Ser Gln
1               5                   10                  15

Ser Leu Ser Ile Thr Cys Thr Val Ser Gly Phe Leu Leu Thr Asp Tyr
            20                  25                  30

Gly Val Asn Trp Val Arg Gln Ser Pro Gly Lys Cys Leu Glu Trp Leu
        35                  40                  45

Gly Val Ile Trp Gly Asp Gly Ile Thr Asp Tyr Asn Ser Ala Leu Lys
    50                  55                  60

Ser Arg Leu Ser Val Thr Lys Asp Asn Ser Lys Ser Gln Val Phe Leu
65                  70                  75                  80

Lys Met Asn Ser Leu Gln Ser Gly Asp Ser Ala Arg Tyr Tyr Cys Val
                85                  90                  95

Thr Gly Leu Phe Asp Tyr Trp Gly Gln Gly Thr Thr Leu Thr Val Ser
            100                 105                 110

Ser Pro Ala Arg Phe Ser Gly Ser Leu Ile Gly Asp Lys Ala Ala Leu
        115                 120                 125

Thr Ile Thr Gly Ala Gln Thr Glu Asp Glu Ala Ile Tyr Phe Cys Val
    130                 135                 140

Leu Trp Tyr Ser Asp His Trp Val Phe Gly Cys Gly Thr Lys Leu Thr
145                 150                 155                 160

Val Leu Gly Gly Gly Gly Ser Gly Gly Gly Ser Gly Gly Gly
                165                 170                 175

Gly Ser Gly Gly Gly Gly Ser Asp Ala Val Val Thr Gln Glu Ser Ala
            180                 185                 190

Leu Thr Ser Ser Pro Gly Glu Thr Val Thr Leu Thr Cys Arg Ser Ser
        195                 200                 205

Thr Gly Ala Val Thr Thr Ser Asn Tyr Ala Ser Trp Val Gln Glu Lys
    210                 215                 220

Pro Asp His Leu Phe Thr Gly Leu Ile Gly Gly Thr Asn Asn Arg Ala
225                 230                 235                 240

Pro Gly Val Pro Ala Arg Phe Ser Gly Ser Leu Ile Gly Asp Lys Ala
                245                 250                 255

Ala Leu Thr Ile Thr Gly Ala Gln Thr Glu Asp Glu Ala Ile Tyr Phe
            260                 265                 270

Cys Val Leu Trp Tyr Ser Asp His Trp Val Phe Gly Cys Gly Thr Lys

```
            275                 280                 285
Leu Thr Val Leu Thr Ser Asp Lys Thr His Thr Cys Pro Pro Cys Pro
    290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
            340                 345                 350

Val Asp Gly Val Glu Val His Asn Ala Lys Thr Lys Pro Arg Glu Glu
        355                 360                 365

Gln Tyr Asn Ser Thr Tyr Arg Val Val Ser Val Leu Thr Val Leu His
    370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Asp Glu Leu
            420                 425                 430

Thr Lys Asn Gln Val Ser Leu Thr Cys Leu Val Lys Gly Phe Tyr Pro
        435                 440                 445

Ser Asp Ile Ala Val Glu Trp Glu Ser Asn Gly Gln Pro Glu Asn Asn
    450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
            500                 505                 510

Lys Ser Leu Ser Leu Ser Pro Gly Lys Leu Asp Pro Lys Phe Trp Val
        515                 520                 525

Leu Val Val Val Gly Gly Val Leu Ala Cys Tyr Ser Leu Leu Val Thr
    530                 535                 540

Val Ala Phe Ile Ile Phe Trp Val Thr Arg Gly Ser Lys Arg Gly Arg
545                 550                 555                 560

Lys Lys Leu Leu Tyr Ile Phe Lys Gln Pro Phe Met Arg Pro Val Gln
                565                 570                 575

Thr Thr Gln Glu Glu Asp Gly Cys Ser Cys Arg Phe Pro Glu Glu Glu
            580                 585                 590

Glu Gly Gly Cys Glu Leu Arg Val Lys Phe Ser Arg Ser Ala Asp Ala
        595                 600                 605

Pro Ala Tyr Gln Gln Gly Gln Asn Gln Leu Tyr Asn Glu Leu Asn Leu
    610                 615                 620

Gly Arg Arg Glu Glu Tyr Asp Val Leu Asp Lys Arg Arg Gly Arg Asp
625                 630                 635                 640

Pro Glu Met Gly Gly Lys Pro Arg Arg Lys Asn Pro Gln Glu Gly Leu
                645                 650                 655

Tyr Asn Glu Leu Gln Lys Asp Lys Met Ala Glu Ala Tyr Ser Glu Ile
            660                 665                 670
```

```
-continued

Gly Met Lys Gly Glu Arg Arg Gly Lys Gly His Asp Gly Leu Tyr
        675             680             685
Gln Gly Leu Ser Thr Ala Thr Lys Asp Thr Tyr Asp Ala Leu His Met
    690                 695                 700
Gln Ala Leu Pro Pro Arg
705             710
```